(12) United States Patent
Wang et al.

(10) Patent No.: US 11,643,450 B2
(45) Date of Patent: *May 9, 2023

(54) CHEMOENZYMATIC GLYCOENGINEERING OF ANTIBODIES AND FC FRAGMENTS THEREOF

(71) Applicant: UNIVERSITY OF MARYLAND, BALTIMORE, Baltimore, MD (US)

(72) Inventors: Lai-Xi Wang, Ellicott City, MD (US); Wei Huang, Shanghai (CN)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/097,534

(22) Filed: Nov. 13, 2020

(65) Prior Publication Data

US 2021/0061868 A1  Mar. 4, 2021

Related U.S. Application Data

(60) Division of application No. 16/431,907, filed on Jun. 5, 2019, now Pat. No. 10,836,805, which is a division of application No. 15/843,160, filed on Dec. 15, 2017, now Pat. No. 10,344,063, which is a continuation of application No. 15/256,854, filed on Sep. 6, 2016, now Pat. No. 9,845,360, which is a division of application No. 14/376,248, filed as application No. PCT/US2013/025553 on Feb. 11, 2013, now Pat. No. 9,434,786.

(60) Provisional application No. 61/597,468, filed on Feb. 10, 2012.

(51) Int. Cl.
| | |
|---|---|
| A61P 35/00 | (2006.01) |
| C07K 14/47 | (2006.01) |
| A61K 47/68 | (2017.01) |
| C12N 1/20 | (2006.01) |
| C07K 16/28 | (2006.01) |
| C07K 16/00 | (2006.01) |
| C07K 16/18 | (2006.01) |
| C12N 9/24 | (2006.01) |
| C12P 21/00 | (2006.01) |
| A61P 31/18 | (2006.01) |
| C12R 1/46 | (2006.01) |

(52) U.S. Cl.
CPC ........ *C07K 14/473* (2013.01); *A61K 47/6849* (2017.08); *A61K 47/6867* (2017.08); *A61P 31/18* (2018.01); *A61P 35/00* (2018.01); *C07K 14/4725* (2013.01); *C07K 16/00* (2013.01); *C07K 16/18* (2013.01); *C07K 16/2809* (2013.01); *C07K 16/2887* (2013.01); *C12N 1/20* (2013.01); *C12N 1/205* (2021.05); *C12N 9/2402* (2013.01); *C12P 21/005* (2013.01); *C12Y 302/01096* (2013.01); *C07K 2317/10* (2013.01); *C07K 2317/14* (2013.01); *C07K 2317/41* (2013.01); *C07K 2317/52* (2013.01); *C07K 2317/72* (2013.01); *C07K 2317/92* (2013.01); *C07K 2317/94* (2013.01); *C12R 2001/46* (2021.05)

(58) Field of Classification Search
CPC . A61K 47/6849; A61P 35/00; C07K 14/4725; C07K 14/473; C12P 21/005
See application file for complete search history.

(56) References Cited

U.S. PATENT DOCUMENTS

| | | | |
|---|---|---|---|
| 7,524,821 B2 | 4/2009 | Wang et al. | |
| 7,556,806 B2 | 7/2009 | Wang | |
| 7,604,804 B2 | 10/2009 | Wang et al. | |
| 7,728,106 B2 | 6/2010 | Wang | |
| 7,807,405 B2 | 10/2010 | Wang | |
| 8,354,247 B2 | 1/2013 | Wang | |
| 8,889,128 B2 | 11/2014 | Bjorck et al. | |
| 8,900,826 B2 | 12/2014 | Wang | |
| 9,434,786 B2 * | 9/2016 | Wang | C12Y 302/01096 |
| 9,845,360 B2 * | 12/2017 | Wang | C07K 16/2887 |
| 10,344,063 B2 * | 7/2019 | Wang | A61K 47/6849 |
| 10,836,805 B2 * | 11/2020 | Wang | C07K 16/00 |
| 2005/0064540 A1 | 3/2005 | Defrees et al. | |
| 2005/0159341 A1 | 7/2005 | Wang et al. | |

(Continued)

FOREIGN PATENT DOCUMENTS

| | | |
|---|---|---|
| EP | 1461445 | 8/2008 |
| WO | 20080071418 | 6/2008 |

(Continued)

OTHER PUBLICATIONS

Kato T., et al. Identification of an endo-β-N-acetylglucosaminidase gene in Caenorhabditis elegans and its expression in *Escherichia coli*. Glycobiology, 2002, 12, 581-587.

(Continued)

*Primary Examiner* — Mary Maille Lyons
(74) *Attorney, Agent, or Firm* — Tristan A. Fuierer; Casimir Jones SC

(57) ABSTRACT

The present invention provides for recombinant Endo-S mutants that exhibit reduced hydrolysis activity and increased transglycosylation activity for the synthesis of glycoproteins wherein a desired sialylated oxazoline or synthetic oligosaccharide oxazoline is added to a core fucosylated or nonfucosylated GlcNAc-protein acceptor. Such recombinant Endo-S mutants are useful for efficient glycosylation remodeling of IgG1-Fc domain to provide different antibody glycoforms carrying structurally well-defined Fc N-glycans.

8 Claims, 27 Drawing Sheets

Specification includes a Sequence Listing.

(56) References Cited

U.S. PATENT DOCUMENTS

| | | |
|---|---|---|
| 2005/0176642 A1 | 8/2005 | Wang et al. |
| 2005/0244424 A1 | 11/2005 | Wang |
| 2007/0224211 A1 | 9/2007 | Wang |
| 2008/0014196 A1 | 1/2008 | Yan |
| 2008/0138855 A1 | 6/2008 | Wang |
| 2009/0004179 A1 | 1/2009 | Ravetch et al. |
| 2009/0117154 A1 | 5/2009 | Wang et al. |
| 2010/0173323 A1 | 7/2010 | Strome et al. |
| 2010/0221241 A1 | 9/2010 | DeVico et al. |
| 2010/0317083 A1 | 12/2010 | Allhorn et al. |
| 2011/0263828 A1 | 10/2011 | Wong et al. |
| 2012/0226024 A1 | 9/2012 | Wang et al. |

FOREIGN PATENT DOCUMENTS

| | | |
|---|---|---|
| WO | 2010057626 | 5/2010 |
| WO | 2011039150 | 4/2011 |

OTHER PUBLICATIONS

Kirsch, P. et al. Synthesis of N-Acetylglucosaminyl Asparagine-Substituted Puromycin Analogues, Bioorg Med Chem, 1995, 3, 1631-1636.

Koene, H. R. et al. FcγRIIIa-158V/F polymorphism influences the binding of IgG by natural killer cell FcγRIIIa, independently of the FcγRIIIa-48L/R/H phenotype. Blood 1997, 90, 1109-1114.

Krapp, S. et al. Structural Analysis of Human IgG-Fc Glycoforms Reveals a Correlation Between Glycosylation and Structural Integrity. J. Mol. Biol. 2003, 325, 979-989.

Kuhn, P. et al. Crystal Structure of Peptide-N4-(N-acetyl-β-D-glucosaminyl) asparagine Amidase F at 2.2-Å Resolution, Biochemistry 1994, 33, 11699-11706.

Li, B. et al. Highly Efficient Endoglycosidase-Catalyzed Synthesis of Glycopeptides Using Oligosaccharide Oxazolines as Donor Substrates. J. Am. Chem. Soc. 2005, 127, 9692-9693.

Li, H. et al. Chemoenzymatic synthesis of CD52 glycoproteins carrying native N-glycans, Bioorg. Med. Chem. Lett., 2005, 15, 895-898.

Li, H. et al. Chemoenzymactic Synthesis of HIV-1 V3 Glycopeptides Carrying Two N-Glycans and Effects of Glycosylation on the Peptide Domain, J. Org. Chem., 2005, 70, 9990-9996.

Li, H. et al. Optimization of humanized IgGs in glycoengineered Pichia pastoris. Nat. Biotechnol. 2006, 24, 210-215.

Li, B. et al. A Highly Efficient Chemoenzymatic Approach toward Glycoprotein Synthesis, Org Lett, 2006, 8, 3081-3084.

Ling Z., et al. The x-ray crystal structure of an Arthrobacter protophormiae endo-β-N-acetylglucosaminidase reveals a (β/α)8 catalytic domain, two ancillary domains, and active site residues key for transglycosylation activity. J. Mol. Biol. 2009, 389, 1-9.

Macmillan, D. et al. Modular Assembly of Glycoproteins: Towards the Synthesis of GlyCAM-1 Using Expressed Protein Ligation, Angew. Chem. Int. Ed., 2004, 43, 1355-1359.

Matsumiya, S. et al. Structural Comparison of Fucosylated and Nonfucosylated Fc Fragments of Human Immunoglobulin G1. J. Mol. Biol. 2007, 368, 767-779.

Muramatsu, H. et al. Molecular Cloning and Expression of Endo-β-N-Acetylglucosaminidase D, Which Acts on the Core Structure of Complex T Asparagine-Linked Oligosaccharides, Journal of Biochemistry, 2001, 129, 923-928.

Nimmerjahn, F. et al. Fcγ receptors as regulators of immune responses. Nat. Rev. Immunol. 2008, 8, 34-47.

Nimmerjahn, F. et al. Anti-inflammatory actions of intravenous immunoglobulin. Annu. Rev. Immunol. 2008, 26, 513-533.

Niwa, R. et al. Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma. Cancer Res. 2004, 64, 2127-2133.

Ochiai H., et al. Expeditious chemoenzymatic synthesis of homogeneous N-glycoproteins carrying defined oligosaccharide ligands. J. Am. Chem. Soc. 2008, 130, 13790-13803.

Parsons, T.B. et al. Synthesis of a truncated bi-antennary complex-type N-glcan oxazoline: glycosylation catalysed by the endohexosaminidases Endo A and Endo M, Org. Biomol. Chem., 2009, 7, 3128-3140.

Parsons, T.B. et al. *Streptococcus pneumoniae* endohexosaminidase D; feasibility of using N-glycan oxazoline donors for synthetic glycosylation of a GlcNAc-asparagine acceptor, Org Biomol Chem, 2010, 8, 1861-1869.

Piontek, C. et al. Semisynthesis of a Homogeneous Glycoprotein Enzyme: Ribonuclease C: Part 1, Angew. Chem. Int. Ed., 2009, 48, 1936-1940.

Piontek, C. et al. Semisynthesis of a Homogeneous Glycoprotein Enzyme: Ribonuclease C: Part 2, Angew. Chem. Int. Ed., 2009, 48, 1941-1945.

Plummer, Jr., T.H. et al. Procine Fibrinogen Glycopeptides: Substrates for Detecting Endo-β-N-acetylglucosaminidases F2 and F31, Anal. Biochem. 1996, 235, 98-101.

Raju, T. S. et al. Glycosylation in the Fc domain of IgG increases resistance to proteolytic cleavage by papain. J. Biochem. Biophys. Res. Commun. 2006, 341, 797-803.

Rao, V. et al. Crystal structure of endo-β-N-acetylglucosaminidase at 1.9 Å resolution: active-site geometry and substrate recognition, Structure 1995, 3, 449-457.

Rao V. et al. Mutations of endo-β-N-acetylglucosaminidase H active site residues Asp-130 and Glu-132: activities and conformations. Protein Sci. 1999, 8, 2338-2346.

Reddy, A. et al. High-level expression of the endo-β-N-acetylglucosaminidase F2 gene in *E.coli*: step purification to homogeneity. Glycobiology 1998, 8, 633-636.

Rich, J.R. et al. Emerging methods for the production of homogeneous human glycoproteins, Nat Chem Biol, 2009, 4, 206-215.

Rising, T. W. et al. Endoexosaminidase M: Exploring and Exploiting Enzyme Substrate Specificity, ChemBioChem, 2006, 7, 1177-1180.

Rising, T. W. et al. Endohexosaminidase-Catalysed Glycosylation with Oxazoline Donors: Fine Tuning of Catalytic Efficiency and Reversibility, Chem. Eur. J., 2008, 14, 6444-6464.

Robbins, P.W. et al. Primary structure of the Streptomyces enzyme endo-β-N-acetylglucosaminidase H., J. Biol. Chem. 1984, 259, 7577-7583.

Sazinsky, S. L. et al. Aglycosylated immunoglobulin G1 variants productively engage activating Fc receptors. Proc. Natl. Acad. Sci. U.S.A. 2008, 105, 20167-20172.

Schiestl, M. et al. Acceptable changes in quality attributes of glycosylated biopharmaceuticals. Nat. Biotechnol. 2011, 29, 310-312.

Schwarz F., et al. A combined method for producing homogeneous glycoproteins with eukaryotic N-glycosylation. Nat. Chem. Biol. 2010, 6, 264-266.

Shields, R. L. et al. Lack of fucose on human IgG1 N-linked oligosaccharide improves binding to human FcγRIIIA and antibody-dependent cellular toxicity. J. Biol. Chem. 2002, 277, 26733-26740.

Shinkawa, T. et al. The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity. J. Biol. Chem. 2003, 278, 3466-3473.

Sletten, E. M. et al. From Mechanism to Mouse: A Tale of Two Bioorthogonal Reactions. Acc. Chem. Res. 2011, 44, 666-676.

Sondermann, P. et al. The 3.2-Å crystal structure of the human IgG1 Fc fragment-FcγRIII complex. Nature 2000, 406, 267-273.

Stanley, P. et al. Molecular analysis of three gain-of-function CHO mutants that add the bisecting GlcNAc to N-glycans. Glycobiology 2005, 15, 43-53.

Strasser, R. et al. Improved Virus Neutralization by Plant-produced Anti-HIV Antibodies with a Homogeneous β1,4-Galactosylated N-Glycan Profile. Biol. Chem. 2009, 284, 20479-20485.

Strome, S. E. et al. A mechanistic perspective of monoclonal antibodies in cancer therapy beyond target-related effects. Oncologist 2007, 12, 1084-1095.

(56) References Cited

OTHER PUBLICATIONS

Sun, B. et al. Pre-Activation-Based One-Pot Synthesis of an α-(2,3)-Sialylated Core-Fucosylated Complex Type Bi-Antennary N-Glycan Dodecasaccharide, Chemistry—A European Journal, 2008, 14, 7072-7081.
Takahashi, N. et al. Three-dimensional elution mapping of pyridylaminated N-linked neutral and sialyl oligosaccharides. Anal. Biochem. 1995, 226, 139-146.
Takegawa, K. et al. Cloning, Sequencing, and Expression of Arthrobacter protophormiae Endo-β-N-acetylglucosaminidase, Arch. Biochem. Biophys., 1997, 338, 22-28.
Tarantino, S.L. et al. Molecular Cloning and Amino Acid Sequence of Peptide-N4-(N-acetyl-β-D-glucosaminyl) asparagine Amidase from Flavobacterium meningosepticum, J. Biol. Chem. 1990, 265, 6961-6966.
Tarantino, A. L., et al. Multiple endoglycosidase (Endo) F activities expressed by Flavobacterium meningosepticum. Endo F1: molecular cloning, primary sequence, and structural relationship to Endo H., J. Biol. Chem. 1992, 267, 3868-3872.
Tarantino, A.L. Multiple Endoglycosidase F Activities Expressed by Flavobacterium meningosepticum Endoglycosidases F2 and F3, J. Biol. Chem., 268 (13), 9702-9708 (1993).
Tarantino, A.L. et al. Enzymatic Deglycosylation of Asparagine-Linked Glycans: Purification, Properties, and Specificity of Oligosaccharide Cleaving Enzymes from Flavobacterium meningosepticum, Methods Enzymol. 1994, 230, 44 57.
Tarantino, A.L. et al. Overexpression and purification of non-glycolated recombinant endo-β-N-acetylglucosaminidase, Glycobiology 1995, 5, 599-601.
Tews, I. et al. Substrate-Assisted Catalysis Unifies Two Families of Chitinolytic Enzymes, J. Am. Chem. Soc. 1997, 119, 7954-7959.
Trimble, R.B. Transfer of Glycerol by Endo-β-N-acetylglucosaminidase F to Oligosaccharides during Chitobiose Core Cleavage, J Biol Chem, 1986, 261, 12000-12005.
Trimble, R.B. et al. Identification of Distinct Endoglycosidase (Endo) Activities in Flavobacterium meningosepticum: Endo F1, Endo F2, and Endo F3, J. Biol. Chem. 1991, 266, 1646-1651.
Uchiyama, T. et al. Per-O-Trimethylsilyl-α-L-Fucopyranosyl Iodide: A Novel Glycosylating Agent for Terminal α-L-Fucosylation, Synlett, 1996, 499-501.
Umana, P. et al. Engineered glycoforms of an antineuroblastoma IgG1 with optimized antibody-dependent cellular cytotoxic activity. Nat. Biotechnol. 1999, 17, 176-180.
Umekawa, M. et al. Mutants of Mucor hiemalis Endo-β-N-acetylglucosaminidase Show Enhanced Transglycosylation and Glycosynthase-like Activities. J. Biol. Chem. 2008, 283, 4469-4479.
Umekawa, M. et al. Efficient glycosynthase mutant derived from Mucor hiemalis endo-β-N-acetylglucosaminidase capable of transferring oligosaccharide from both sugar oxazoline and natural N-glycan. J. Biol. Chem. 2010, 285, 511-521.
Umekawa, M. et al. Efficient transfer of sialo-oligosaccharide onto proteins by combined use of a glycosynthase-like mutant of Mucor hiemalis endoglycosidase and synthetic sialo-complex-type sugar oxazoline. Biochim. Biophys. Acta 2010, 1800, 1203-1209.
Van Kasteren, S.L. et al. Expanding the diversity of chemical protein modification allows post-translational mimcry, Nature, 2007, 446, 1105-1109.
Van Roey P., et al. Crystal structure of endo-β-N-acetylglucosaminidase F1, an α/βp-barrel enzyme adapted for a complex substrate. Biochemistry, 1994, 33, 13989-13996.
Waddling, C. A. et al. Structural Basis for the Substrate Specificity of Endo-β-N-acetylglucosaminidase F3. Biochemistry 2000, 39, 7878-7885.
Walsh, G. et al. Post-translational modifications in the context of therapeutic proteins, Nat. Biotechnol., 2006, 24 (10), 1241-1252.
Wan, H. Z. et al. Rapid method for monitoring galactosylation levels during recombinant antibody production by electrospray mass spectrometry with selective-ion monitoring. J. Chromatogr., A 2001, 913, 437-446.

Wang, L.X. Chemoenzymatic synthesis of glycopeptides and glycoproteins through endoglycosidase-catalyzed transglycosylation, Carbohydr. Res., 2008, 343, 1509-1522.
Wang, L. X. The amazing transglycosylation activity of endo-β-N-acetylglucosaminidases. Trends Glycosci. Glycotechnol. 2011, 23, 33-52.
Wang, L. X. et al. Emerging Technologies for Making Glycan-Defined Glycoproteins. ACS Chem. Biol. 2012, 7, 110-122.
Wang, L.X. et al. Enzymatic transglycosylation for glycoconjugate synthesis, Curr Opin Chem Biol, 2009, 13, 592-600.
Wei, Y. et al. Glycoengineering of Human IgG1-Fc through Combined Yeast Expression and in Vitro Chemoenzymatic Glycosylation. Biochemistry 2008, 47, 10294-10304.
Wildt, S. et al. The Humanization of N-Glycosylation Pathways in Yeast, Nat. Rev. Microbiol., 2005, 3, 119-128.
Wormaid, M. R. et al. Variations in Oligosaccharide-Protein Interactions in Immunoglobulin G Determine the Site-Specific Glycosylation Profiles and Modulate the Dynamic Motion of the Fc Oligosaccharides. Biochemistry 1997, 36, 1370-1380.
Yamaguchi, Y. et al. Glycoform-dependent conformational alteration of the Fc region of human immunoglobulin G1 as revealed by NMR spectroscopy. Biochem. Biophys. Acta 2006, 1760, 693-700.
Yamamoto, K. et al. Novel Specificities of Mucor hiemalis Endo-β-N-acetylglucosaminidase Acting Complex Asparagine-Linked Oligosaccharides, Biosci Biotechnol Biochem, 1994, 58, 72-77.
Yamamoto, K. Chemo-Enzymatic Synthesis of Bioactive Glycopeptide Using Microboal Endoglycosidase, J. Biosci. Bioeng., 2001, 92, 493-501.
Yamamoto S., et al. Mutational studies on endo-β-N-acetylglucosaminidase D which hydrolyzes core portion of asparagine-linked complex type oligosaccharides. Glycoconj. J., 2005, 22, 35-42.
Yamamoto, Y. et al. Chemical Synthesis of a Glycoprotein Having an Intact Human Complex-Type Sialyloligosaccharide under Boc and Fmoc Synthetic Strategies, J. Am. Chem. Soc., 2008, 130, 501-510.
Yamane-Ohnuki, N. et al. Establishment of FUT8 knockout Chinese hamster ovary cells: An ideal host cell line for producing completely defucosylated antibodies with enhanced antibody-dependent cellular cytotoxicity. Biotechnol. Bioeng. 2004, 87, 614-622.
Yin J., et al. Structural basis and catalytic mechanism for the dual functional endo-β-N-acetylglucosaminidase A, PLoS One 4, 2009 e4658.
Zeng, Y. et al. Glycopeptide Synthesis through endo-Glycosidase-Catalyzed Oligosaccharide Transfer of Sugar Oxazolines: Probing Substrate Structural Requirement, Chem. Eur. J., 2006, 12, 3355-3364.
Zhou, Q. et al. Development of a simple and rapid method for producing non-fucosylated oligomannose containing antibodies with increased effector function. Biotechnol. Bioeng. 2008, 99, 652-665.
Zou, G. et al. Chemoenzymatic Synthesis and Fcβ Receptor Binding of Homogeneous Glycoforms of Antibody Fc Domain. Presence of a Bisecting Sugar Moiety Enhances the Affinity of Fc to FcγIIIa Receptor. J. Am. Chem. Soc. 2011, 133, 18975-18991.
Huang, W. Chemoenymatic Glycoengineering of Intact IgG Antibodies for Gain of Functions, Journal of the American Chemical Society, 2012, 134, 29 , 12308-12318.
Abbott, D. W. et al. *Streptococcus pneumoniae* Endohexosaminidase D, Structural and Mechanistic Insight into Substrate-assisted Catalysis in Family 85 Glycoside Hydrolases (2009) J. Biol. Chem. 284, 11676-11689.
Adams, G. P. et al. Monoclonal antibody therapy of cancer. Nat. Biotechnol. 2005, 23, 1147-1157.
Aggarwal, S. hat's fueling the biotech engine—2010 to 2011. Nat. Biotechnol. 2011, 29, 1083-1089.
Allhorn, M. et al. EndoS from *Streptococcus pyogenes* is hydrolyzed by the cysteine proteinase SpeB and requires glutamic acid 235 and tryptophans for IgG glycan-hydrolyzing activity. BMC Microbiol. 2008, 8, 3.
Amin M. N., et al. Convergent synthesis of homogeneous Glc1Man9GlcNAc2 protein and derivatives as ligands of molecular chaperones in protein quality control. J. Am. Chem. Soc. 2011, 133, 14404-14417.

(56) References Cited

OTHER PUBLICATIONS

Anthony, R. M. et al. Recapitulation of IVIG Anti-Inflammatory Activity with a Recombinant IgG Fc. Science 2008, 320, 373-376.
Anthony, R. M. et al. Identification of a receptor required for the anti-inflammatory activity of IVIG. Proc. Natl. Acad. Sci. U.S.A. 2008, 105, 19571-19578.
Anthony, R.M. et al. Intravenous gammaglobulin suppresses inflammation through a novel TH2 pathway. Nature 2011, 475, 110-113.
Barb, A. W. et al. Branch-Specific Sialylation of IgG-Fc Glycans by ST6Gal-I. Biochemistry 2009, 48, 9705-9707.
Barb, A. W. NMR analysis demonstrates immunoglobulin G N-glycans are accessible and dynamic. Nat. Chem. Biol. 2011, 7, 147-153.
Bennett, C.S. et al. Chemoenzymatic approaches to glycoprotein synthesis. Chem. Soc. Rev., 2007, 36, 1227-1238.
Bernardes, G.J. et al. Combined Approaches to the Synthesis and Study of Glycoproteins. ACS Chem Biol, 2009, 4, 703-713.
Best, M. D. Click Chemistry and Bioorthogonal Reactions: Unprecedented Selectivity in the Labeling of Biological Molecules. Biochemistry 2009, 48, 6571-6584.
Brameld, K.A. et al. Substrate Assistance in the Mechanism of Family 18 Chitinases: Theoretical Studies of Potential Intermediates and Inhibitors, J. Mol. Biol. 1998, 280, 913-923.
Buskas, T. et al. Glycoproteins as versatile tools for glycobiology, Glycobiology, 2006, 16, 113R-136R.
Camilli, R. et al. New Genetic Element Carrying the Erythromycin Resistance Determinant erm(TR) in *Streptococcus pneumoniae*, Antimicrob. Agents Chemother. 2008, 52 (2), 619-625.
Cartron, G. et al. Therapeutic activity of a humanized anti-CD20 monoclonal antibody and polymorphism in IgG Fc receptor FcγRIIIa gene. Blood 2002, 99, 754-758.
Collin, M. et al. Effect of SpeB and EndoS from *Streptococcus pyogenes* on human immunoglobulins. Infect. Immun. 2001, 69, 7187-7189.
Collin, M. et al. EndoS, a novel secreted protein from *Streptococcus pyogenes* with endoglycosidase activity on human IgG. EMBO J. 2001, 20, 3046-3055.
Cox, K. M. et al. Glycan optimization of a human monoclonal antibody in the aquatic plant *Lemna minor*. Nat. Biotechnol. 2006, 24, 1591-1597.
Crispin, M. et al. Carbohydrate and Domain Architecture of an Immature Antibody Glycoform Exhibiting Enhanced Effector Functions. J. Mol. Biol. 2009, 387, 1061-1066.
Eller, S. et al. Synthesis of Pentaantennary N-Glycans with Bisecting GlcNAc and Core Fucose, , Angew. Chem. Int. Ed., 2007, 46, 4173-4175.
Fairbanks, A.J. Endohexosaminidase catalyzed glycosylation with oxazoline donors: The development of robust biocatalytic methods for synthesis of defined homogeneous glycoconjugates Comptes Rendus Chimie (Abstract Only).
Fan, S. Q. et al. Remarkable Transglycosylation Activity of Glycosynthase Mutants of Endo-D, an Endo-β-N-acetylglucosaminidase from *Streptococcus pneumonia*. J. Biol. Chem. 2012, 287, 11272-11281.
Ferrara, C. et al. Unique carbohydrate-carbohydrate interactions are required for high affinity binding between FcγRIII and antibodies lacking core fucose. Proc. Natl. Acad. Sci. U.S.A. 2011, 108, 12669-12674.
Fujita, K. et al. Synthesis of Neoglycoenzymes with Homogeneous N-Linked Oligosaccharides Using Immobilized Endo-β-N-acetylglucosaminidase A, Biochem. Biophys. Res. Commun., 2000, 267, 134-138.
Fujita M., et al. A novel disaccharide substrate having 1,2-oxazoline moiety for detection of transglycosylating activity of endoglycosidases. Biochim. Biophys. Acta, 2001, 1528, 9-14.

Fujita K., et al. Tryptophan-216 is essential for the transglycosylation activity of endo-β-N-acetylglucosaminidase A. Biochem. Biophys. Res. Commun. 2001, 283, 680-686.
Gamblin, D.P. et al. Glycoprotein Synthesis: An Update, Chem. Rev., 2009, 109, 131-163.
Goodfellow, J. J. et al. An Endoglycosidase with Alternative Glycan Specificity Allows Broadened Glycoprotein Remodelling. J. Am. Chem. Soc. 2012, 134, 8030-8033.
Grogan, M. J. et al. Homogeneous Glycoepeptides and Glycoproteins for Biological Investigation, Annu. Rev. Biochem., 2002, 71, 593-634.
Guhr, T. et al. Enrichment of sialylated IgG by lectin fractionation does not enhance the efficacy of immunoglobulin G in a murine model of immune thrombocytopenia. PLoS One 2011, 6, e21246.
Guile, G. R. et al. A rapid high-resolution high-performance liquid chromatographic method for separating glycan mixtures and analyzing oligosaccharide profiles. Anal. Biochem. 1996, 240, 210-226.
Hamilton, S.R. et al. Production of Complex Human Glycoproteins in Yeast, Science, 2003, 301, 1244-1246.
Hamilton, S.R. et al. Humanization of Yeast to Produce Complex Terminally Sialylated Glycoproteins, Science, 2006, 313, 1441-1443.
Haneda, K. et al. Transglycosylation of intact sialo complex-type oligosaccharies to the N-acetylglucosamine moieties of glycopepetides by Mucor hiemalis endo-β-N-acetylglucosaminidase, Carbohydrate Res., 1996, 292, 61-70.
Heidecke, C.D. et al. Enhanced Glycosylation with Mutants of Endohexosaminidase A (EndoA), Chembiochem, 2008, 9, 2045-2051.
Hessell, A. J. et al. Fc receptor but not complement binding is important in antibody protection against HIV. Nature 2007, 449, 101-104.
Hirano, K. et al. Design and Synthesis of a Homogeneous Erythropoietin Analogue with Two Human Complex-Type Sialyloligosaccharides: Combined Use of Chemical and Bacterial Protein Expression Methods, Angew. Chem. Int. Ed., 2009, 48, 9557-9560.
Huang, W. et al. Expeditious chemoenzymatic synthesis of CD52 glycopeptide anitgens, Org. Biomol. Chem. 2010, 8, 5224-5233.
Huang, W. et al. Glycosynthases Enable a Highly Efficient Chemoenzymatic Synthesis of N-Glycoproteins Carrying Intact Natural N-Glycans. J. Am. Chem. Soc. 2009, 131, 2214-2223.
Huang, W. et al. Arthrobacter Endo-β-N-Acetylglucosaminidase Shows Transglycosylation Activity on Complex-Type N-Glycan Oxazolines: One-Pot Conversion of Ribonuclease B to Sialylated Ribonuclease C. ChemBioChem 2010, 11, 1350-1355.
Huang, W. et al. Unusual Transglycosylation Activity of Flavobacterium meningosepticum Endoglycosidases Enables Convergent Chemoenzymatic Synthesis of Core Fucosylated Complex N-Glycopeptides. ChemBioChem 2011, 12, 932-941.
Huhn, C. et al. IgG glycosylation analysis. Proteomics 2009, 9, 882-913.
Jefferis, R., Glycosylation of Recombinant Antibody Therapeutics. Biotechnol. Prog. 2005, 21, 11-16.
Jefferis, R. Glycosylation as a strategy to improve antibody-based therapeutics. Nat. Rev. Drug Discovery 2009, 8, 226-234.
Jefferis, R. Glycosylation of antibody therapeutics: optimisation for purpose. Methods Mol. Biol. 2009, 483, 223-238.
Johnson, P. et al. The mechanisms of action of rituximab in the elimination of tumor cells. Semin. Oncol. 2003, 30, 3-8.
Kadowaki, S., et al., 4 (1991) Microbial endo-β-N-acetylglucosaminidases acting on complex-type sugar chains of glycoproteins. J. Biochem. 110, 17-21.
Kaneko, Y. et la. Anti-Inflammatory Activity of Immunoglobulin G Resulting from Fc Sialylation. Science 2006, 313, 670-673.

\* cited by examiner

```
EndoS   181 RTIPWRFLAGGDNSGIAEDTSKYPNTPEGNKALAKAIVDEYVYKYNLDGLDVDVEHDSIP 240
EndoF3   84 QNIDDDVSWQSSKPGGFASAAAYG----------DAIKSIVIDKWKLDGISLDIEHS--- 169
```

Figure 2

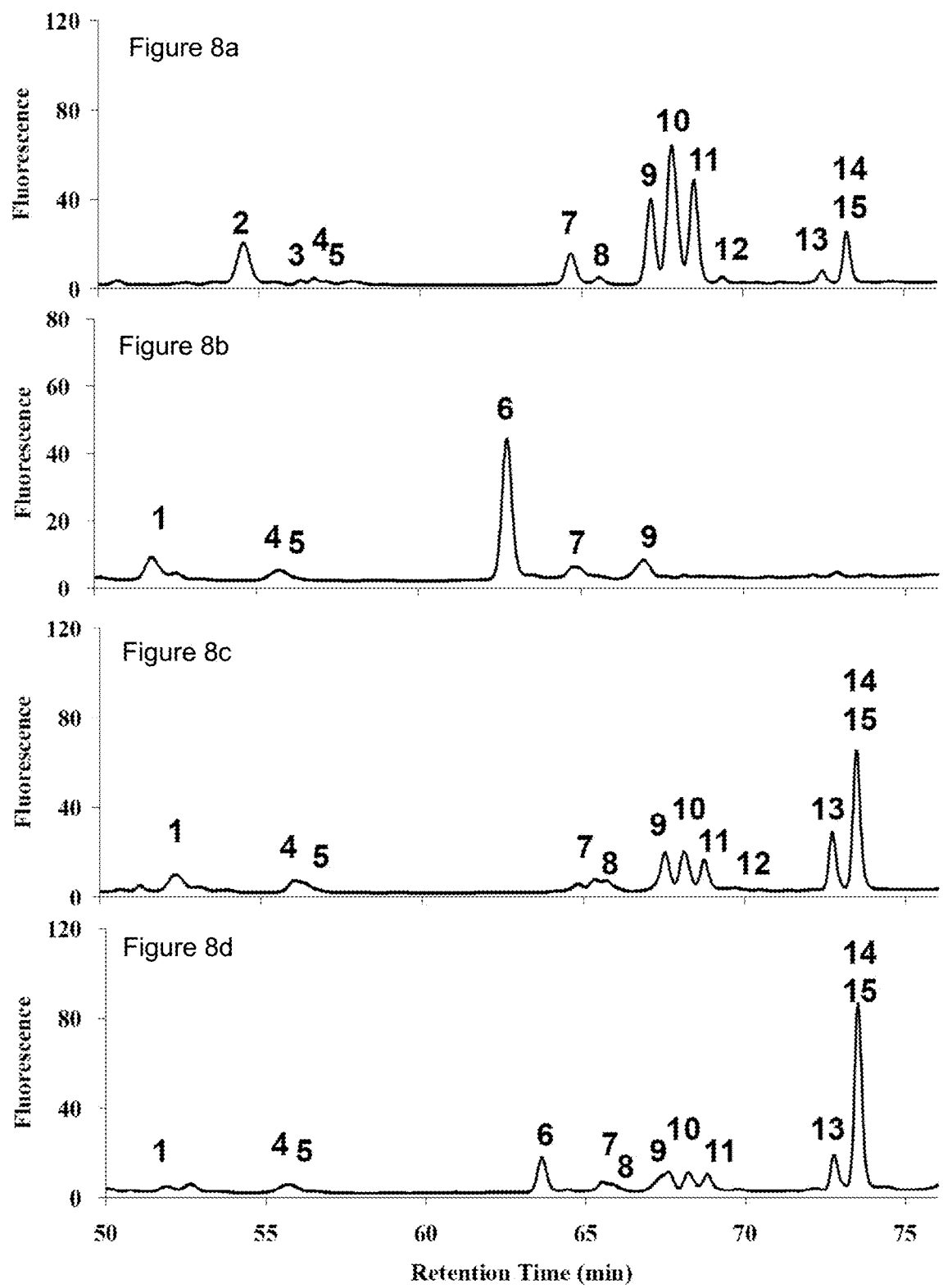

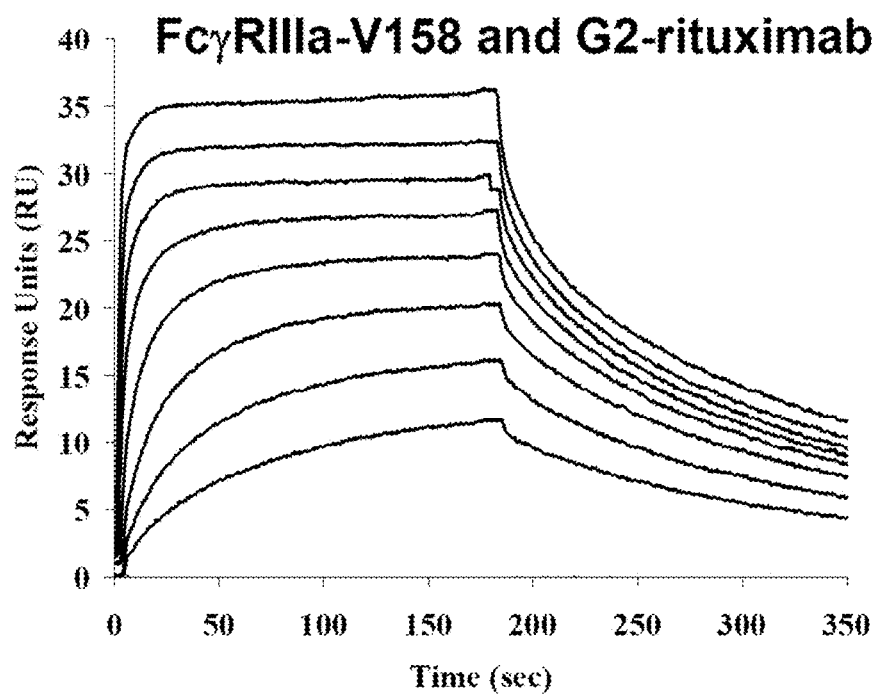
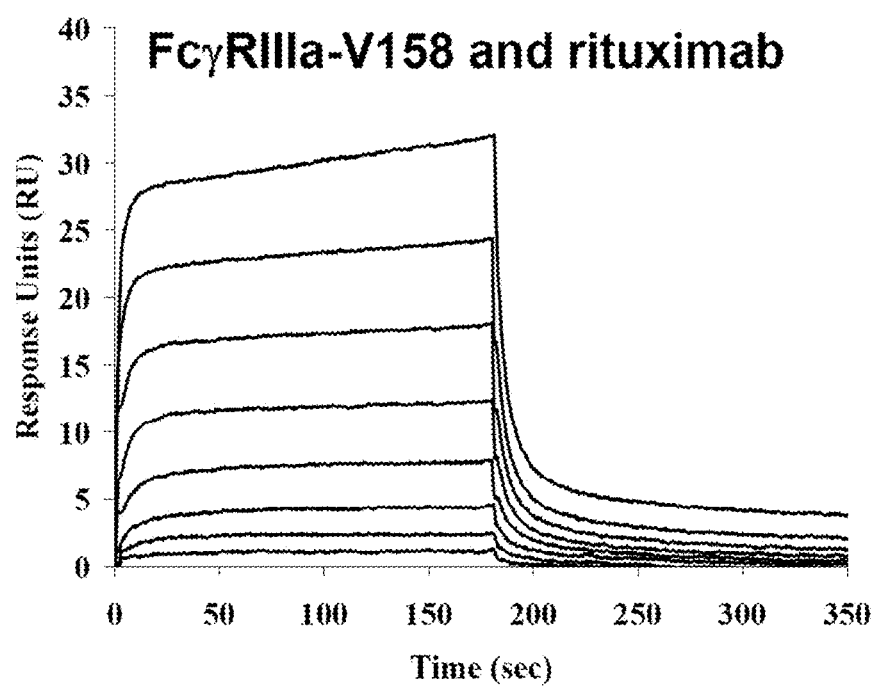
Figure 9A

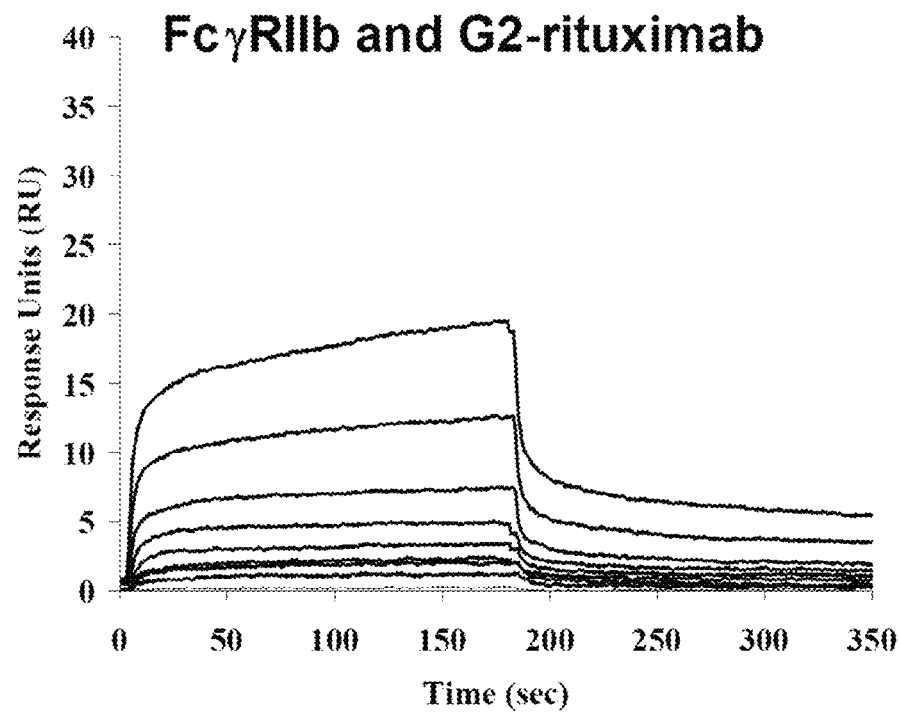
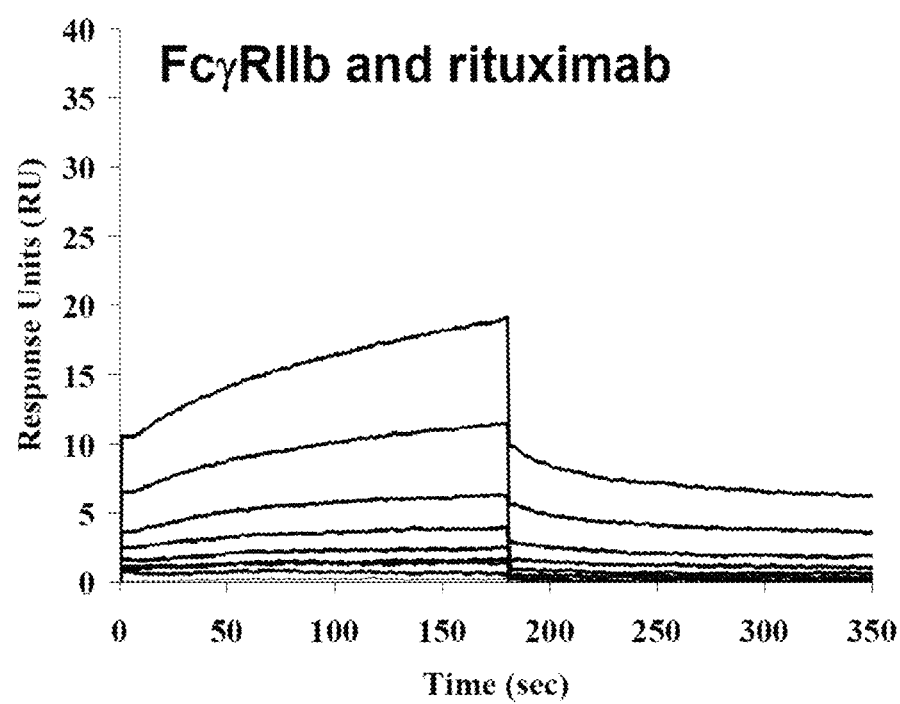
Figure 9C

Figure 17A

MDKHLLVKRT LGCVCAATLM GAALATHHDS LNTVKAEEKT VQVQKGLPSI DSLHYLSENS
KKEFKEELSK AGQESQKVKE ILAKAQQADK QAQELAKMKI PEKIPMKPLH GPLYGGYFRT
WHDKTSDPTE KDKVNSMGEL PKEVDLAFIF HDWTKDYSLF WKELATKHVP KLNKQGTRVI
RTIPWRFLAG GDNSGIAEDT SKYPNTPEGN KALAKAIVDE YVYKYNLDGL DVQVEHDSIP
KVDKKEDTAG VERSIQVFEE IGKLIGPKGV DKSRLFIMDS TYMADKNPLI ERGAPYINLL
LVQVYGSQGE KGGWEPVSNR PEKTMEERWQ GYSKYIRPEQ YMIGFSFYEE NAQEGNLWYD
INSRKDEDKA NGINTDITGT RAERYARWQP KTGGVKGGIF SYAIDRDGVA HQPKKYAKQK
EFKDATDNIF HSDYSVSKAL KTVMLKDKSY DLIDEKDFPD KALREAVMAQ VGTRKGDLER
FNGTLRLDNP AIQSLEGLNK FKKLAQLDLI GLSRITKLDR SVLPANMKPG KDTLETVLET
YKKDNKEEPA TIPPVSLKVS GLTGLKELDL SGFDRETLAG LDAATLTSLE KVDISGNKLD
LAPGTENRQI FDTMLSTISN HVGSNEQTVK FDKQKPTGHY PDTYGKTSLR LPVANEKVDL
QSQLLFGTVT NQGTLINSEA DYKAYQNHKI AGRSFVDSNY HYNNFKVSYE NYTVKVTDST
LGTTTDKTLA TDKEETYKVD FFSPADKTKA VHTAKVIVGD EKTMMVNLAE GATVIGGSAD
PVNARKVFDG QLGSETDNIS LGWDSKQSII FKLKEDGLIK HWRFFNDSAR NPETTNKPIQ
EASLQIFNIK DYNLDNLLEN PNKFDDEKYW ITVDTYSAQG ERATAFSNTL NNITSKYWRV
VFDTKGDRYS SPVVPELQIL GYPLPNADTI MKTVTTAKEL SQQKDKFSQK MLDELKIKEM
ALETSLNSKI FDVTAINANA GVLKDCIEKR QLLKK (SEQ ID NO: 2)

Figure 17B

MDKHLLVKRT LGCVCAATLM GAALATHHDS LNTVKAEEKT VQVQKGLPSI DSLHYLSENS
KKEFKEELSK AGQESQKVKE ILAKAQQADK QAQELAKMKI PEKIPMKPLH GPLYGGYFRT
WHDKTSDPTE KDKVNSMGEL PKEVDLAFIF HDWTKDYSLF WKELATKHVP KLNKQGTRVI
RTIPWRFLAG GDNSGIAEDT SKYPNTPEGN KALAKAIVDE YVYKYNLDGL DVAVEHDSIP
KVDKKEDTAG VERSIQVFEE IGKLIGPKGV DKSRLFIMDS TYMADKNPLI ERGAPYINLL
LVQVYGSQGE KGGWEPVSNR PEKTMEERWQ GYSKYIRPEQ YMIGFSFYEE NAQEGNLWYD
INSRKDEDKA NGINTDITGT RAERYARWQP KTGGVKGGIF SYAIDRDGVA HQPKKYAKQK
EFKDATDNIF HSDYSVSKAL KTVMLKDKSY DLIDEKDFPD KALREAVMAQ VGTRKGDLER
FNGTLRLDNP AIQSLEGLNK FKKLAQLDLI GLSRITKLDR SVLPANMKPG KDTLETVLET
YKKDNKEEPA TIPPVSLKVS GLTGLKELDL SGFDRETLAG LDAATLTSLE KVDISGNKLD
LAPGTENRQI FDTMLSTISN HVGSNEQTVK FDKQKPTGHY PDTYGKTSLR LPVANEKVDL
QSQLLFGTVT NQGTLINSEA DYKAYQNHKI AGRSFVDSNY HYNNFKVSYE NYTVKVTDST
LGTTTDKTLA TDKEETYKVD FFSPADKTKA VHTAKVIVGD EKTMMVNLAE GATVIGGSAD
PVNARKVFDG QLGSETDNIS LGWDSKQSII FKLKEDGLIK HWRFFNDSAR NPETTNKPIQ
EASLQIFNIK DYNLDNLLEN PNKFDDEKYW ITVDTYSAQG ERATAFSNTL NNITSKYWRV
VFDTKGDRYS SPVVPELQIL GYPLPNADTI MKTVTTAKEL SQQKDKFSQK MLDELKIKEM
ALETSLNSKI FDVTAINANA GVLKDCIEKR QLLKK  (SEQ ID NO: 3)

CHEMOENZYMATIC GLYCOENGINEERING OF ANTIBODIES AND FC FRAGMENTS THEREOF

CROSS-REFERENCE TO RELATED APPLICATION

This application is a divisional application claiming priority to U.S. patent application Ser. No. 16/431,907 filed on Jun. 5, 2019, now U.S. Pat. No. 10,836,805, which is a divisional application claiming priority to U.S. patent application Ser. No. 15/843,160 filed on Dec. 15, 2017, now U.S. Pat. No. 10,344,063, which is a continuation application claiming priority to U.S. patent application Ser. No. 15/256,854 filed on Sep. 6, 2016, now U.S. Pat. No. 9,845,360, which is a divisional application of U.S. patent application Ser. No. 14/376,248, filed on Aug. 1, 2014, now U.S. Pat. No. 9,434,786, which in turn was filed under the provisions of U.S.C. § 371 and claimed priority to International Patent Application No. PCT/US2013/025553 filed on Feb. 11, 2013, which in turn claimed priority of U.S. Provisional Application No. 61/597,468 filed on Feb. 10, 2012, the contents of which are incorporated by reference herein for all purposes.

GOVERNMENT RIGHTS IN INVENTION

This invention was made with government support under Grant Numbers GM080374 and GM096973 awarded by the National Institutes of Health. The government has certain rights in the invention.

BACKGROUND OF THE INVENTION

Field of the Invention

The invention relates to glycoprotein synthesis, and more particularly, to the use of a recombinant and mutant Endo S, an Endo-β-N-acetylglucosaminidase from *Streptococcus pyogenes*, that possesses transglycosylation activity and limited hydrolyzing activity thereby providing for efficient glycosylation remodeling of antibody-Fc domain.

Description of the Related Art

Monoclonal antibodies (mAbs) of the IgG type are an important class of therapeutic proteins used for the treatment of cancer, autoimmune, and infectious diseases.(1-3) IgG antibodies are composed of two heavy chains and two light chains that are associated to form three distinct protein domains, including two variable Fab domains and a constant (crystallizable) Fc domain linked by a flexible hinge region. The Fab domains are responsible for antigen binding, while the Fc domain is engaged in Fc receptor-mediated effector functions, such as antibody-dependent cellular cytotoxicity (ADCC) and complement-dependent cytotoxicity (CDC).(2, 4) The Fc domain is a homodimer bearing two N-glycans at the conserved N-glycosylation sites (N297). The attached oligosaccharides are biantennary complex type with considerable structural heterogeneity, in which the N-linked heptasaccharide core can be differentially decorated with core fucose (Fuc), bisecting N-acetylglucosamine (GlcNAc), terminal galactose (Gal), and terminal sialic acid (Sia) as shown in FIG. 1.(5-7) X-ray crystallographic and NMR structural studies indicate that the Fc glycans are sandwiched between the two CH2/CH3 subdomains and have multiple noncovalent interactions with the Fc domains.(8-14) These studies have shown that the attachment of different Fc glycans can have distinct impact on the Fc domain conformations, implicating an important role of glycosylation in maintaining an appropriate Fc domain structures for interactions with respective Fc receptors associated with antibody's effector functions.(8-14)

It has been further demonstrated that the fine structures of Fc N-glycans are important determinants of the pro- and anti-inflammatory activities of antibodies.(2, 15) For example, the lack of the core fucose, as well as the attachment of a bisecting GlcNAc moiety, dramatically enhances the affinity of antibody for the FcγIIIa receptor (FcγRIIIa), which is responsible for the antibody-dependent cellular cytotoxicity (ADCC).(11, 16-18) Thus, low-fucose content mAbs are sought out for improved in vivo anticancer efficacy.(19, 20) On the other hand, the terminal α-2,6-sialylated Fc glycoform, a minor component of the intravenous immunoglobulin (IVIG) pooled from the sera of thousands of healthy blood donors, was recently identified as the active species for the anti-inflammatory activity of IVIG in a mouse model of rheumatoid arthritis (RA).(21-23) However, commercially available IgGs, including monoclonal antibodies and IVIG, typically exist as mixtures of glycoforms that are not optimal for their respective therapeutic activities. For instance, the major Fc glycoforms of monoclonal antibodies currently used for cancer treatment are core-fucosylated that possess relatively low affinity for the activation receptor FcγRIIIa, demonstrating low efficacy particularly for those patients with the low-affinity FcγRIIIa-F158 allelic polymorphism.(2, 19, 20)

The impact of glycosylation on the biological functions and therapeutic outcome of IgG antibodies has stimulated tremendous interest in developing methods to control antibody's glycosylation. One approach is to control the glycosylation profiles during production through glycan biosynthetic pathway engineering in various expression systems, including mammalian, plant, and yeast host cells.(24-30) This control of glycosylation has resulted in the production of low-fucose or nonfucosylated monoclonal antibodies with improved ADCC activities. But, the glycoforms that can be generated by this approach have been limited, and in most cases, a complete control to a defined homogeneous glycoform is difficult.

A recent analysis of several therapeutic glycoprotein drugs on the market, including monoclonal antibody rituximab, has indicated significant changes of the glycosylation profiles from different batches produced in different periods. (31) This analysis implicates the challenge in maintaining consistent production of glycoprotein-based drugs and also raises regulatory concerns, as changes of the Fc glycosylation would most likely impact the therapeutic efficacy.

An alternative approach to addressing the inconsistence and heterogeneity in glycosylation of glycoproteins is to perform glycosylation remodeling through trimming off the heterogeneous N-glycans and extending the sugar chains by enzymatic glycosylation.(32, 33) Such enzymatic glycosylation has been recently described by using a chemoenzymatic method for Fc glycosylation remodeling that takes advantage of the transglycosylation activity of several endoglycosidases and their glycosynthase mutants using glycan oxazolines as their substrates.(34-36) This remodeling approach consists of two steps: trimming off all the heterogeneous N-glycans by an endoglycosidase to leave only the first GlcNAc at the glycosylation site(s) and then adding back a well-defined N-glycan en bloc via an endoglycosidase-catalyzed transglycosylation reaction. (32)

Recent work has demonstrated that IgG-Fc domain glycosylation engineering can be achieved by a combination of yeast or CHO cell expression of the Fc domain and its subsequent chemoenzymatic remodeling through an enzymatic deglycosylation/reglycosylation approach.(34-36) It has been shown that the endo-β-N-acetylglucosaminidase from *Arthrobacter protophormiae*, EndoA, is highly efficient to glycosylate the GlcNAc-containing Fc domain by using various synthetic N-glycan core oxazolines as substrates.(34, 35) Nevertheless, the limitations of the current status of the method are apparent: (a) neither EndoA nor EndoM (another endoglycosidase from *Mucor hiemalis*) was able to transform core-fucosylated IgG-Fc domain,(35) the major glycoforms of recombinant mAbs and IVIG; (b) EndoD mutants were able to attach a Man3GlcNAc core to a fucosylated GlcNAc-Fc domain,(36) but none of EndoD, EndoA, EndoM, and their mutants(36-39) were capable of transferring intact complex type N-glycan to either fucosylated or nonfucosylated GlcNAc-Fc domain; and (c) glycosylation remodeling of intact full-length IgG antibodies with complex type N-glycans is yet to be achieved.

In an attempt to develop efficient enzymatic deglycosylation/glycosylation system for glycoprotein glycosylation remodeling, attention has been turned to EndoS, an endo-β-N-acetylglucosaminidase (ENGase) from *Streptococcus pyogenes* that is capable of hydrolyzing the Fc N-glycans of intact IgG antibodies by cleaving the β-1,4-glycosidic bond in the chitobiose core of the N-glycans.(40-42). Endo-S possesses transglycosylation activity, such as that capable of using Man$_3$GlcNAc oxazoline as donor substrate to glycosylate a GlcNAc acceptor. However, wild type Endo-S also possesses highly active hydrolytic activity, so the glycosylated IgG product is also subject to rapid hydrolysis if wild type Endo-S is used for synthesis and glycosylation remodeling.

In light of the above known activities of Endo S, it would be advantageous to provide a mutant Endo-S that exhibits transglycosylating activity with reduced hydrolyzing activity.

SUMMARY OF THE INVENTION

The present invention provides for recombinant Endo-S and selected mutants thereof that exhibit reduced hydrolysis activity and increased transglycosylation activity for the synthesis of IgG antibodies and Fc fragments thereof, wherein a desired sugar chain is added to a core fucosylated or nonfucosylated GlcNAc-IgG acceptor. As such, the present invention allows for the synthesis and remodeling of therapeutic antibodies and Fc fragments thereof to provide for certain biological activities, such as, prolonged half-life time in vivo, less immunogenicity, enhanced in vivo activity, increased targeting ability, and/or ability to deliver a therapeutic agent.

In one aspect, the present invention provides for transglycosylation activity of an endo-β-N-acetylglucosamindase of *Streptococcus pyogenes* (SEQ ID NO: 1) and mutants thereof, wherein the mutants have at least 95% homology thereto and exhibit transglycosylation activity on both core fucosylated and nonfucosylated GlcNAc-IgG acceptors, wherein the endoglycosidases enable the transfer of an oligosaccharide (in the form of an activated sugar oxazoline) en bloc to a fucosylated or nonfucosylated GlcNAc-IgG (or an Fc fragment thereof) to form a new glycoform of IgG (or an Fc fragment thereof).

In another aspect, the present invention provides for Endo-S mutants that show remarkably enhanced transglycosylation efficiency and diminished or abrogated product hydrolytic activity. Mutants preferably include site-specific mutations including a mutation at Asp-233. The mutants include, but are not limited to, D233Q (SEQ ID NO: 2) and D233A (SEQ ID NO: 3).

In a further aspect, the present invention provides for a chemoenzymatic method for the preparation of a homogeneous core fucosylated or nonfucosylated glycoforms of IgG antibodies, comprising:
a. providing an acceptor selected from the group consisting of a core fucosylated GlcNAc-IgG, nonfucosylated GlcNAc-IgG or corresponding IgG-Fc fragments; and
b. reacting the acceptor with a donor substrate including an activated oligosaccharide moiety, in the presence of *Streptococcus pyogenes* Endo-S Asp-233 mutants to transfer the activated oligosaccharide moiety to the acceptor and yield the homogeneous fucosylated or nonfucosylated glycoprotein.

In a still further aspect, the present invention provides a method for preparing a core-fucosylated IgG or IgG-Fc fragment having a predetermined oligosaccharide moiety, comprising:
a. providing a core-fucosylated IgG acceptor comprising an asparagine-linked core-fucosylated N-acetylglucosamine (GlcNAc) residue; and
b. enzymatically reacting the core-fucosylated IgG acceptor with an activated oligosaccharide donor in the presence of Endoglycosidase-S D233Q (SEQ ID NO: 2) and D233A (SEQ ID NO: 3) mutant, wherein the activated oligosaccharide donor carries an oligosaccharide moiety comprising a predetermined number and type of sugar residues, wherein the oligosaccharide moiety is covalently linked to the core-fucosylated IgG acceptor, thereby preparing the core-fucosylated IgG or IgG-Fc fragment having the predetermined oligosaccharide moiety.

In yet another aspect, the present invention provides for an activated oligosaccharide moiety, such as glycan or oligosaccharide oxazoline, glycosyl fluoride, glycosyl azide or an aryl glycoside, as a donor substrate for the synthesis of homogeneous core-fucosylated glycoproteins or nonfucosylated glycoproteins. Preferably the activated oligosaccharide moiety is an oligosaccharide oxazoline.

In a further aspect, the present invention relates to a chemoenzymatic method for the preparation of a homogeneous fucosylated or nonfucosylated monomer antibody or Fc fragment thereof, said method comprising:
  providing an acceptor selected from core fucosylated or nonfucosylated GlcNAc-antibody or Fc fragment thereof; and
  reacting the acceptor with a donor substrate in the presence a *Streptococcus pyogenes* Endo-S Asp-233 mutant, wherein the donor substrate comprises a predetermined oligosaccharide component with a defined number and type of sugar residues and specific linkage types, thereby providing the homogeneous fucosylated or nonfucosylated monomer antibody or Fc fragment thereof. In one embodiment, a fucosylated GlcNAc containing protein is an alpha-1-6-fucosyl-GlcNAc-protein.

In another aspect, the present invention relates to a method of remodeling an antibody or Fc fragment thereof with an oligosaccharide having a predetermined oligosaccharide component with a defined number and type of sugar residues and with specific linkage types, the method comprising:

a. providing a core fucosylated antibody or Fc fragment thereof comprising Fc N-glycans;
b. treating the core fucosylated antibody or Fc fragment with a hydrolyzing endo-enzyme to yield a Asn-linked GlcNAc moiety; and
c. attaching the oligosaccharide to the Asn-linked GlcNAc moiety in the presence of an Endo-S mutant having an amino acid sequence selected from the group consisting of SEQ ID NO: 2 and SEQ ID NO: 3, thereby adding the predetermined oligosaccharide component.

In a further aspect, the present invention relates to a remodeling method of a core fucosylated or nonfucosylated IgG or IgG-Fc fragment with an oligosaccharide having a predetermined oligosaccharide component with a defined number and type of sugar residues and with specific linkage types, the method comprising:
a. providing a core fucosylated or nonfucosylated IgG or IgG-Fc fragment obtained from natural or recombinant sources carrying heterogeneous N-glycans;
b. treating the natural or recombinant IgG or IgG-Fc fragment with an endo-enzyme (a wild type endoglycosidase or a mutant endoglycosidase with efficient hydrolytic activity) to hydrolyze the bond between the two GlcNAc residues positioned closest to the peptide domain thereby forming a deglycosylated protein carrying a core fucosylated or non-fucosylated GlcNAc-acceptor; and
c. attaching the predetermined oligosaccharide component to the GlcNAc-acceptor to reconstitute the natural beta-1,4-glycosidic bond through transglycosylation with a *Streptococcus pyogenes* Endo-S Asp-233 mutant, thereby adding the predetermined the oligosaccharide component to remodel the core fucosylated or nonfucosylated IgG ro IgG-Fc fragment.

Applicable oligosaccharide oxazolines include, but not limited to, high-mannose type, hybrid type, sialoglycan oxazoline and complex type N-glycan, as well as their selectively modified derivatives such as those with specific tags. Preferably, di-, tri-, tetra-, penta-, hexyl-, hepta-, octyl-, nona-, deca-, or undeca-saccharide oxazolines are utilized as donor substrates for a highly efficient chemoenzymatic synthesis of homogeneous core fucosylated or nonfucosylated IgG antibodies and IgG-Fc fragments.

In yet another aspect, the present invention relates to a method to synthesize a modified antibody or fragment thereof, the method comprising;
a. providing a naturally existing IgG antibody, a recombinant antibody or a Fc domain carrying Fc N-glycans as precursors;
b. Fc deglycosylating using an endoglycosidase such as a wild Endo-S to deglycosylate the Fc domain to form a GlcNAc-acceptor; wherein the GlcNAc-acceptor is positioned on the Fc region of the antibody and the GlcNAc-acceptor is either core fucosylated or nonfucosylated; and
c. transglycosylating the GlcNAc-acceptor in the naturally existing IgG antibody, the recombinant antibody or the Fc domain with an oligosaccharide oxazoline or a sialoglycan oxazoline having a predetermined number of sugar residues under the catalysis of an enzyme selected from the group consisting of Endo-S mutants including SEQ ID NO: 2, and SEQ ID NO: 3 to form the modified antibody with the predetermined number of sugar residues.

In yet another aspect, the present invention provides a method of remodeling an intravenous immunoglobulin (IVIG) exhibiting Fc-sialylated glycoforms, the method comprising:

a. providing an IVIG carrying Fc N-glycans;
b. Fc deglycosylating the Fc N-glycans using an endoglycosidase including wild Endo-S to form GlcNAc-acceptors; wherein the GlcNAc-acceptors are positioned on the Fc region of the IVIG and the GlcNAc-acceptors are either fucosylated or nonfucosylated; and
c. transglycosylating the GlcNAc-acceptors with a sialoglycan oxazoline having a predetermined number of sugar residues under the catalysis of an enzyme selected from the group consisting of Endo-S mutants including SEQ ID NO: 2 and SEQ ID NO: 3 to form a sialylated IVIG.

Another aspect of the present invention provides for an IVIG preparation containing composition comprising at least 90% of homogeneous sialylated Fc glycoforms to increase anti-inflammatory activity, wherein the sialylated Fc glycoforms are synthesized using a *Streptococcus pyogenes* Endo-S Asp-233 mutant in combination with a GlcNAc moiety positioned on the Fc region of a deglycosylated IVIG and a sialoglycan oxazoline having a predetermined number of sugar residues.

In a still further aspect, the present invention relates to a method of synthesizing homogeneous core fucosylated or nonfucosylated IgG antibodies or IgG-Fc fragments, the method comprising:
a. providing a natural or recombinant IgG antibody or IgG-Fc fragment, wherein the recombinant IgG or IgG-Fc is produced from a typical protein expression system, including but not limited to yeast, insect, plant, and any mammalian expression system;
b. removing the N-glycans by an enzyme selected from the group consisting of Endo-H, Endo-A, Endo-S, and/or Endo-F3 to form a core fucosylated or nonfucosylated GlcNAc-containing protein;
c. providing a sugar oxazoline or sialoglycan oxazoline with a desired oligosaccharide component comprising a defined number and type of sugar residues in the chain; and
d. enzymatically transglycosylating the fucosylated or nonfucosylated GlcNAc-containing protein with a sugar oxazoline having a desired number of sugar residues or sialoglycan oxazoline having a desired number of sugar and sialic acid residues with an endoglycosidase selected from the group consisting of a *Streptococcus pyogenes* Endo-S Asp-233 mutants, thereby forming a homogeneous core fucosylated or nonfucosylated IgG antibody or IgG-Fc fragment having an extension of desired number of sugar residues and/or sialic acid.

It is envisioned that the oligosaccharide oxazoline or sialoglycan oxazoline having a predetermined oligosaccharide component with a defined number and type of sugar residues may further comprises an additional moiety or tag including, a therapeutic agent or drug such as for treating cancer, HIV or other viruses, substances that activates receptors on the cell plasma membrane, agents that affects intracellular chemistry, agents that affects cellular physics, genes, gene analogs, RNA, RNA analogs, DNA, DNA analogs, amino acid sequences of surface receptors such as CCR5 or CD4, antigenic structure having affinity for a specific antibody; amino acid sequences of receptor ligands such as gp120, gp41 or gp160, receptor antagonists, receptor blockers, enzymes, enzyme substrates, enzyme inhibitors, enzyme modulators, therapeutic proteins, protein analogs, metabolites, metabolite analogs, oligonucleotides, oligonucleotide analogs, antigens, antigen analogs, antibodies or fragments thereof, antibody analogs, an antibody different from the modified antibody which is reactive to another receptor bacteria, viruses, inorganic ions, metal ions, metal clusters, polymers, fluorescent compounds and any combinations thereof.

As such, the present invention further provides a delivery device for delivering a drug or therapeutic agent having biological activity to treat a condition, the delivery device comprising: a remodeled IgG or IgG-Fc fragment having a predetermined sugar chain or sialoglycan and a therapeutic agent or drug attached to the terminal sugar residue or sialic acid.

The present invention envisions modifying monoclonal antibodies related to HIV including, but not limited to 17b, 48d, A32, C11, 2G12, F240, IgG1b12, 19e, X5, TNX-355 and F91, all of which are commercially available.

Further antibodies related to cancer or other diseases may also be remodeled for individual fit to certain receptors thereby increasing biological activity, the monoclonal antibodies may include, but are not limited to, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101 (Aphton), voloximab (Biogen Idec and PDL BioPharm), Anti-CD80 mAb (Biogen Idec), Anti-CD23 mAb (Biogen Idel), CAT-3888 (Cambridge Antibody Technology), CDP-791 (Imclone), eraptuzumab (Immunomedics), MDX-010 (Medarex and BMS), MDX-060 (Medarex), MDX-070 (Medarex), matuzumab (Merck), CP-675,206 (Pfizer), CAL (Roche), SGN-30 (Seattle Genetics), zanolimumab (Serono and Genmab), adecatumumab (Sereno), oregovomab (United Therapeutics), nimotuzumab (YM Bioscience), ABT-874 (Abbott Laboratories), denosumab (Amgen), AM 108 (Amgen), AMG 714 (Amgen), fontolizumab (Biogen Idec and PDL BioPharm), daclizumab (Biogent Idec and PDL BioPharm), golimumab (Centocor and Schering-Plough), CNTO 1275 (Centocor), ocrelizumab (Genetech and Roche), HuMax-CD20 (Genmab), belimumab (HGS and GSK), epratuzumab (Immunomedics), MLN1202 (Millennium Pharmaceuticals), visilizumab (PDL BioPharm), tocilizumab (Roche), ocrerlizumab (Roche), certolizumab pegol (UCB, formerly Celltech), eculizumab (Alexion Pharmaceuticals), pexelizumab (Alexion Pharmaceuticals and Procter & Gamble), abciximab (Centocor), ranibizimumab (Genetech), mepolizumab (GSK), TNX-355 (Tanox), or MYO-029 (Wyeth).

A still further aspect of the invention relates to a method of remodeling an antibody which initially includes a heterogeneous sugar chain, the method comprising:
a. removing the heterogeneous sugar chain from the antibody with an endoglycosidase to leave a single fucosylated- or nonfucosylated-GlcNAc moiety attached to an original glycosylation site; and
b. transferring a core oligosaccharide or sialoglycan oxazoline with at least one tag to the fucosylated- or -nonfucosylated GlcNAc moiety by an endoglycosidase catalyzed transglycosylation to yield a tagged antibody, wherein the endoglycosidase is selected from the group consisting of Endo-S mutants including SEQ ID NO: 2 and SEQ ID NO: 3.

The tag moiety may include, but is not limited to, antigens, therapeutic drugs such as for cancer or HIV, toxins, fluorescent probes, biotin, PEG species, lipids, or nucleotides.

In another aspect, the present invention provides for a composition comprising at least one *Streptococcus pyogenes* Endo-S Asp-233 mutant selected from the group consisting of D233Q (SEQ ID NO:2) and D233A (SEQ ID No: 3).

In yet another aspect, the present invention provides a substantially homogeneous preparation of core fucosylate or nonfucosylated antibody or Fc fragment thereof having a predetermined oligosaccharide moiety, wherein the substantially homogeneous preparation is produced by any of the aforementioned methods. Also provided are compositions comprising such homogeneous preparations.

In a still further aspect, the present invention provides for a method of treatment using a remodeled antibody having a desired glycosylation state and/or sialylated form in an amount sufficient to modulate biological activity in the treated subject.

Other aspects, features and embodiments of the invention will be more fully apparent from the ensuing disclosure and appended claims.

BRIEF DESCRIPTION OF THE FIGURES

FIG. 2 shows the sequence alignment of EndoS (SEQ ID NO: 4) and EndoF3 (SEQ ID NO: 5).

FIG. 3 B shows the scheme for glycosylation remodeling of rituximab to selectively modified glycoforms (▓ GlcNAc; ● Man; ◐ Gal; ○ Glc; ▲ Fuc; ◆ Sia).

FIG. 5 B shows the enzymatic remodeling to non-fucosylated homogeneous glycoform of rituximab (■ GlcNAc; ● Man; ◐ Gal; ○ Glc; ▲ Fuc; ◆ Sia).

FIG. 8a shows the fluorescent HPLC profiles of 2AB-labeled N-glycans from Fab and Fc of IVIG from native IVIG Fc. The glycan structures include the following components: (■ GlcNAc; ● Man; ◐ Gal; ○ Glc; ▲ Fuc; ◆ Sia).

FIG. 8b shows the fluorescent HPLC profiles of 2AB-labeled N-glycans from Fab and Fc of IVIG from glycoengineered IVIG Fc. The glycan structures include the following components: (■ GlcNAc; ● Man; ◐ Gal; ○ Glc; ▲ Fuc; ◆ Sia).

FIG. 8c shows the fluorescent HPLC profiles of 2AB-labeled N-glycans from Fab and Fc of IVIG from native IVIG Fab. The glycan structures include the following components: (■ GlcNAc; ● Man; ◐ Gal; ○ Glc; ▲ Fuc; ◆ Sia).

FIG. 8d shows the fluorescent HPLC profiles of 2AB-labeled N-glycans from Fab and Fc of IVIG from glycoengineered IVIG Fab. The glycan structures include the following components: (■ GlcNAc; ● Man; ◐ Gal; ○ Glc; ▲ Fuc; ◆ Sia).

FIG. 9 B shows typical SPR sensorgrams of the binding of G2-rituximab and commercial rituximab with FcγRIIIa-F158. The antibodies were immobilized by Protein A capture and the binding was analyzed by injecting the respective Fcγ receptors at a serial 2-fold dilutions starting at 40 μg/mL (1.33 uM).

FIG. 9 C shows typical SPR sensorgrams of the binding of G2-rituximab and commercial rituximab with FcγRIIb. The antibodies were immobilized by Protein A capture and the binding was analyzed by injecting the respective Fcγ receptors at a serial 2-fold dilutions starting at 40 μg/mL (1.33 uM).

FIG. 12 B shows the ESI-MS of the light chain of rituximab.

FIG. 12 C shows the ESI-MS of the deconvoluted MS of the light chain of rituximab.

FIG. 12 D shows the ESI-MS of the heavy chain of rituximab.

FIG. 12 E shows the ESI-MS of the deconvoluted MS of the heavy chain of rituximab.

FIG. 15 B shows the LC-MS monitoring on defucosylation of Fuc(α2,6)GlcNAc-rituximab (1) with bovine kidney α-fucosidase. The deconvoluted ESI-MS profiles of the rituximab's heavy chain were shown (FG-Rx, heavy chain of Fuc(α2,6)GlcNAc-rituximab; G-Rx, heavy chain of GlcNAc-rituximab) following incubation with the α-fucosidase for 7 days.

FIG. 15 C shows the LC-MS monitoring on defucosylation of Fuc(α2,6)GlcNAc-rituximab (1) with bovine kidney α-fucosidase. The deconvoluted ESI-MS profiles of the rituximab's heavy chain were shown (FG-Rx, heavy chain of Fuc(α2,6)GlcNAc-rituximab; G-Rx, heavy chain of GlcNAc-rituximab) following incubation with the α-fucosidase for 14 days.

FIG. 15 D shows the LC-MS monitoring on defucosylation of Fuc(α2,6)GlcNAc-rituximab (1) with bovine kidney α-fucosidase. The deconvoluted ESI-MS profiles of the rituximab's heavy chain were shown (FG-Rx, heavy chain of Fuc(α2,6)GlcNAc-rituximab; G-Rx, heavy chain of GlcNAc-rituximab) following incubation with the α-fucosidase for 20 days.

FIG. 17 A shows the amino acid residues of Streptococcus pyogenes Endo-S Asp-233 mutant D233Q (SEQ ID NO:2).

FIG. 17 B shows the amino acid residues of Streptococcus pyogenes Endo-S Asp-233 mutant D233A (SEQ ID No: 3).

DETAILED DESCRIPTION OF THE INVENTION

Figure 1B:
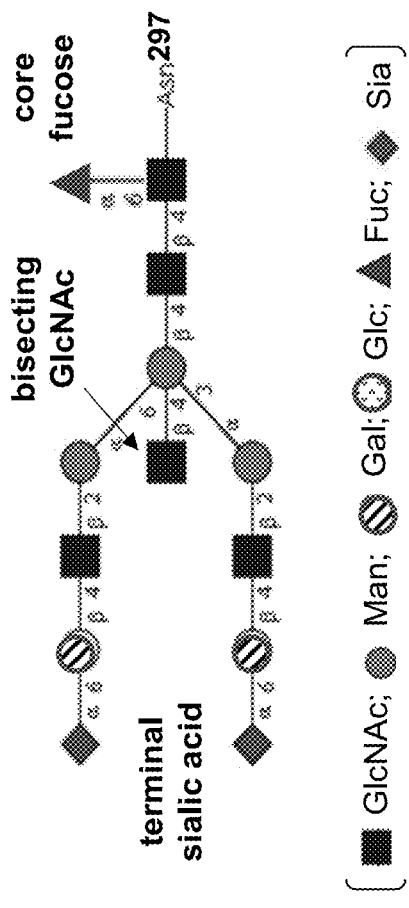
FIG. 1b shows the structure of a full-length bi-antennary complex type N-glycan attached to the Asn-297 in the Fc domain, (▓ GlcNAc; ● Man; ◐ Gal; ○ Glc; ▲ Fuc; ◆ Sia).
Figure 1A:
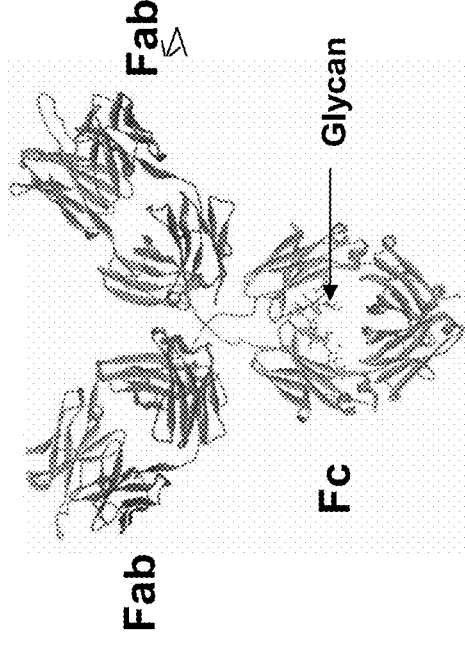
FIG. 1a shows the alpha backbone structure of human IgG showing functional regions (modeled on the basis of PDB code 1HZH). (▓ GlcNAc; ● Man; ◐ Gal; ○ Glc; ▲ Fuc; ◆ Sia).

The present invention provides for novel glycosynthase EndoS Asp 233 mutants that show remarkable transglycosylation efficiency capable of transferring complex type N-glycans from activated glycan oxazolines to deglycosylated intact antibodies without product hydrolysis. It has been found herein that the glycosynthase EndoS Asp 233 mutants acted efficiently on both core fucosylated and nonfucosylated GlcNAc-Fc domain of intact antibodies to provide various defined IgG glycoforms. Further, antibodies and intravenous immunoglobulins were transformed into Fc fully sialylated glycoforms having increased anti-inflammatory activity. Still further, the present invention provides for a homogeneous glycoform having increased ADCC activity with enhanced FcγIIIa receptor-binding activity and azido-tagged glycoforms that can be further transformed into other glycoforms.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

It is understood that aspects of the present invention described herein include "consisting" and/or "consisting essentially of" aspects.

Definitions

As used in the specification herein, "a" or "an" may mean one or more. As used herein in the claim(s), when used in conjunction with the word "comprising", the words "a" or "an" may mean one or more than one. As used herein "another" may mean at least a second or more.

As used herein, "biological activity" refers to pharmacodynamic and pharmacokinetic properties including, for example, molecular affinity or resultant biochemical or physiological effect, receptor affinity or resultant biochemical or physiological effect, non-receptor affinity or biochemical or physiological effect, efficacy, bioavailability, absorption, distribution, metabolism, or elimination.

As used herein, "sugar" refers to an oxidized or nonoxidized carbohydrate-containing molecule, including, but not limited to, a monosaccharide, disaccharide, trisaccharide, oligosaccharide, or polysaccharide, including, for example, N-acetylglucosamine, mannose, galactose, N-acetylneuraminic acid (sialic acid), glucose, fructose, fucose, sorbose, rhamnose, mannoheptulose, N-acetylgalactosamine, dihydroxyacetone, xylose, xylulose, arabinose, glyceraldehyde, sucrose, lactose, maltose, trehalose, cellobiose or any combination thereof of the L- or D-isomer. Sugar further refers to, such molecules produced naturally, recombinantly, synthetically, and/or semi-synthetically.

As used herein, "homogenous" refers to core fucosylated glycoproteins or nonfucosylated glycoproteins wherein the oligosaccharide component comprises at least 75%, more preferably at least 80%, at least 85% or at least 90%, and most preferably at least 95% of the same number and types of sugar residues.

As used herein, "protein" or "glycoprotein" is interchangeable with the terms peptide and glycopeptide.

As used herein, "homology" refers to amino acid sequence having substantial identity or similarity between two polypeptides and having at least 90%, and more preferably at least 95% similarity to a reference polypeptide. For polypeptides, the length of comparison to obtain the above-described percent homologies between sequences will generally be at least 25 amino acids, alternatively at least 50 amino acids, more likely at least 100 amino acids, and most likely 200 amino acids or more. Substantially identity or homologous polypeptides include additions, truncations, internal deletions or insertions, conservative and non-conservative substitutions, or other modifications located at positions of the amino acid sequence which do not destroy the function of the endoglycosidase. Those of skill in the art will recognize the numerous amino acids that can be modified or substituted with other chemically similar residues without substantially altering activity.

As used herein, "modulates" refers to an increase or decrease in "biological activity", as defined above, when comparing to a glycosylation-engineered antibody of the present invention to a non-glycosylation-engineered antibody.

As used herein, "immunoglobulin molecule" or "antibodies," refers to molecules that contain an antigen binding site which specifically binds an antigen or an Fc region that binds to cell receptors. Structurally, the simplest naturally occurring antibody (e.g., IgG) comprises four polypeptide chains, two heavy (H) chains and two light (L) chains inter-connected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including Fc fragment(s).

Antibodies can be fragmented using conventional techniques as described herein and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab and Fc fragments can be prepared by proteolytic digestion of substantially intact immunoglobulin molecules with papain using methods that are well known in the art. However, a Fab or Fc fragment may also be prepared by expressing in a suitable host cell the desired portions of immunoglobulin heavy chain and immunoglobulin light chain using methods known in the art.

As used herein, with respect to antibodies, "substantially pure" means separated from those contaminants that accompany it in its natural state or those contaminants generated or used in the process of the obtaining the antibody. This term further includes the desired product having a single glycosylation state, whether or not this state includes glycosylation at a single site or multiple sites. Typically, the antibody is substantially pure when it constitutes at least 60%, by weight, of the antibody in the preparation. For example, the antibody in the preparation is at least about 75%, in certain embodiments at least about 80%, in certain embodiments at about 85%, in certain embodiments at least about 90%, in certain embodiments at least about 95%, and most preferably at least about 99%, by weight, of the desired antibody. A substantially pure antibody includes a naturally, recombinantly, or synthetically produced antibody.

As used herein, "therapeutically effective amount" refers to an amount that results in an improvement or remediation of the symptoms of the disease or condition.

Antigens useful for attachment as a tag to a modified core fucosylated or nonfucosylated glycoprotein of the present invention and more preferably an antibody or fragment thereof may be a foreign antigen, an endogenous antigen, fragments thereof, or variants having the same functional activity.

As used herein, "endogenous antigen" refers to a protein or part thereof that is naturally present in the recipient animal cell or tissue, such as a cellular protein, an immunoregulatory agent, or a therapeutic agent.

As used herein, "foreign antigen" refers to a protein or fragment thereof, which is foreign to the recipient animal cell or tissue including, but not limited to, a viral protein, a parasite protein, an immunoregulatory agent, or a therapeutic agent.

The foreign antigen may be a protein, an antigenic fragment or antigenic fragments thereof that originate from viral and parasitic pathogens.

Alternatively, the foreign antigen may be encoded by a synthetic gene and may be constructed using conventional recombinant DNA methods; the synthetic gene may express antigens or parts thereof that originate from viral and parasitic pathogens. These pathogens can be infectious in humans, domestic animals or wild animal hosts.

The foreign antigen can be any molecule that is expressed by any viral or parasitic pathogen prior to or during entry into, colonization of, or replication in their animal host.

The viral pathogens, from which the viral antigens are derived include, but are not limited to, Orthomyxoviruses, such as influenza virus (Taxonomy ID: 59771); Retroviruses, such as RSV, HTLV-1 (Taxonomy ID: 39015) and HTLV-II (Taxonomy ID: 11909); Herpes viruses, such as EBV (Taxonomy ID: 10295), CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia Taxonomy ID: 10245); Rotavirus Taxonomy ID: 10912); and Parvoviruses, such as adeno-associated virus 1 (Taxonomy ID: 85106).

Examples of viral antigens include, but are not limited to, the human immunodeficiency virus antigens Nef (National Institute of Allergy and Infectious Disease HIV Repository Cat. #183; GenBank accession #AF238278), Gag, Env (National Institute of Allergy and Infectious Disease HIV Repository Cat. #2433; GenBank accession #U39362), Tat (National Institute of Allergy and Infectious Disease HIV Repository Cat. #827; GenBank accession #M13137), Rev (National Institute of Allergy and Infectious Disease HIV Repository Cat. #2088; GenBank accession #L14572), Pol (National Institute of Allergy and Infectious Disease HIV Repository Cat. #238; GenBank accession #AJ237568) and T cell and B cell epitopes of gp120; the hepatitis B surface antigen (GenBank accession #AF043578); rotavirus antigens, such as VP4 (GenBank accession #AJ293721) and VP7 (GenBank accession #AY003871); influenza virus antigens, such as hemagglutinin (GenBank accession #AJ404627); nucleoprotein (GenBank accession #AJ289872); and herpes simplex virus antigens, such as thymidine kinase (GenBank accession #AB047378).

The bacterial pathogens, from which the bacterial antigens are derived, include but are not limited to, *Mycobacterium* spp., *Helicobacter pylori*, *Salmonella* spp., *Shigella* spp., *E. coli*, *Rickettsia* spp., *Listeria* spp., *Legionella pneumoniae*, *Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of *Borellia burgdorferi*, protective paracrystalline-surface-layer proteins of *Rickettsia prowazekii* and *Rickettsia typhi*, the listeriolysin (also known as "Llo" and "Hly") and/or the superoxide dismutase (also know as "SOD" and "p60") of *Listeria monocytogenes*; the urease of *Helicobacter pylori*, and the receptor-binding domain of lethal toxin and/or the protective antigen of *Bacillus* anthrax.

Example of antigens from biological weapons or pathogens include, but are not limited to, smallpox, anthrax, tularemia, plague, *listeria*, brucellosis, hepatitis, vaccinia, mycobacteria, coxsackievirus, tuberculosis, malaria, erhlichosis and bacterial meningitis.

The parasitic pathogens, from which the parasitic antigens are derived, include but are not limited to, *Plasmodium* spp., such as *Plasmodium falciparum* (ATCC #: 30145); Trypanosome spp., such as *Trypanosoma cruzi* (ATCC #: 50797); Giardia spp., such as Giardia intestinalis (ATCC #: 30888D); *Boophilus* spp.; *Babesia* spp., such as *Babesia microti* (ATCC #: 30221); *Entamoeba* spp., such as *Entamoeba histolytica* (ATCC #: 30015); *Eimeria* spp., such as *Eimeria maxima* (ATCC #40357); *Leishmania* spp., (Taxonomy ID: 38568); Schistosome spp., such as *Schistosoma mansoni* (GenBank accession #AZ301495); *Brugia* spp., such as *Brugia malayi* (GenBank accession #BE352806); Fascida spp., such as *Fasciola hepatica* (GenBank accession #AF286903); *Dirofilaria* spp., such as *Dirofilaria immitis* (GenBank accession #AF008300); *Wuchereria* spp., such as *Wuchereria bancrofti* (GenBank accession #AF250996); and *Onchocerea* spp; such as *Onchocerca volvulus* (GenBank accession #BE588251).

Examples of parasite antigens include, but are not limited to, the pre-erythrocytic stage antigens of *Plasmodium* spp. such as the circumsporozoite antigen of *P. falciparum* (GenBank accession #M22982) *P vivax* (GenBank accession #M20670); the liver stage antigens of *Plasmodium* spp, such as the liver stage antigen 1 (as referred to as LSA-1; GenBank accession #AF086802); the merozoite stage antigens of *Plasmodium* spp; such as the merozoite surface antigen-1 (also referred to as MSA-1 or MSP-1; GenBank accession #AF199410); the surface antigens of *Entamoeba histolytica*, such as the galactose specific lectin (GenBank accession #M59850) or the serine rich *Entamoeba histolytica* protein; the surface proteins of *Leishmania* spp, such as 63 kDa glycoprotein (gp63) of *Leishmania major* (GenBank accession #Y00647 or the 46 kDa glycoprotein (gp46) of *Leishmania major*; paramyosin of *Brugia malayi* (GenBank accession #U77590; the triose-phosphate isomerase of *Schistosoma mansoni* (GenBank accession #W06781; the secreted globin-like protein of *Trichostrongylus colubriformis* (GenBank accession #M63263; the glutathione-S-transferases of *Fasciola hepatica* (GenBank accession #M77682; *Schistosoma bovis* (GenBank accession #M77682); *S. japonicum* (GenBank accession #U58012; and KLH of *Schistosoma bovis* and *S. japonicum* (Bashir, et al., supra).

Examples of tumor specific antigens include prostate specific antigen (PSA), TAG-72 and CEA; human tyrosinase (GenBank accession #M27160); tyrosinase-related protein (also referred to as TRP; GenBank accession #AJ132933); and tumor-specific peptide antigens.

Examples of transplant antigens include the CD3 molecule on T cells and histocompatibility antigens such as HLA A, HLA B, HLA C, HLA DR and HLA.

Examples of autoimmune antigens include IAS 13 chain, which is useful in therapeutic vaccines against autoimmune encephalomyelitis (GenBank accession #D88762); glatamic acid decarboxylase, which is useful in therapeutic vaccines against insulin-dependent type 1 diabetes (GenBank accession #NM013445); thyrotropin receptor (TSHr), which is useful in therapeutic vaccines against Grave's disease (GenBank accession #NM000369) and tyrosinase-related protein 1, which is useful in therapeutic vaccines against vitiligo (GenBank accession #NM000550).

HIV drugs that may be used in the construction of the tagged antibodies or fragments thereof include, but are not limited to antiviral agents such as nucleoside RT inhibitors, CCR5 inhibitors/antagonists, viral entry inhibitors and their functional analogs. Specifically, an antiviral agent may nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies; and viral entry inhibitors, such as Fuzeon (T-20) (enfuvirtide), NB-2, NB-64, T-649, T-1249, SCH-C, SCH-D, PRO 140, TAK 779, TAK-220, RANTES analogs, AK602, UK-427, 857; and functional analogs or equivalents thereof.

It is envisioned that many different core fucosylated glycoproteins and nonfucosylated glycoproteins can be modified according to the methods of the present invention or used as a therapeutic agent for conjugation to a terminal sugar including but not limited to, adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives; bombesin; bone morphogenic factor (BMP); bone morphogenic protein; bradykinin; caerulein; calcitonin gene related polypeptide (CGRP); calcitonins; CCK-8; cell growth factors (e.g., EGF; TGF-alpha; TGF-beta; PDGF; acidic FGF; basic FGF); cerulein; chemokines; cholecystokinin; cholecystokinin-8; cholecystokinin-pancreozymin (CCK-PZ); colistin; colony-stimulating factors (e.g. CSF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides; endotherins; enkephalins; enkephalin derivatives; epidermal growth factor (EGF); erythropoietin (EPO); follicle-stimulating hormone (FSH); gallanin; gastric inhibitory polypeptide; gastrin-releasing polypeptide (GRP); gastrins; G-CSF; glucagon; glutathione peroxidase; glutathio-peroxidase; gonadotropins (e.g., human chorionic gonadotrophin and .alpha. and .beta. subunits thereof); gramicidin; gramicidines; growth factor (EGF); growth hormone-releasing factor (GRF); growth hormones; hormone releasing hormone (LHRH); human artrial natriuretic polypeptide (h-ANP); human placental lactogen; insulin; insulin-like growth factors (IGF-I; IGF-II); interferon; interferons (e.g., alpha-beta- and gamma-interferons); interleukins (e.g. 1; 2; 3; 4; 5; 6; 7; 8; 9; 10; 11 and 12); intestinal polypeptide (VIP); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyldipeptide; nerve growth factor (NGF); nerve nutrition factors (e.g. NT-3; NT-4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor; somatomedins; somatostatins derivatives; superoxide dismutase; taftsin; tetragastrin; thrombopoietin (TPO); thymic humoral factor (THF); thymopoietin; thymosin; thymostimulin; thyroid hormone releasing hormone; thyroid-stimulating hormone (TSH); thyrotropin releasing hormone TRH); trypsin; tuftsin; tumor growth factor (TGF-alpha); tumor necrosis factor (TNF); tyrocidin; urogastrone; urokinase; vasoactive intestinal polypeptide; and vasopressin.

Core fucosylated and nonfucosylated glycoproteins are important classes of biomolecules that play crucial roles in many biological events such as cell adhesion, tumor metastasis, pathogen infection, and immune response. As indicated previously herein, a major problem in structural and functional studies of fucosylated or nonfucosylated glycoproteins is their structural microheterogeneity. Natural and recombinant fucosylated or nonfucosylated glycoproteins are typically produced as a mixture of glycoforms that differ only in the structure of the pendent oligosaccharides.

The remodeled glycoproteins, such as antibodies can be subjected to any further structural modifications that are necessary or desired, including, without limitation, glycosyl transfer, and selective ligation (e.g., click chemistry, Staudinger reaction, etc.) to introduce the additional functional groups or tags. The functional groups can be of any suitable type, including, without limitation, toxins, special antigens (such as alpha-Gal), radioactive species, photoactive species, PEGs, etc. The glycoprotein can be catalytically reacted in a "click chemistry" cycloaddition reaction of the azide functionality of the glycoprotein with an alkyne bearing the functional moiety of interest. The azido and alkyne functional groups can be switched in the respective ligation components, and the glycoprotein can be functionalized with an alkynyl functionality and reacted with an azide-functionalized compound including the moiety of interest. It will also be appreciated that other ligation pairs can be devised for the click chemistry reaction.

The core fucosylated and nonfucosylated antibodies or fragments thereof, produced according to the methods described herein, can be used for diagnosis and therapeutics. Approximately two-thirds of therapeutic proteins, such as monoclonal antibodies used on the market and/or currently in clinical trials are glycoproteins. However, the structural heterogeneity in different glycoforms of natural and recombinant glycoproteins presents a major barrier in developing glycoprotein-based drugs, as different glycoforms may have different biological activities and controlling glycosylation to a homogeneous glycoform is extremely difficult during expression. The previous discovery of the transglycosylation activity of a class of endoglycosidases represents a major advance in the field for glycosylation engineering to enhance glycoproteins' therapeutic and diagnostic potentials and the Endo-S mutants of the present invention are able to transglycosylate core fucosylated and nonfucosylated natural and recombinant glycoproteins without the the negative aspects of hydrolysis.

The features and advantages of the present invention are more fully shown by the following non-limiting examples.

EXAMPLES

Generation of EndoS Glycosynthase Mutants and Their Use for Glycosylation Remodeling of Intact Monoclonal Antibody Rituximab Glycosynthases have been previously made from several GH85 endoglycosidases (ENGases), including EndoA, EndoM, and EndoD, by site-directed mutagenesis of a key asparagine (Asn) residue responsible for promoting oxazolinium ion intermediate formation during hydrolysis.(36-39, 43) EndoS is an endoglycosidase belonging to the glycoside hydrolase family 18 (GH18),(40, 41) which is in the same GH family as EndoF1, EndoF2, and EndoF3 that were recently shown to have transglycosylation activity.(44) Based on the assumption that EndoS-catalyzed hydrolysis also proceeds by a substrate-assisted mechanism involving the formation of an oxazolinium ion intermediate, as demonstrated by other GH18 endoglycosidases such as EndoF3, (45) potential glycosynthases from EndoS were created by identifying and mutating the residue responsible for promoting oxazolinium ion formation. Previous structural and mutagenesis studies on EndoF3 have shown that an aspartic acid residue at position 165 (D165), instead of an asparagine residue as in the family GH85 enzymes, is responsible for promoting oxazoline formation and that the E167 residue is the general acid/base for catalytic hydrolysis.(45) Sequence alignment of EndoS with EndoF3 (FIG. 2) led to the identification of two key residues in EndoS for catalysis: the D233 residue (corresponding to D165 in EndoF3) responsible for promoting oxazolinium ion formation and the E235 residue (equivalent to E167 of EndoF3) as the general acid/base residue in glycan hydrolysis as shown in FIG. 2. Functionally, the D233 residue should be also equivalent to the N171, N175, and N322 in the GH85 endoglycosidases, EndoA, EndoM, and EndoD, respectively. Thus, following the approach to creating glycosynthases from EndoA, EndoM, and EndoD that proceed in a substrate-assisted mechanism via an oxazolinium ion intermediate,(36-39) two specific mutants, D233A (SEQ ID NO: 2) and D233Q (SEQ ID NO: 3), as shown in FIGS. 17A-17B, were generated by site-directed mutagenesis of EndoS (SEQ ID NO:1). These mutants, as well as the wild-type EndoS, were expressed in *Escherichia coli* in high yield (30-40 mg/L) as a GST fusion protein and purified by glutathione affinity chromatography.

Figure 3A:
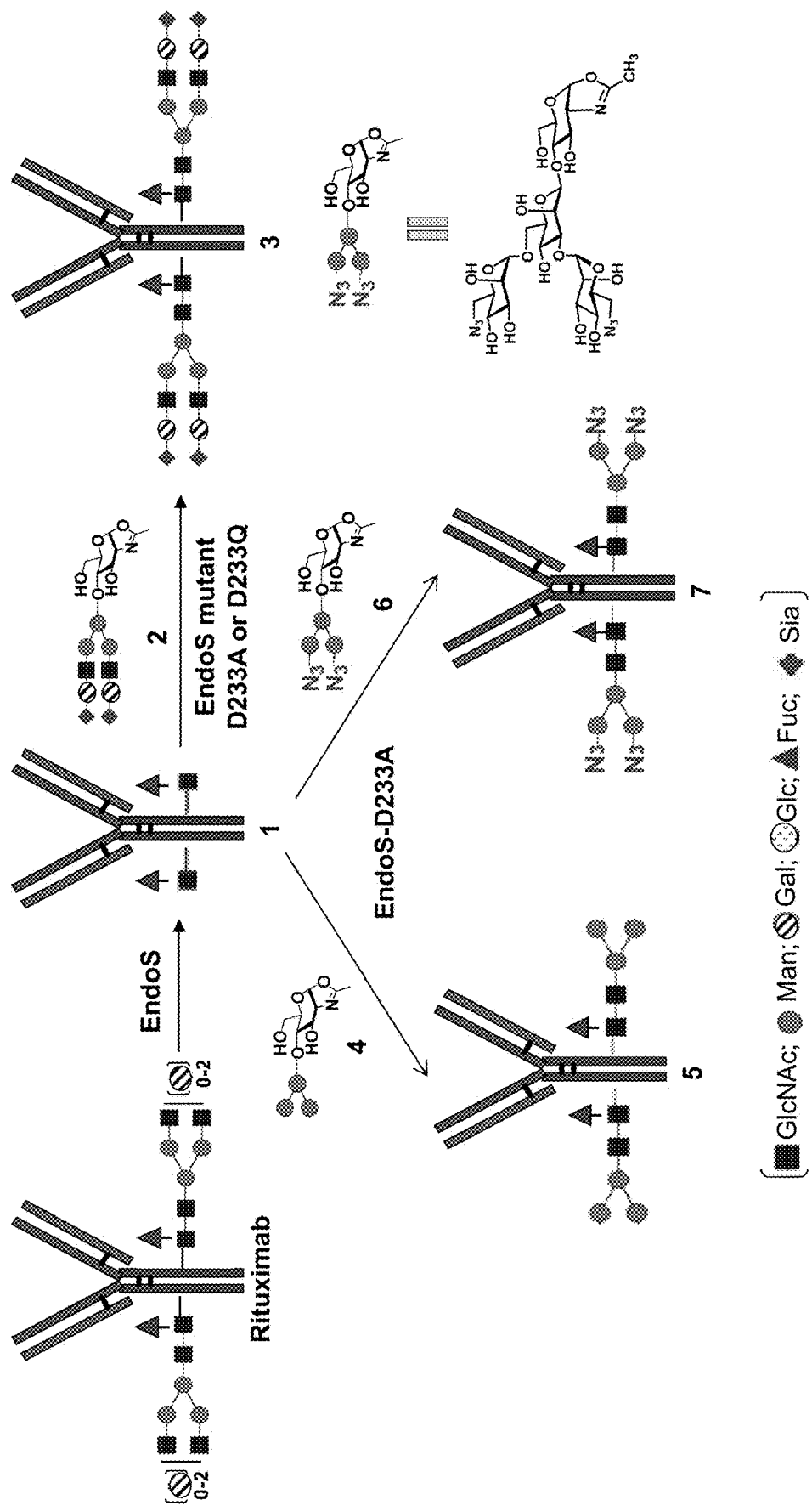
FIG. 3 A shows the scheme for glycosylation remodeling of rituximab to homogeneous natural glycoforms (▓ GlcNAc; ● Man; ◐ Gal; ○ Glc; ▲ Fuc; ◆ Sia).
Figure 3B:
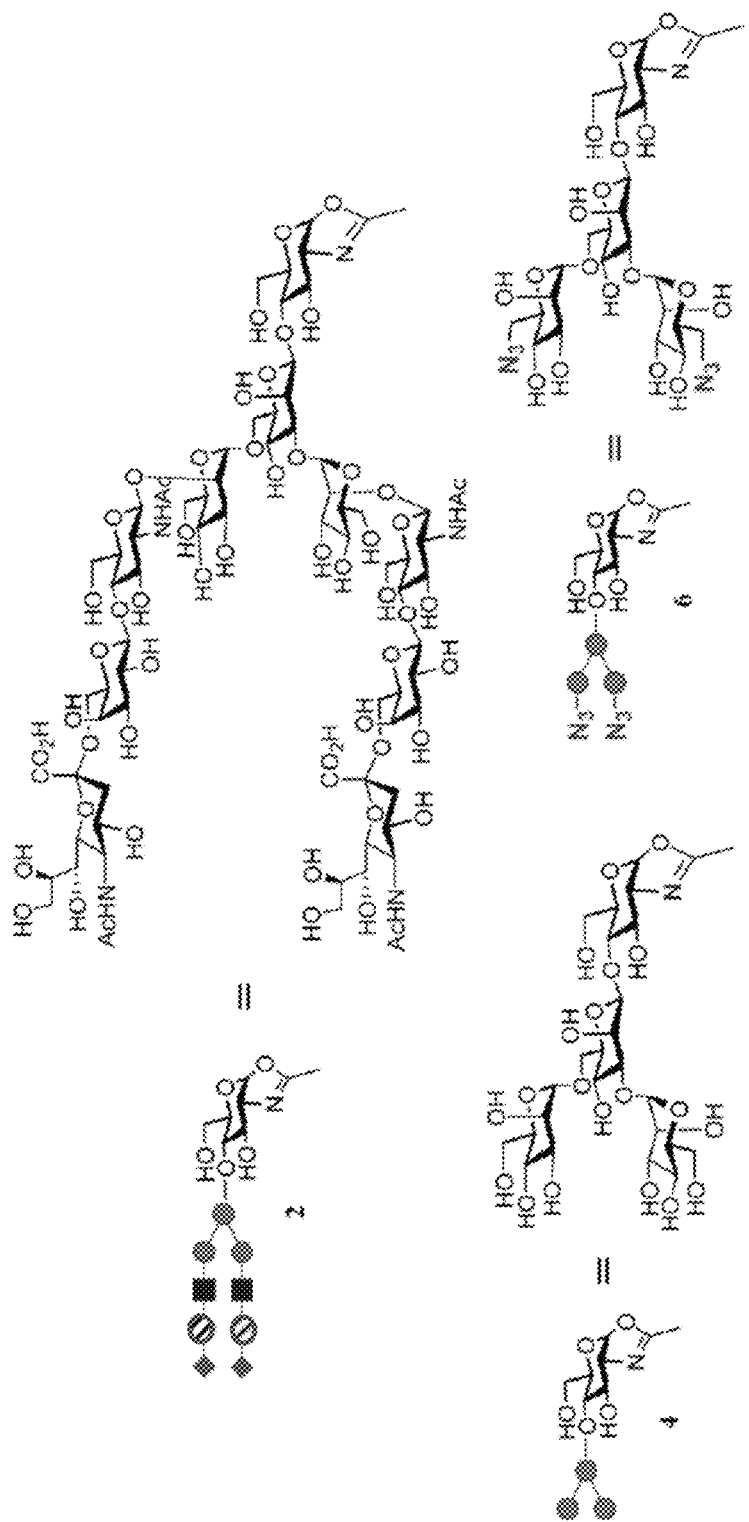
Figure 4B:
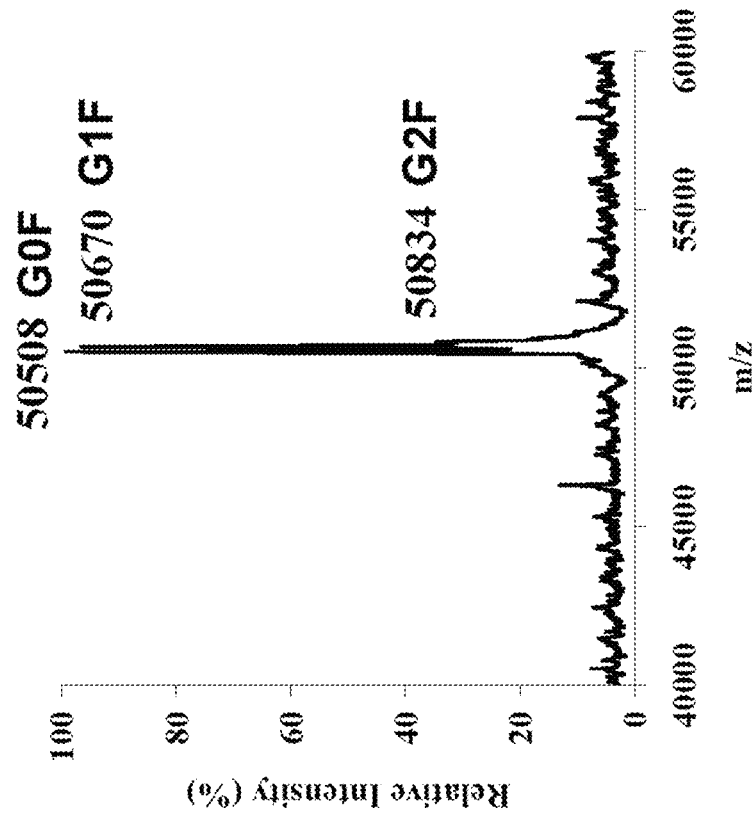
FIG. 4B shows the ESI-MS (after deconvolution) analysis of the heavy chain of the commercial rituximab.
Figure 4A:
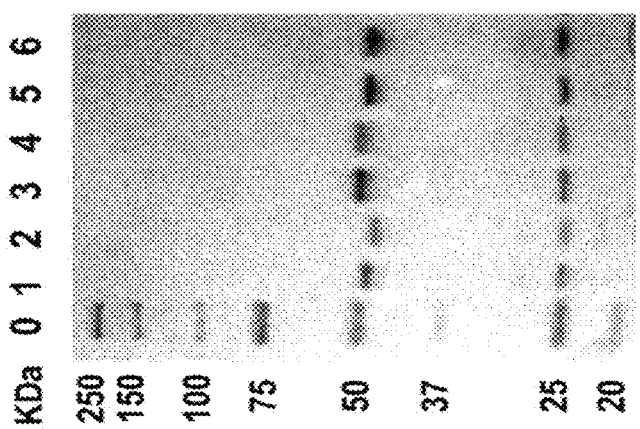
FIG. 4A shows the SDS-PAGE analysis of the glycosylation remodeling of rituximab: Lane 0, protein markers; Lane 1, commercial rituximab; Lane 2, EndoS de-glycosylated rituximab (1); Lane 3, transglycosylation product (3) from the EndoS-D233A catalyzed reaction between (1) and sialoglycan oxazoline (2); Lane 4, transglycosylation product from the EndoS-D233Q catalyzed reaction of (1) and (2); lane 5, the transglycosylation product (5) from the EndoS-D233Q catalyzed reaction between the deglycosylated rituximab (1) and Man3GlcNAc oxazoline (4); lane 6, the transglycosylation product (7) from the EndoS-D233Q catalyzed reaction between the deglycosylated rituximab (1) and N3Man3GlcNAc oxazoline (6).
Figure 10:
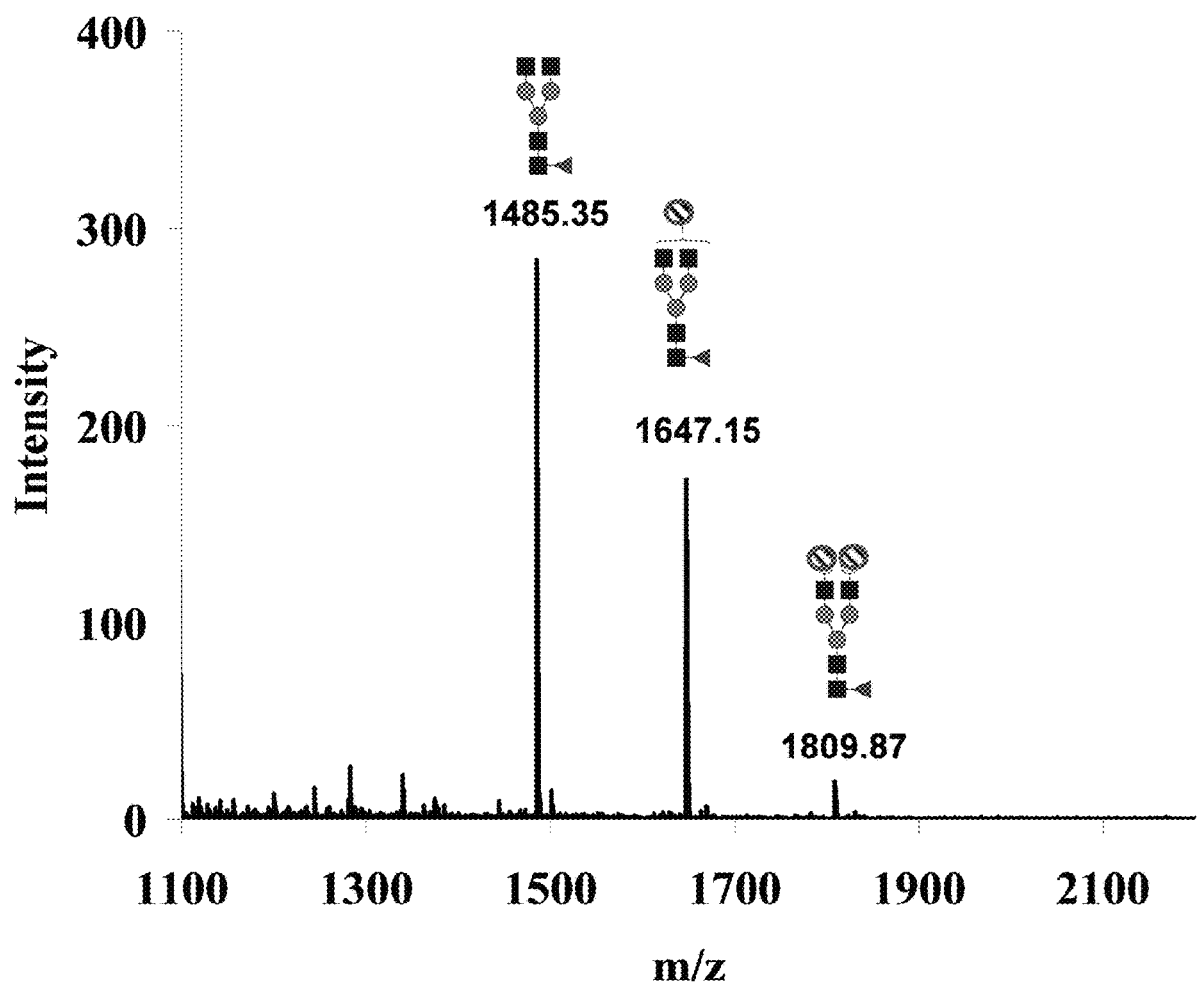
FIG. 10 shows the MALDI-TOF MS of the Fc N-glycans released by PNGase F treatment with the same symbols as defined in FIG. 1.
Figure 11:
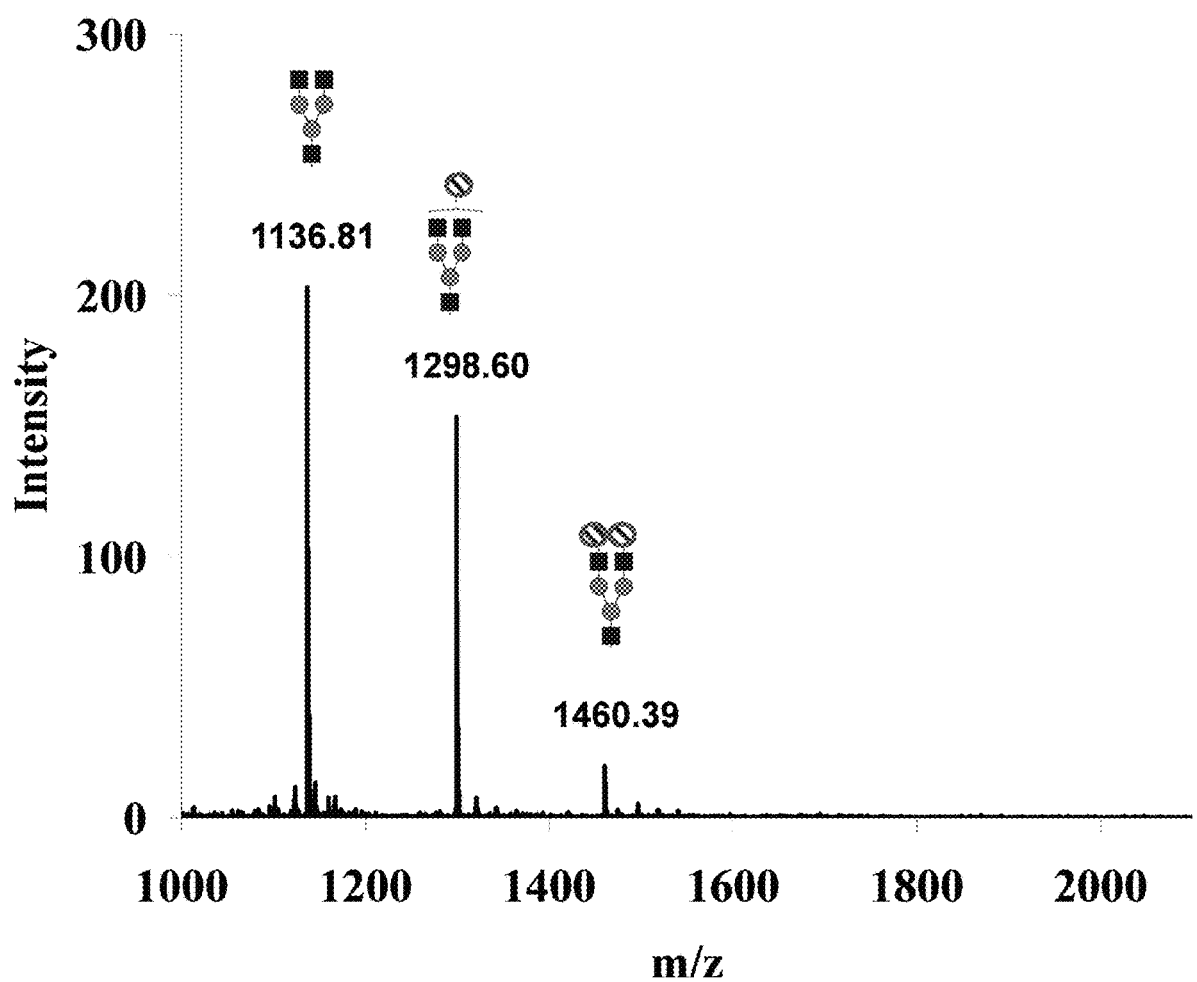
FIG. 11 shows the MALDI-TOF MS of the Fc N-glycans released by EndoS treatment with the same symbols as defined in FIG. 1.
Figure 12:
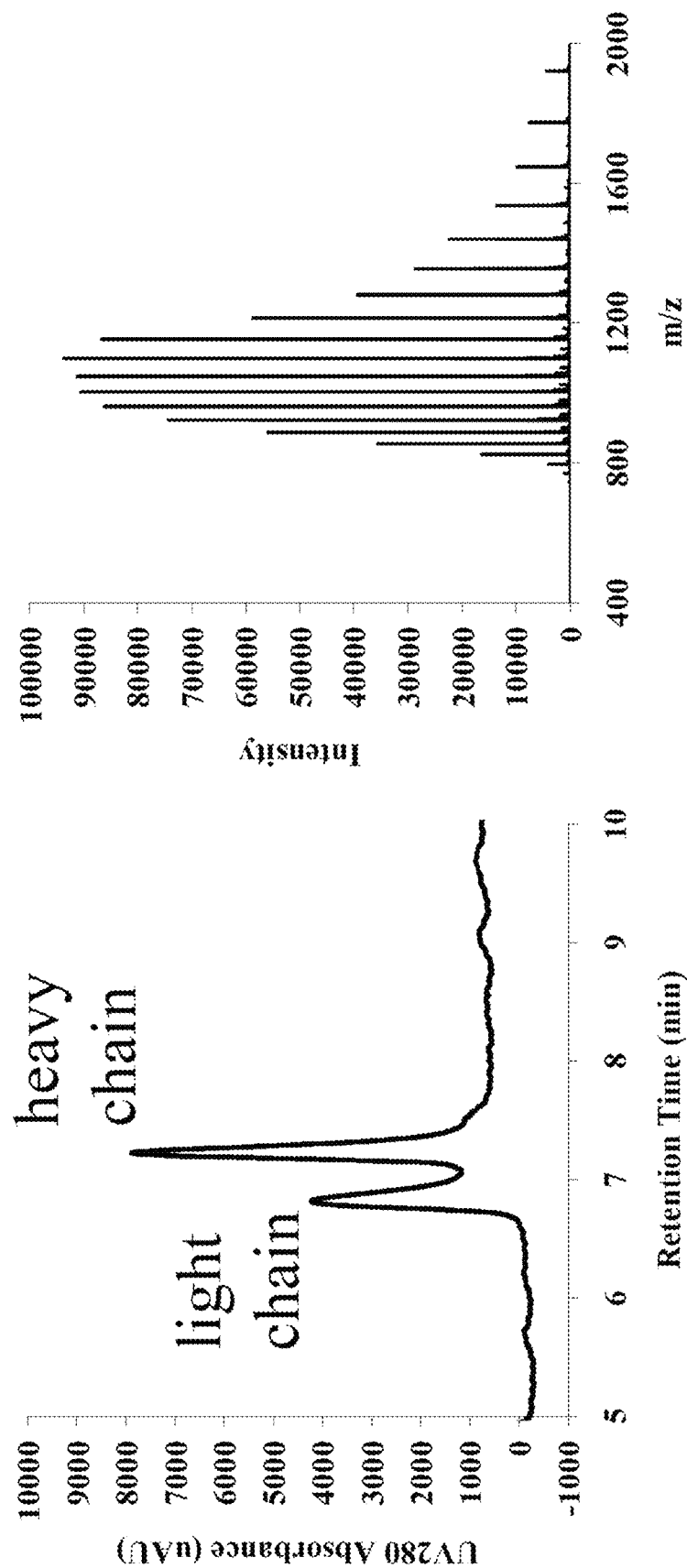
FIG. 12 A shows the LC-MS profile of reduced rituximab.
Figure 12:
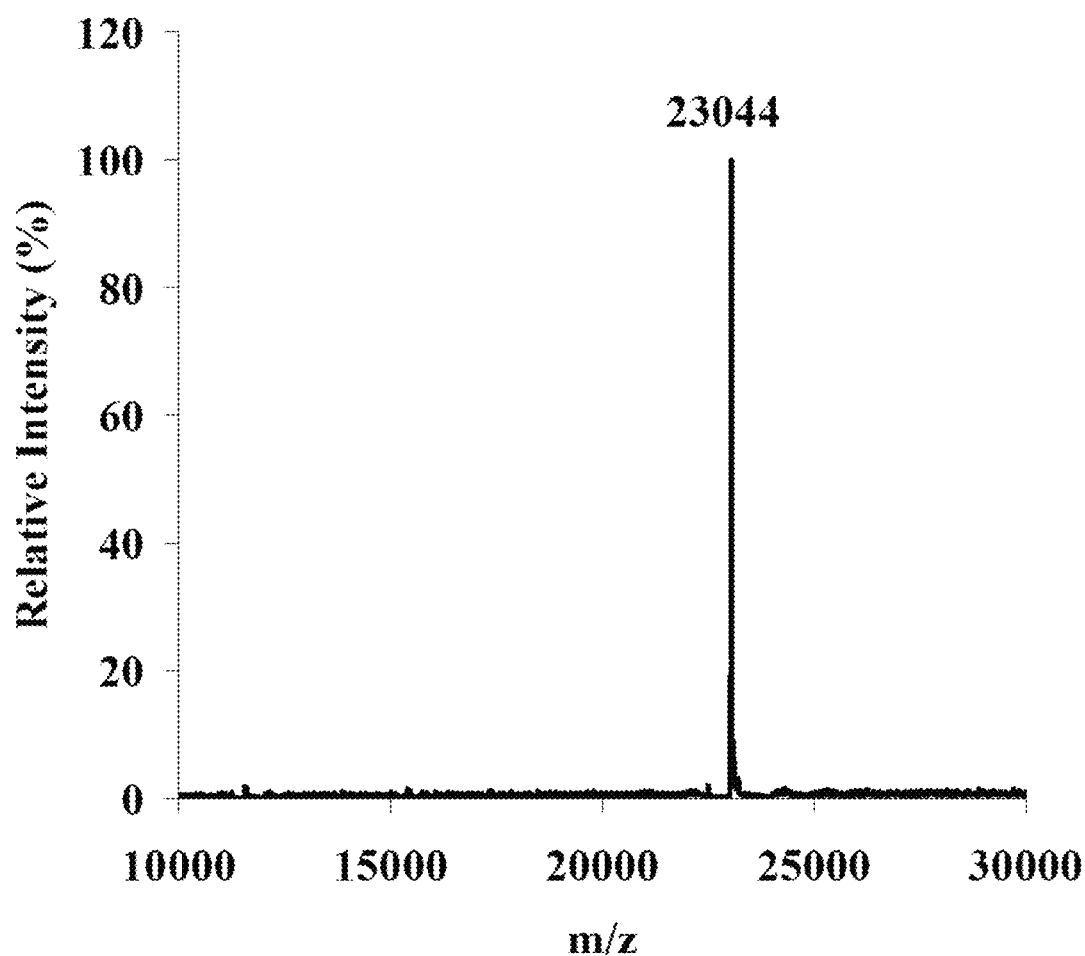
Figure 12:
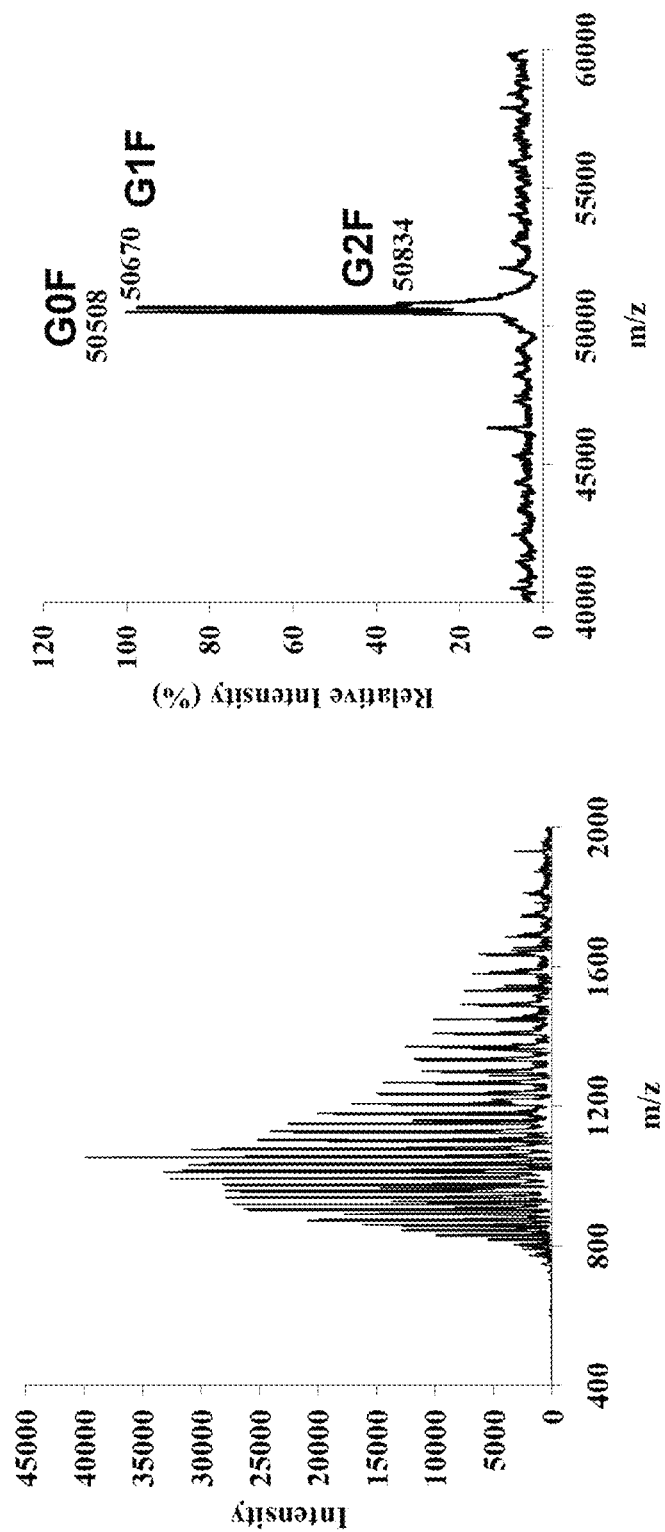

Rituximab, a therapeutic monoclonal antibody, was used as a model mAb to examine the deglycosylation activity and potential transglycosylation activity of the enzymes. The major Fc glycans of commercial rituximab are core-fucosylated biantennary complex type oligosaccharides carrying 0-2 galactose moieties named G0F, G1F, and G2F glycoforms, respectively, as revealed by matrix-assisted laser desorption ionization time of flight mass spectrometry (MALDI-TOF MS) analysis of the N-glycans released by PNGase F as shown in FIG. 10. Treatment of rituximab with the EndoS-GST fusion protein (here, referred as wild-type EndoS or EndoS) resulted in a rapid deglycosylation to give the corresponding Fc N-glycans (with only one GlcNAc at the reducing end), as shown in FIG. 11, and the deglycosylated rituximab that bears the fucosylated GlcNAc disaccharide moiety (Fucα1,6GlcNAc) at the glycosylation sites (N297). These results confirm the remarkable Fc glycan-hydrolyzing activity of the wild-type EndoS on intact IgG, implicating its usefulness in the first step for glycosylation remodeling of mAbs. The transglycosylation potential of EndoS and its mutants was then examined using the deglycosylated rituximab as the acceptor and several synthetic glycan oxazolines as the donor substrates, as depicted in FIGS. 3 A and B. The glycosylation remodeling process was monitored by sodium dodecylsulfate polyacrylamide gel electrophoresis (SDS-PAGE) and liquid chromatography mass spectrometry (LC-MS) analysis, as shown in FIG. 4A. The heavy chain and light chain of rituximab appeared at approximately 50 KDa and approximately 25 KDa, respectively, under reducing conditions (a, lane 1, in FIG. 4A). After deglycosylation with wild-type EndoS, the heavy chain appeared as a single band at approximately 48 KDa, suggesting the removal of the two N-glycans (each from a heavy chain) in rituximab (a, lane 2, in FIG. 4A). Incubation of the deglycosylated rituximab (1) and the synthetic sialoglycan oxazoline (2) (see FIG. 3A for structures) (donor/acceptor, 50:1, molar ratio) with mutant EndoS-D233A gave a transglycosylation product (3), the heavy chain of which appeared as a single band that was about 2 KDa larger than that of the deglycosylated rituximab (1) (a, lane 3, FIG. 4A). This result suggests that a new N-glycan was attached to each of the Fc heavy chains. Incubation of (1) and (2) with EndoS-D233Q gave the same transglycosylation product (a, lane 4, FIG. 4A). Interestingly, an essentially quantitative transglycosylation for the Fc domain of the intact antibody was achieved within 1 h incubation. It was found that a longer incubation (10 h) did not lead to hydrolysis of the transglycosylation product. These results indicate that the two EndoS mutants are new efficient glycosynthases that enable the glycosylation of deglycosylated intact IgG with complex type N-glycan without product hydrolysis.

Figures 4C, 4D:
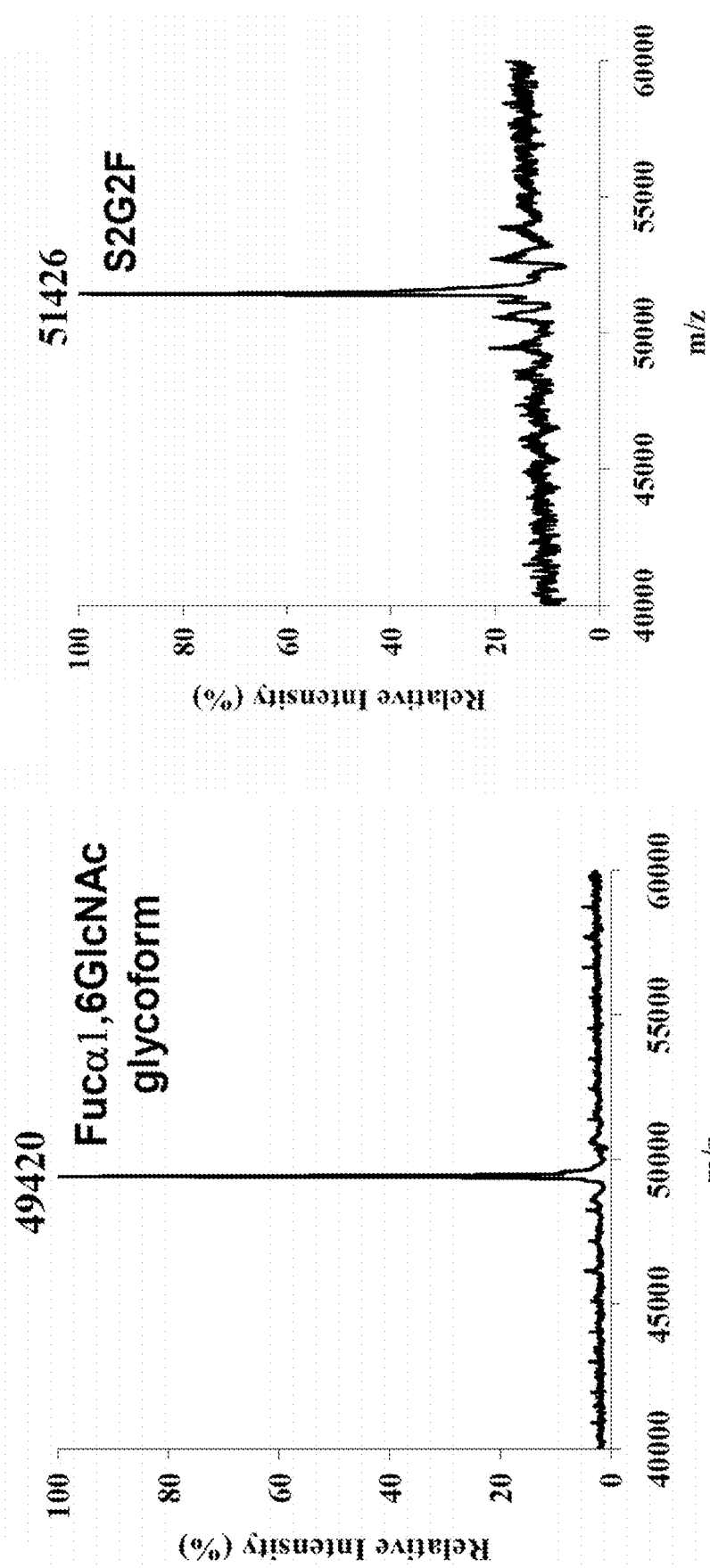
FIG. 4C shows the ESI-MS analysis of the de-glycosylated rituximab (1).
FIG. 4D shows the ESI-MS analysis of the transglycosylation product (3).
Figure 13:
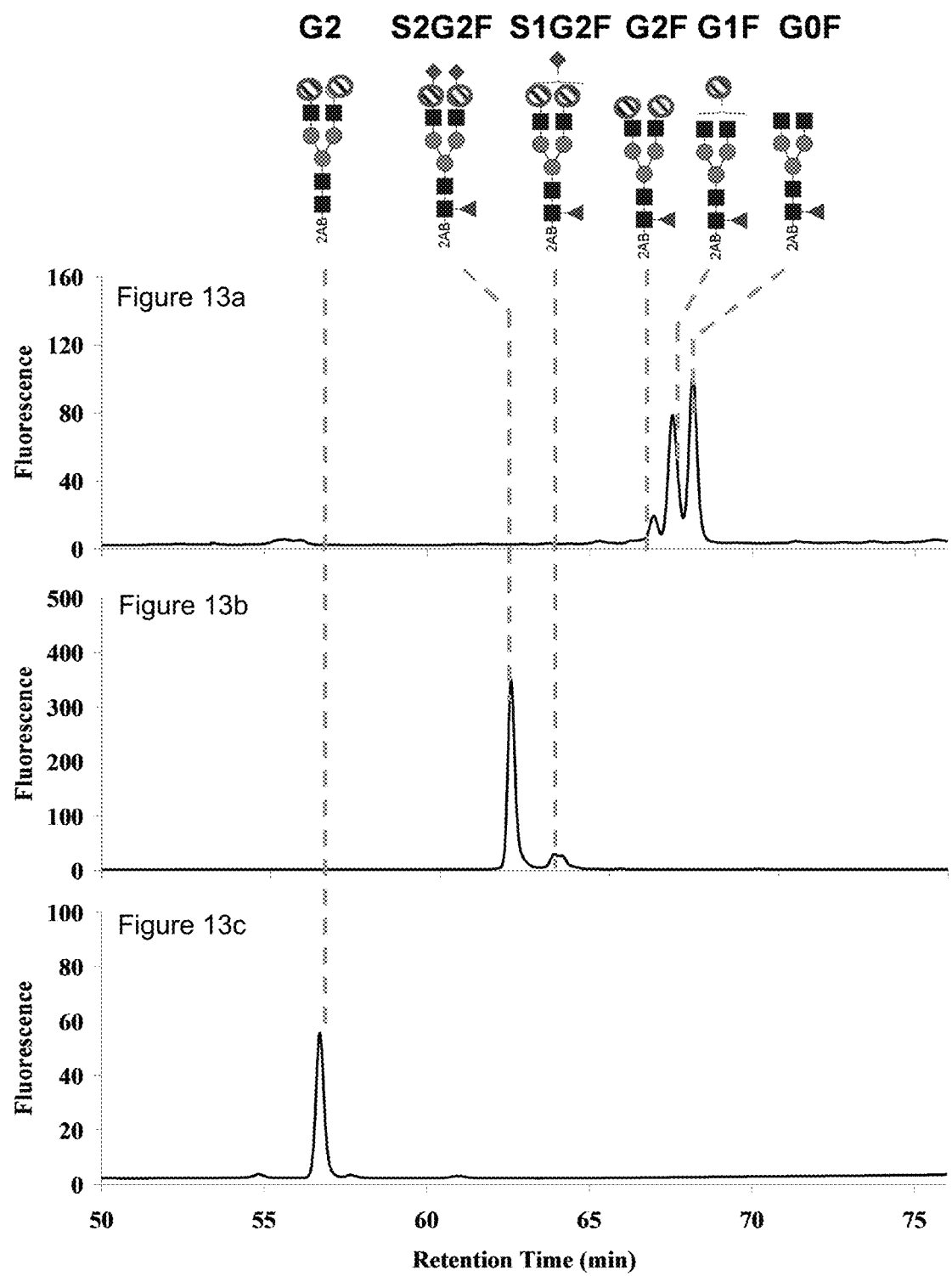
FIG. 13a shows the fluorescent HPLC profile of the 2-AB-labeled N-glycans released from commercial rituximab samples by PNGase F treatment. (■ GlcNAc; ● Man; ◐ Gal; ○ Glc; ▲ Fuc; ◆ Sia).
FIG. 13b shows the fluorescent HPLC profile of the 2-AB-labeled N-glycans released from sialylated rituximab (3) sample by PNGase F treatment. (■ GlcNAc; ● Man; ◐ Gal; ○ Glc; ▲ Fuc; ◆ Sia).
FIG. 13c shows the fluorescent HPLC profile of the 2-AB-labeled N-glycans released from non-fucosylated rituximab (10) sample by PNGase F treatment. (■ GlcNAc; ● Man; ◐ Gal; ○ Glc; ▲ Fuc; ◆ Sia).

The transglycosylation was further characterized by LC-MS analysis. The heavy chain and light chain of rituximab were separated under a LC-MS condition, as shown in FIGS. 12A-12E. Deconvolution of the light chain MS data gave a mass of 23 044, which was consistent with the calculated mass of rituximab light chain (M=23 042 Da).(47) Deconvolution of the MS data of the heavy chain gave three distinct m/z species, 50508, 50670, and 50834, as shown in FIG. 4B, which were in good agreement with the theoretical mass of heavy chain glycoforms: G0F, M=50 515 Da; G1F, M=50 677 Da; and G2F, M=50 839 Da; respectively.(47) The deconvoluted electron spray ionization mass spectrometry (ESI-MS) of the heavy chain of the deglycosylated rituximab (1) showed a single species at 49 420, as shown in FIG. 4C, which matched well with a heavy chain carrying a Fucα1,6GlcNAc disaccharide moiety (calculated, M=49 420 Da). After glycosylation remodeling, a single peak at 51 426 was observed from the heavy chain of the transglycosylation product (3), with an addition of 2006 Da to the deglycosylated heavy chain of the rituximab, as shown in FIG. 4D. This result indicates the attachment of a sialoglycan from the corresponding sugar oxazoline (2) to the heavy chain. The single band on SDS-PAGE and the neat MS spectra of the transglycosylation product clearly suggests that the transglycosylation was essentially quantitative on the two glycosylation sites of the Fc domain in rituximab (incomplete glycosylation of any of the two sites in the Fc homodimer would result in the observation of the Fucα1, 6GlcNAc-heavy chain after reduction, M=49 420 Da). To further confirm that the N-glycan was specifically attached to the GlcNAc of the Fc domain, the whole N-glycan was released from the glyco-remodeled rituximab (3) by treatment with PNGase F, which specifically hydrolyzes the amide bond between the Asn-glycan linkage. The released N-glycans were labeled by fluorescent tag 2-aminobenzamide (2-AB) and were subjected to fluorescent high-performance liquid chromatography (HPLC) and MS analysis. The LC-MS analysis clearly revealed that the released N-glycan was the expected biantennary complex type N-glycan carrying core fucose and terminal sialic acids, which consisted of approximately 92% disialylated N-glycan and approximately 8% monosialylated N-glycan, as shown in FIG. 13b. The N-glycan composition was well consistent with the ratio found in the corresponding N-glycan oxazoline (2) used for the transglycosylation. This result confirms that the transferred N-glycan was specifically attached to the GlcNAc primer in the deglycosylated rituximab.

The results set forth herein represents the first report of glycosylation remodeling of an intact IgG monoclonal antibody with an en bloc transfer of a full-size natural complex type N-glycan to the Fc domain through a highly efficient deglycosylation-reglycosylation protocol enabled by the combined use of EndoS and EndoS-based glycosynthase. After completion of the transglycosylation, the product was purified by a simple protein A affinity chromatography, giving the well-defined homogeneous glycoform. It should be pointed out that the commercial rituximab contains only trace amount of sialylated glycoform, as shown in FIG. 13a. Since sialylated Fc and IgG were proposed to have anti-inflammatory activity, the glycoengineered rituximab carrying fully sialylated Fc N-glycans may gain an anti-inflammatory function, thus potentially expanding its therapeutic coverage from cancer treatment to the treatment of autoimmune diseases.(21, 22)

Figures 4E, 4F:
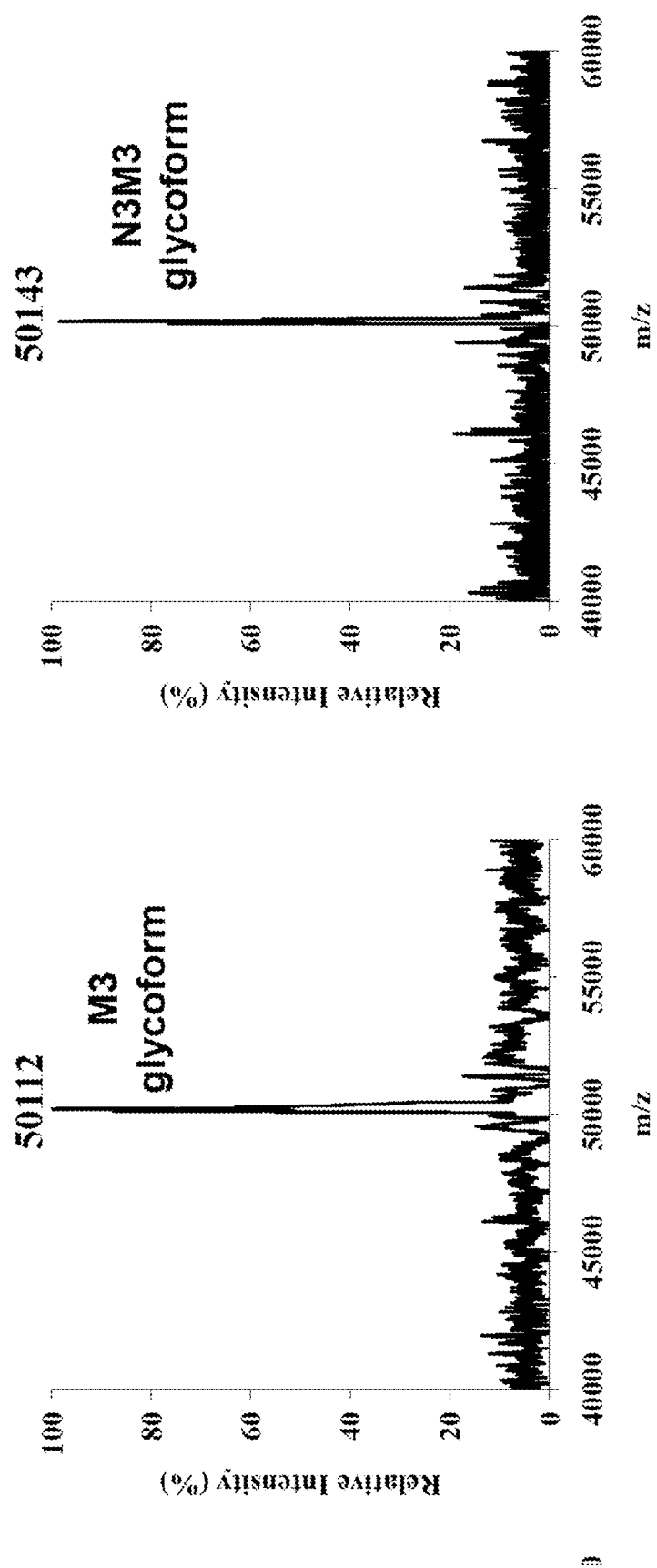
FIG. 4E shows the ESI-MS analysis of the transglycosylation product (5).
FIG. 4F shows the ESI-MS analysis of the transglycosylation product (7).

In addition to the sialylated complex type N-glycan oxazoline (2), the EndoS mutants were equally efficient to use the Man3GlcNAc core oxazoline (4)(48) and the azido-tagged N3Man3GlcNAc oxazoline (6)(49) for rituximab glycoengineering, leading to the formation of the corresponding homogeneous glycoforms, (5) and (7), respectively, as shown in FIG. 3A. The deconvoluted ESI-MS of the heavy chain of the transglycosylation product (5) showed a single species at 50 112, as shown in FIG. 4E, which matched well with the calculated molecular mass (M=50 109 Da) of the rituximab heavy chain carrying a Man3GlcNAc2 glycan. Similarly, the deconvoluted ESI-MS of the heavy chain of transglycosylation product (7) showed a single species at 50 143, as shown in FIG. 4F, which was in good agreement with the calculated molecular mass (M=50 134 Da) of the rituximab heavy chain carrying a N3Man3GlcNAc2 glycan. Again, these results indicate that the transglycosylation is essentially quantitative. It should be noted that decreasing the molar ratio of donor/acceptor to 25:1 still resulted in efficient transformation, implicating the remarkable transglycosylation efficiency of the EndoS glycosynthase mutants. In particular, the selective introduction of azide functionality on the core of the Fc N-glycan in intact monoclonal antibodies will allow further site-specific modifications of antibodies through click chemistry,(50, 51) which may be used for labeling and targeting purposes, or for expanding the diversity of antibody glycoforms for further structure-activity relationship studies.

Figure 14:
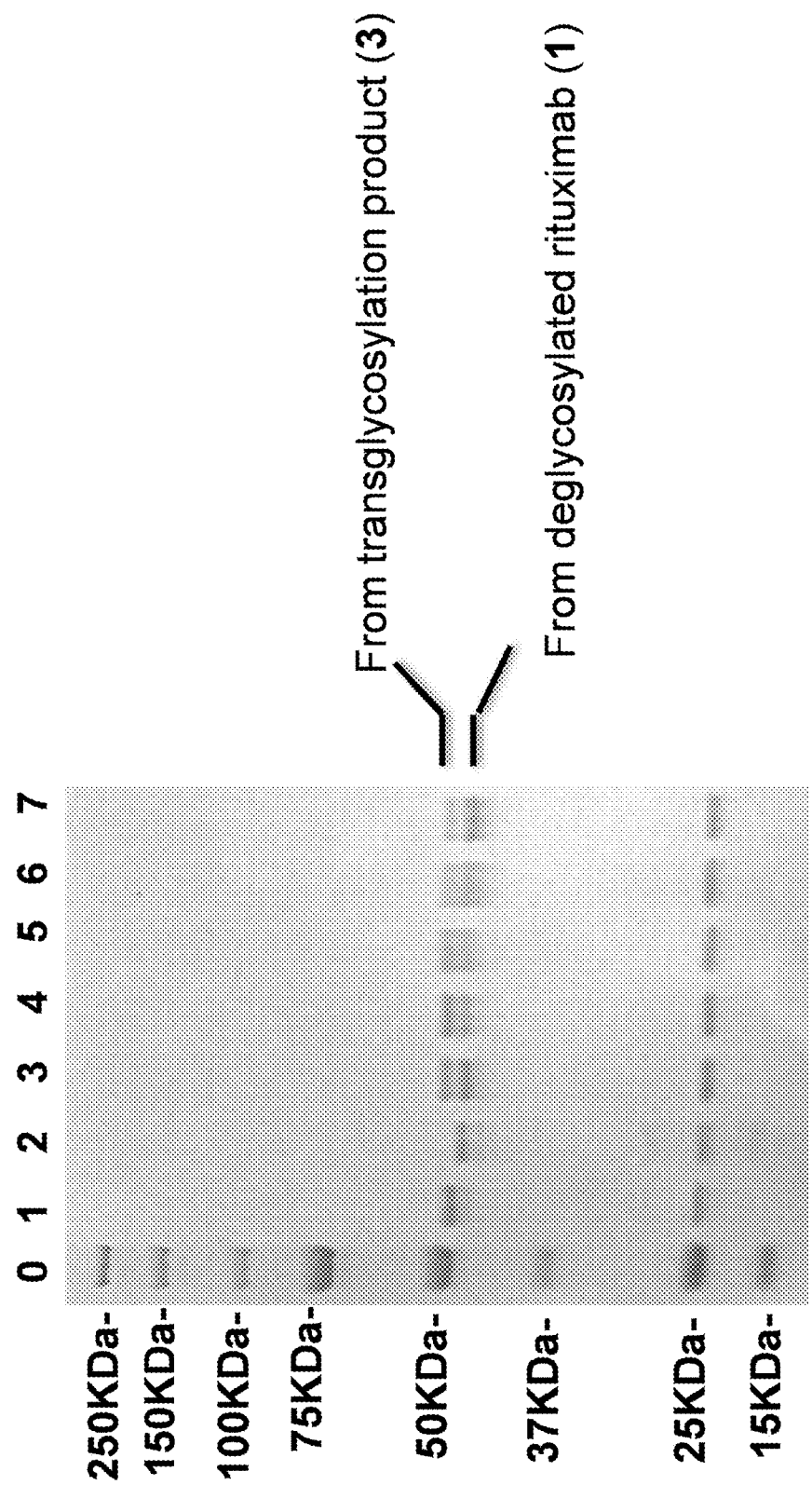
FIG. 14 shows the SDS-PAGE analysis of transglycosylation by wild type EndoS. Lane 0, protein markers; Lane 1, commercial rituximab; Lane 2, EndoS de-glycosylated rituximab (1); Lane 3 to Lane 7, monitoring of the transglycosylation reaction between de-glycosylated rituximab (1) and sialoglycan oxazoline (2): Lane 3, 15 mins; Lane 4, 30 mins; Lane 5, 1 h; Lane 6, 2 h; Lane 7, 4 h.

Wild-type EndoS was also tested for transglycosylation of deglycosylate rituximab (1) with the glycan oxazolines (2 and 4) under the same conditions as with the EndoS mutants and it was observed that only transient formation of the corresponding transglycosylation products were found as monitored by LC-MS, probably due to quick in situ hydrolysis of the products by the wild-type enzyme. Recently, Scanlan, Davis, and co-workers reported an independent study on the substrate specificity of EndoS and demonstrated that wild-type EndoS could use Man3GlcNAc oxazoline for efficient transglycosylation of deglycosylated IgG.(42) To address this apparent discrepancy of observations, the transglycosylation efficiency of wild-type EndoS was re-evaluated at a lower temperature (4° C.) using a much less quantity of enzyme, following the recent report.(42) Using this modified condition, significant transglycosylation was observed of the deglycosylated rituximab (1) with the complex sugar oxazoline (2) by the wild-type EndoS at the initial incubation period, but the product was gradually hydrolyzed when the incubation continued, as shown in FIG. 14. Thus, the reaction condition should be carefully controlled in order to trap the transglycosylation product when wild-type EndoS is used. For practical application, the EndoS glycosynthase mutants should be the choice for efficient and complete transglycosylation, as they are devoid of product hydrolytic activity.

Figure 5:
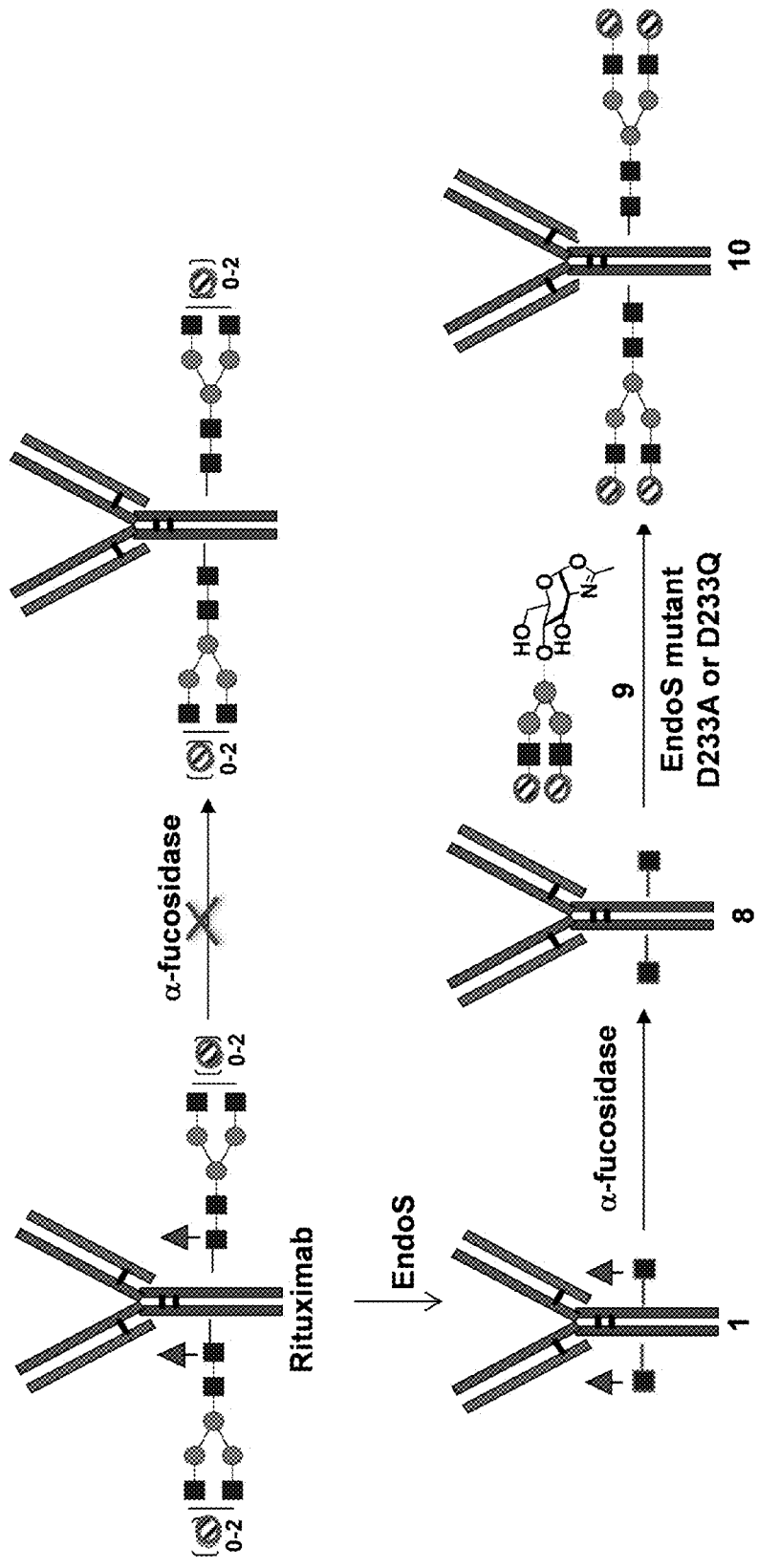
FIG. 5 A shows the enzymatic remodeling to non-fucosylated homogeneous glycoform of rituximab (▓ GlcNAc; ● Man; ◐ Gal; ○ Glc; ▲ Fuc; ◆ Sia).
Figure 15:
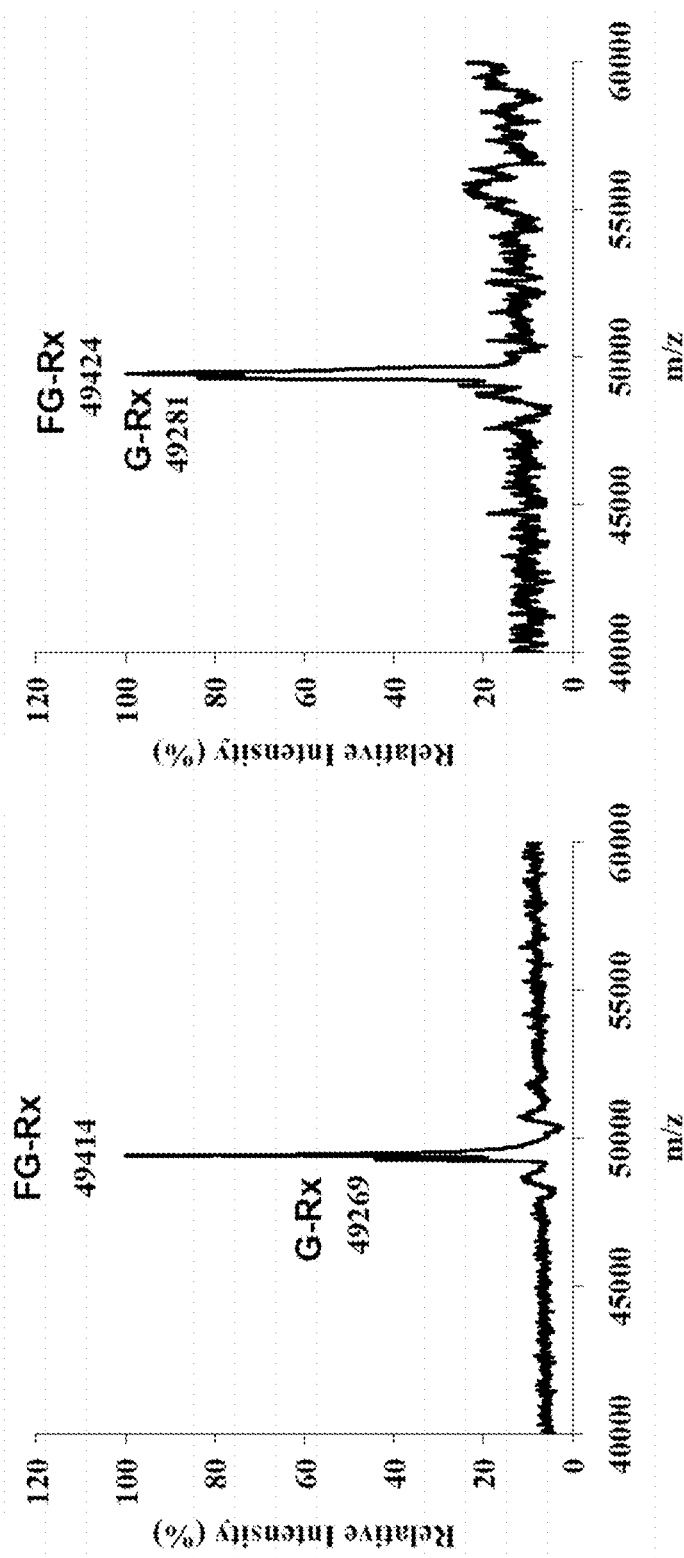
FIG. 15 A shows the LC-MS monitoring on defucosylation of Fuc(α2,6)GlcNAc-rituximab (1) with bovine kidney α-fucosidase. The deconvoluted ESI-MS profiles of the rituximab's heavy chain were shown (FG-Rx, heavy chain of Fuc(α2,6)GlcNAc-rituximab; G-Rx, heavy chain of GlcNAc-rituximab) following incubation with the α-fucosidase for 2 days.
Figure 15:
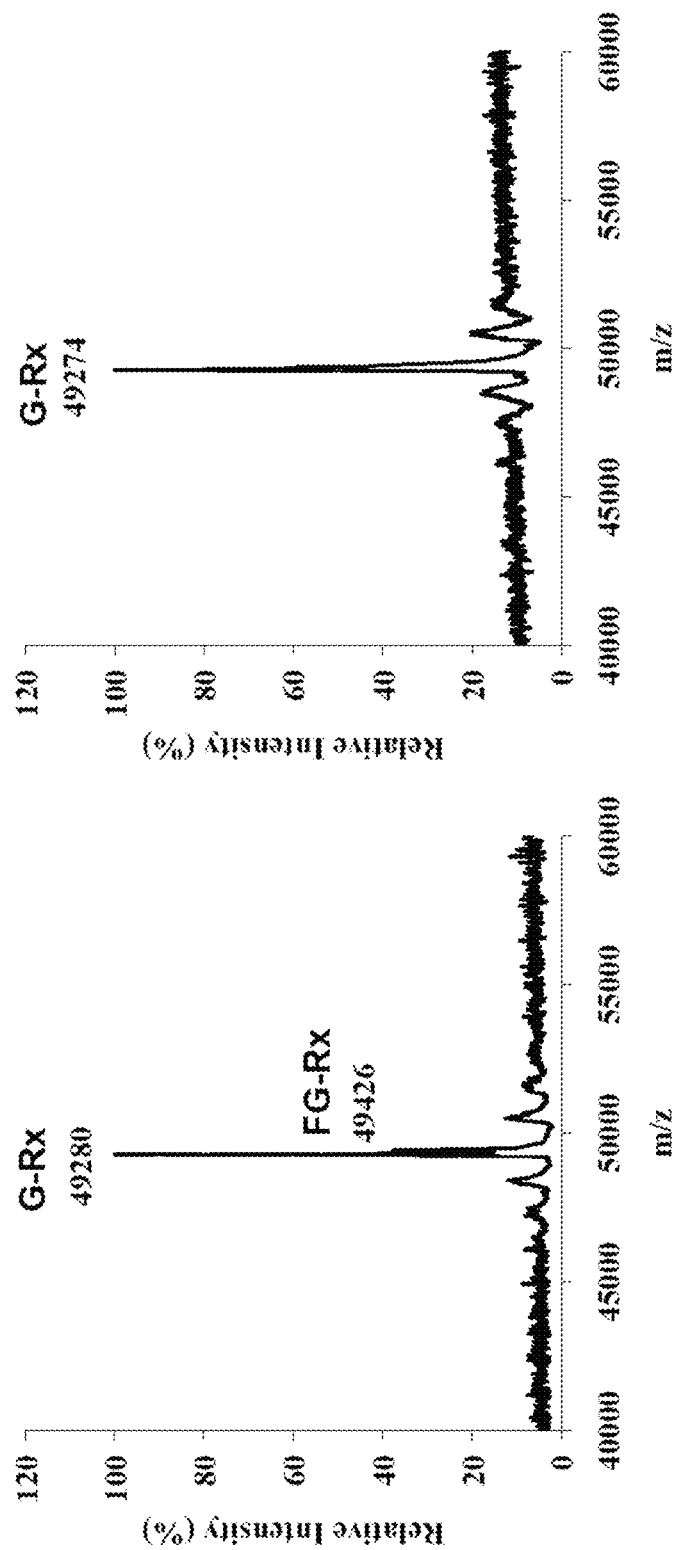

Glycoengineering of Rituximab to Provide Nonfucosylated and Galactosylated G2 Glycoform For anticancer therapy, nonfucosylated IgG glycoforms are desirable as it has been previously demonstrated that mAbs with low-fucose contents of Fc N-glycans showed enhanced ADCC activity in vitro and enhanced anticancer efficacy in vivo, particularly for those patients carrying the low affinity F158 allele of the FcγIIIa receptor.(16-19, 52) No efficient method was available to efficiently transform an existing fucosylated mAb (the major glycoform of recombinant mAbs produced in mammalian cells) to a nonfucosylated mAb. To address this issue, a series of commercially available α-fucosidases were tested, but none could remove the α1,6-fucose in the intact rituximab, see scheme in FIGS. 5 A and B. These results implicate that the α-1,6-fucose moiety might be shielded by the Fc domain and/or the complex N-glycan, making it inaccessible to α-fucosidases. It was theorized that, upon deglycosylation, the resulting Fuc(α1,6)GlcNAc glycoform of rituximab might be more accessible to α-fucosidases. Accordingly, the activity of several commercially available α-fucosidases was tested on the deglycosylated rituximab (1) that carries only the Fuc (α1,6)GlcNAc moiety. It was found that a nonspecific α-fucosidase from bovine kidney did have a moderate activity and was able to remove the fucose residue from the deglycosylated rituximab (1) to give the GlcNAc-containing rituximab (8) (See FIGS. 15 A-15 D). Although a relatively large amount of α-fucosidase and a prolonged reaction time were needed to achieve a complete defucosylation of the EndoS-deglycosylated rituximab due to the moderate activity of the α-fucosidase, the discovery of this α-fucosidase activity provides an alternative way to obtain the defucosylated rituximab precursor (8) for further glycoengineering.

Figure 5B:
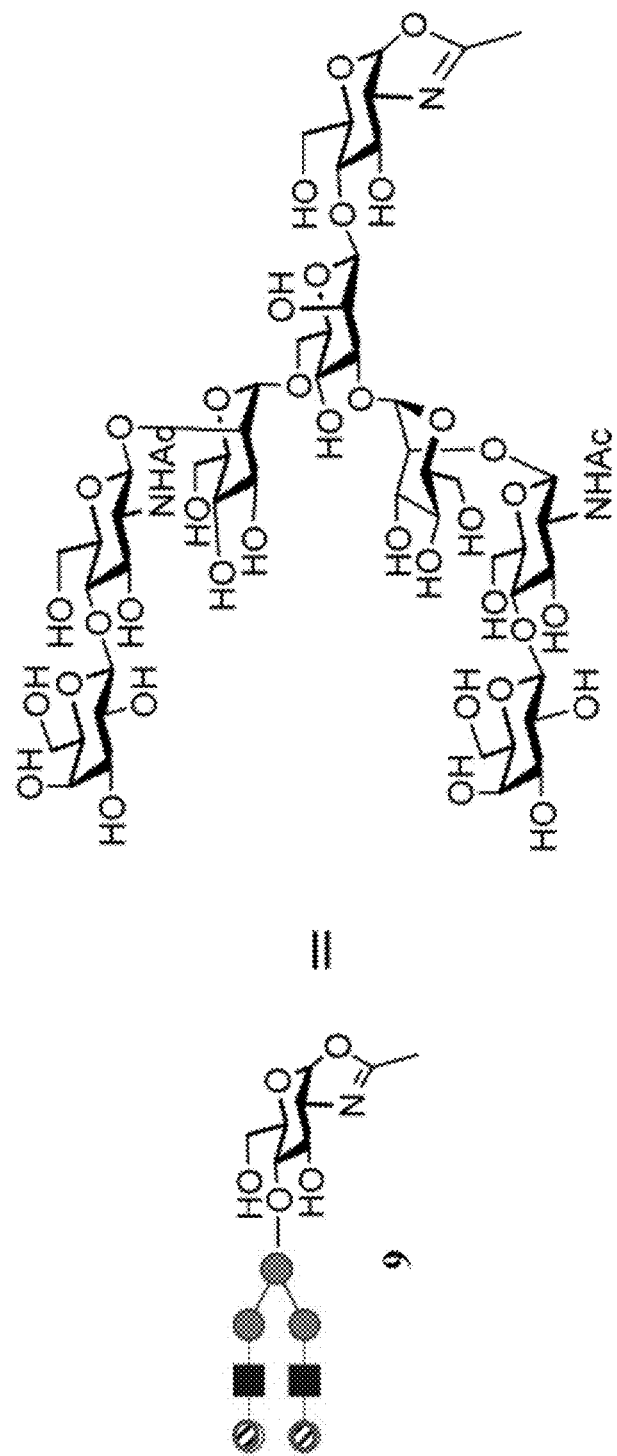
Figure 6C:
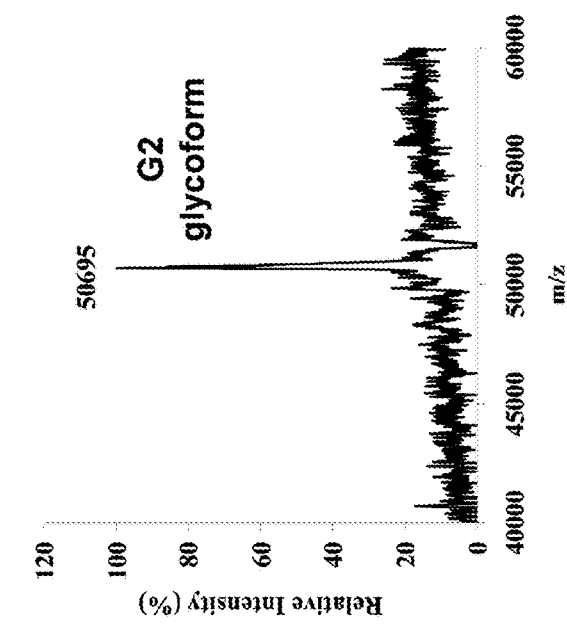
FIG. 6c shows the ESI-MS analysis of the heavy chain of the glycoengineered G2 rituximab (10).
Figure 6B:
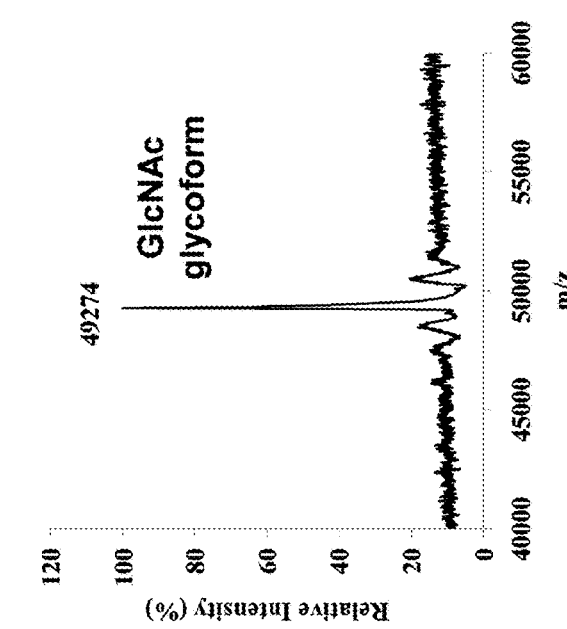
FIG. 6b shows the ESI-MS (after deconvolution) analysis of the heavy chain of the defucosylated rituximab (8).
Figure 6A:
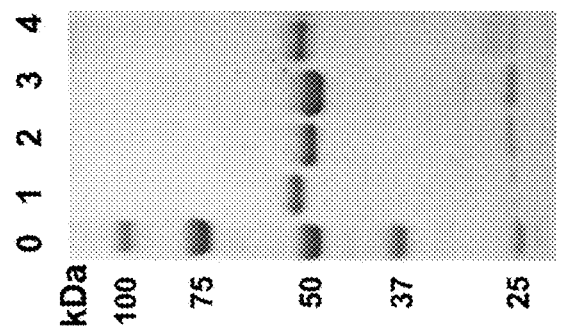
FIG. 6a shows SDS-PAGE analysis of glycoengineering of rituximab to the non-fucosylated G2 glycoform: Lane 0, protein markers; Lane 1, commercial rituximab; Lane 2, the EndoS de-glycosylated rituximab (1); Lane 3, the defucosylated product (8); Lane 4, the glycoengineered G2 glycoform.

Next, it was determined that the glycosynthases EndoS-D233A and EndoS-D233Q were also efficient to recognize the nonfucosylated GlcNAc in (8) for transglycosylation with a sialylated N-glycan oxazoline (9)(38) to provide the homogeneous, nonfucosylated G2 glycoform (10) in an essentially quantitative conversion, FIGS. 5A-5B. The product was purified by protein A affinity chromatography. The identity and purity of the glycoengineered product (10) were confirmed by SDS-PAGE and LC-MS analysis, as shown in FIG. 6a. The defucosylated rituximab (8) showed a single species at 49 274 (FIG. 6b), confirming the removal of the fucose (calcd. for the heavy chain of GlcNAc-rituximab, M=49 274 Da). The deconvoluted ESI-MS of the heavy chain of the transglycosylation product (10) appeared as a single species at 50 695 (FIG. 6c), which matched well with the calculated molecular mass (M=50 693 Da) of the rituximab heavy chain carrying an asialylated biantennary complex type N-glycan, Gal2GlcNAc2Man3GlcNAc2. In a comparative study, it was also found that, while mutants D233A and D233Q recognized both the fucosylated GlcNAc-rituximab (1) and the nonfucosylated GlcNAc-rituximab (8) as acceptors for transglycosylation, the two glycosynthase mutants preferred the fucosylated GlcNAc-rituximab (1) as acceptor, with a faster transglycosylation reaction than the nonfucosylated acceptor (8) (data not shown). Taken together, these experimental results revealed a combined enzymatic approach to making the nonfucosylated and fully galactosylated homogeneous glycoform from commercially available monoclonal antibodies. The resulting nonfucosylated and galactosylated rituximab is expected to gain improved ADCC and CDC effector functions, as suggested by previously studies.(2, 16-20, 52)

Site-Selective Fc Glycoengineering of IVIG to Provide Fully Fc Sialylated IVIG Glycoforms The successful glycosylation remodeling of rituximab prompted the examination of the chemoenzymatic method for glycoengineering of IVIG aiming to enhance its anti-inflammatory activity. IVIG is a pooled IgG fractions purified from the plasma of thousands of healthy donors. Recent studies have suggested that a minor, $\alpha$2,6-sialylated Fc glycoform is the active species in IVIG that confers anti-inflammatory activity as demonstrated in a mouse model of rheumatoid arthritis.(21, 22, 53, 54) Since the sialylated Fc glycoforms are minor components in IVIG,(55) the dependence of IVIG's anti-inflammatory activity on terminal Fc sialylation may partially explain why a high dose (1-2 g/kg) of infusion of IVIG is required for conferring protection. Direct sialylation of Fc and IVIG was attempted using human $\alpha$-1,6-sialyltransferase (ST6Gal-I) but the efficiency was low, and in most cases, only monosialylated glycoforms were obtained as the major products.(22, 56) Moreover, approximately 30% of the FAB domains in IVIG are N-glycosylated and lectin enrichment of Fc sialylated glycoforms of IVIG would be less efficient when the FAB glycans are sialylated.(2, 57) Therefore, it would be highly desirable if Fc-specific glycoengineering with sialylated N-glycans can be achieved without altering the FAB glycosylation.

Figure 7:
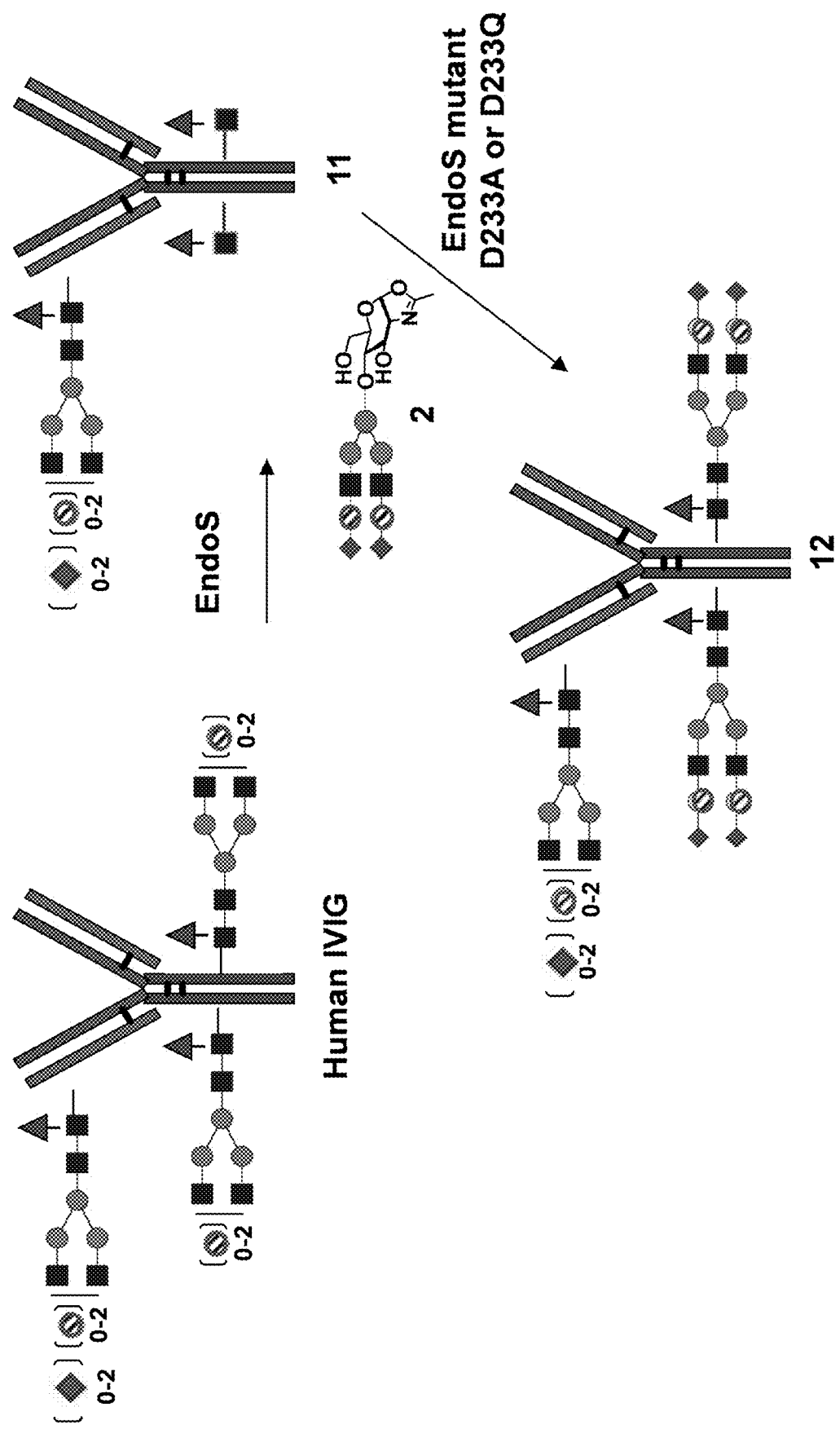
FIG. 7 shows the Site-specific Fc glycoengineering of human IVIG. (■ GlcNAc; ● Man; ◐ Gal; ○ Glc; ▲ Fuc; ◆ Sia).
Figure 8E:
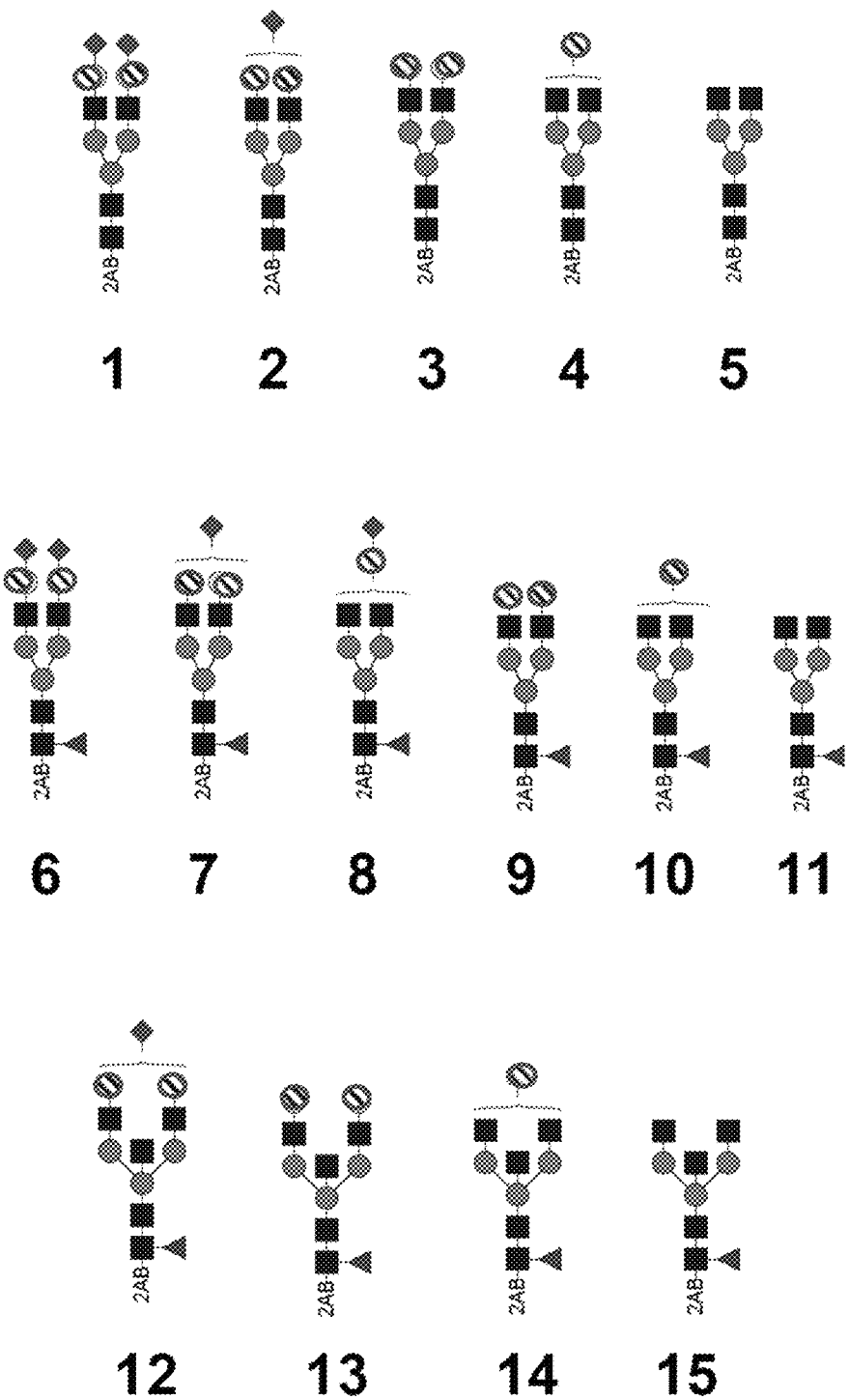
FIG. 8e shows the glycan structures corresponding to HPLC peaks 1-15 in FIGS. 8a-8d.
Figure 16:
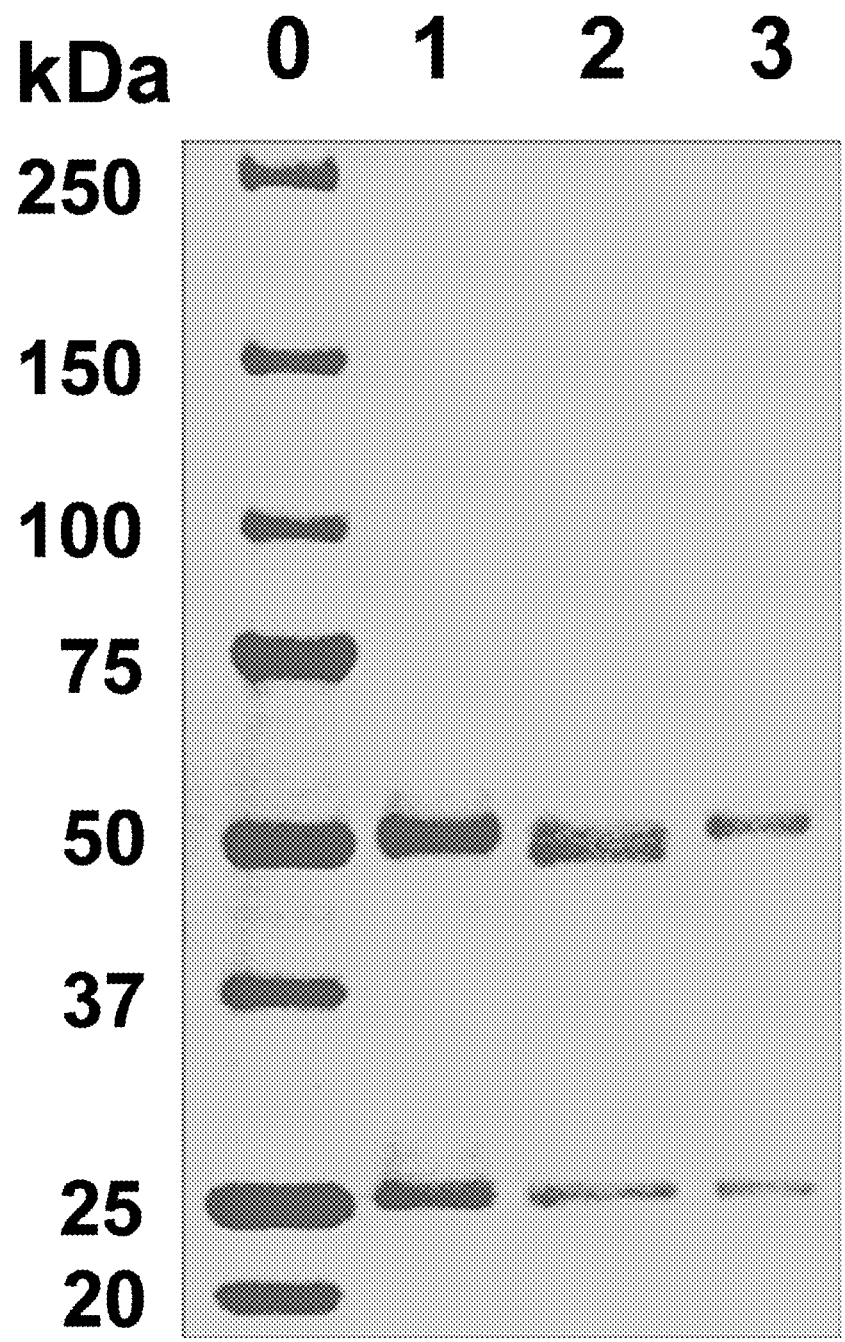
FIG. 16 shows the SDS-PAGE analysis of IVIG glycoengineering. Lane 0, protein marker; Lane 1, commercial IVIG; Lane 2, IVIG (11) after deglycosylation by EndoS; Lane 3, IVIG (12) after EndoS-D233Q catalyzed transglycosylation with sialoglycan oxazoline.

It was found that EndoS was able to selectively deglycosylate the Fc domain of IVIG without hydrolyzing the N-glycans at the FAB domains under a mild condition. Moreover, the deglycosylated Fc domain of IVIG (11) could be selectively glycosylated with a sialoglycan oxazoline (2) by the EndoS-D233Q mutant to give the Fc fully sialylated IVIG (12), as shown in FIG. 7. The glycoengineering was first monitored by SDS-PAGE analysis. The deglycosylation and reglycosylation of IVIG were apparent as shown in the change of the band size of the heavy chain, as shown in FIG. 16. To further characterize the site-selectivity of the glycoengineering of IVIG, the FAB and Fc domains were disconnected by papain digestion.(58) The Fc domain was isolated by protein A affinity chromatography and the FAB domains left in the flow-through were isolated by size exclusion chromatography on a fast protein liquid chromatography (FPLC) system. Then, the Fc and FAB N-glycans were released separately by PNGase F treatment, labeled with 2-aminobenzamide (2-AB),(59) and analyzed by HPLC (fluorescent detection and quantitation) and MS characterization. The FAB and Fc N-glycan profiles before and after glycoengineering of IVIG were shown in FIGS. 8a-8d. It was found that the Fc glycosylation patterns of IVIG were more complex than the Fc glycosylation of monoclonal antibody rituximab. In addition to G0F, G1F, and G2F glycoforms as the major components, there were a significant amount of monosialylated (peaks 2 and 7) glycoforms (approximately 10%) and bisecting GlcNAc-containing glycoforms (peaks 13-15) (5%) (FIG. 8a). The Fc glycosylation after glycoengineering (through EndoS-deglycosylation and subsequent transglycosylation with sialoglycan oxazoline (2) by EndoS-D233Q) showed the fully sialylated glycans (peaks 1 and 6) as the major glycoforms (>90%) (FIG. 8b). Interestingly, the FAB glycosylation patterns were similar before and after the glycoengineering process (compare FIGS. 8c and 8d), except the generation of a small amount of the fully sialylated glycoform (peak 6). These results indicate that the EndoS-based glycosylation remodeling process is highly selective for the Fc N-glycans of intact IgG antibodies even in the presence of FAB glycosylation. The remarkable selectivity and high efficiency of the present Fc glycoengineering approach provide a novel avenue to transforming the commercial IVIG into fully Fc-sialylated IVIG preparation that is expected to exhibit enhanced anti-inflammatory activity, as demonstrated in previous studies using a mouse model.(21, 22, 53, 54).

Binding of the Glycoengineered Rituximab to the Stimulatory Fcγ Receptor (FcγRIIIa) and the Inhibitory Fcγ Receptor (FcγRIIb)

Figure 9B:
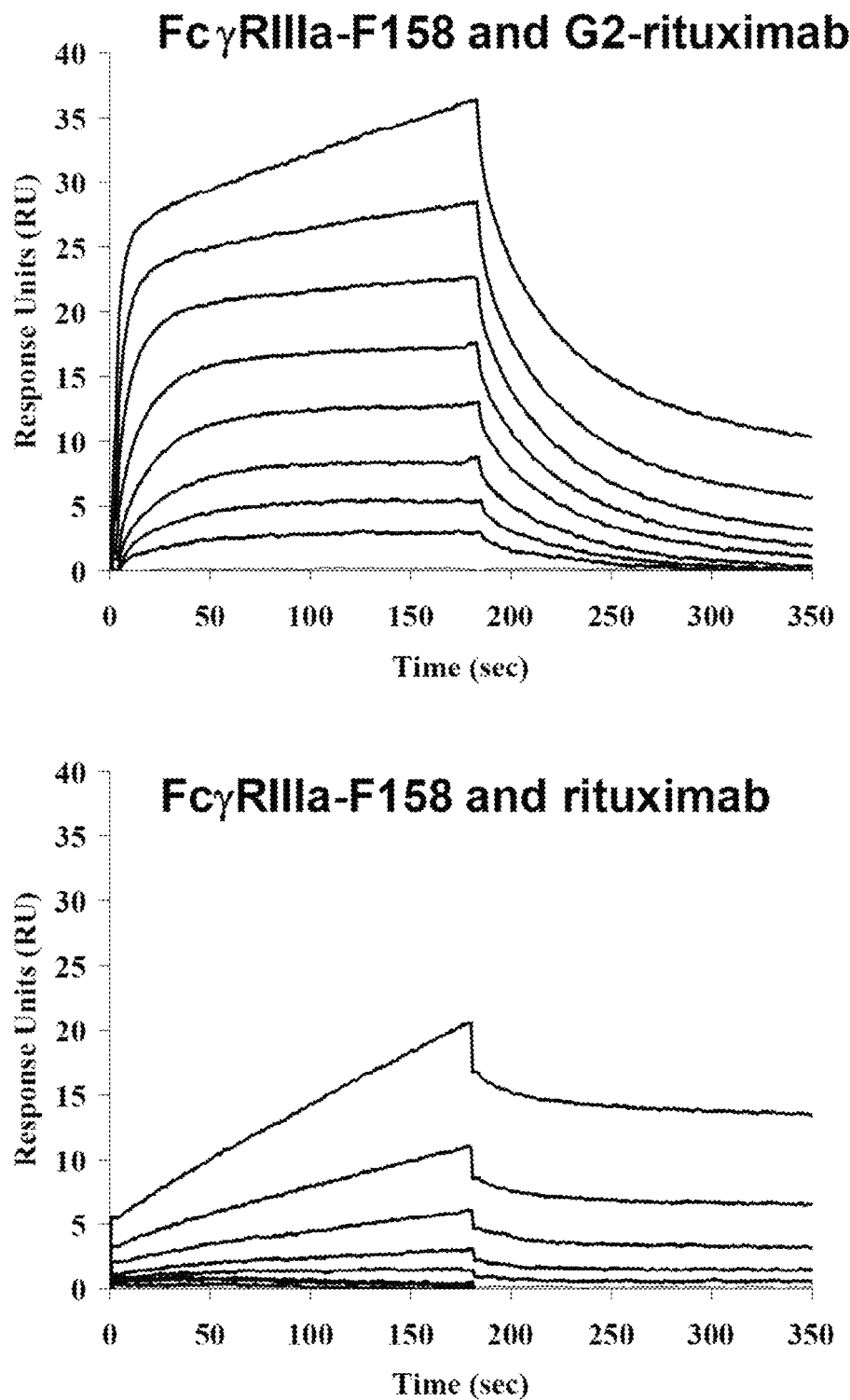
FIG. 9 A shows typical SPR sensorgrams of the binding of G2-rituximab and commercial rituximab with FcγRIIIa-V158. The antibodies were immobilized by Protein A capture and the binding was analyzed by injecting the respective Fcγ receptors at a serial 2-fold dilutions starting at 40 μg/mL (1.33 uM).

The affinity of the remodeled glycoforms of rituximab for respective Fcγ receptors (FcγRIIIa-F158, FcγRIIIa-V158, and FcγRIIb) was examined by surface plasmon resonance (SPR) analysis. The rituximab glycoforms were site-specifically immobilized on a protein A chips and the Fcγ receptors at various concentrations were injected as analytes, following our recently reported procedures.(35) As expected, the nonfucosylated G2 glycoform showed significantly enhanced affinity for both the low-affinity and high-affinity FcγIIIa receptors, FcγRIIIa-F158 and FcγRIIIa-V158, when compared with the commercially available rituximab, as shown in FIGS. 9a-9c. The KD values for the binding of the G2 glycoform (10) to the FcγRIIIa-F158 and FcγRIIIa-V158 were 123±11 and 12±2 nM, respectively, which were obtained by fitting the binding data with a 1:1 steady-state model using the BIAcore T100 evaluation software. On the other hand, the KD values for the binding of the commercial rituximab to the FcγRIIIa-F158 and FcγRIIIa-V158 were estimated to be 1042±155 and 252±18 nM, respectively. Thus, the affinity of the glycoengineered G2 glycoform for the low-affinity and high-affinity Fcγ receptors (FcγRIIIa-F158 and FcγRIIIa-V158) was about 9-fold and 20-fold higher than the commercial rituximab, respectively. On the other hand, the G2 glycoform and the commercial rituximab demonstrated comparable affinity for the inhibitory Fcγ receptor FcγRIIb with the KD values of 2.3±0.5 and 2.0±0.7 μM, respectively. These results reveal a clear gain of beneficial functions for the glycoengineered rituximab. It should be pointed out that an efficient preparation of high-affinity FcγRIIIa-binding glycoforms is clinically significant to address the issue of Fcγ receptor polymorphism found in cancer patients who are less or not responsive to the treatment with common MAbs. In these patients, their FcγRIIIa-F158 allele has a low affinity to the therapeutic mAbs such as rituximab in comparison with the high-affinity receptor, FcγRIIIa-V158 allele.(52, 60, 61) Fcγ receptor-mediated effector functions were also suggested to be an important mechanism for achieving protective immunity for HIV-neutralizing antibodies.(62) Thus, the glycoengineering approach described here may find wide applications in producing various defined glycoforms of monoclonal antibodies valuable for functional studies as well as for biomedical applications.

An efficient chemoenzymatic approach to glycoengineering of intact IgG antibodies is described herein. The two new EndoS-based glycosynthases generated by site-directed mutagenesis demonstrate broad substrate specificity capable of transferring sialylated and asialylated and complex type N-glycans as well as selectively modified N-glycan core from the corresponding glycan oxazolines to Fc-deglycosylated intact antibodies. In addition, the deglycosylation/reglycosylation approach is efficient for both core-fucosylated and nonfucosylated IgG antibodies when an α-fucosidase is adequately combined. These new findings significantly expand the scope of the chemoenzymatic method and made possible an efficient transformation of intact monoclonal antibodies into various well-defined glycoforms that are hitherto difficult to obtain by existing methods. It is expected that this glycoengineering approach may facilitate the development of biosimilar and/or biobetter biologics that possess improved therapeutic efficacy and/or gain new functions.

Materials and Methods

Monoclonal antibody rituximab (rituxan, Genentech Inc., South San Francisco, Calif.) and IVIG were purchased through Premium Health Services Inc. (Columbia, Md.). Sialoglycan oxazoline (2) and asialo-complex-type glycan oxazoline (5) were synthesized following previously reported procedure.(38, 46) Bovine kidney α-1-fucosidase was purchased from Sigma (St. Louis, Mo.) and Prozyme (Hayward, Calif.). Endo-β-N-acetylglucosaminidase from *Arthrobacter protophormiae* (EndoA) and endo-β-N-acetylglucosaminidase from *Mucor hiemalis* (EndoM) and their mutants were overproduced in *E. coli* following the reported procedures.(38) PNGase F was purchased from New England Biolabs (Ipswich, Mass.).

Liquid Chromatography Mass Spectrometry (LC-MS)

The LC-MS was performed on a LxQ system (Thermo Scientific) with a Hypersil GOLD column (1.9 μm, 50×2.1 mm). The IgG samples were treated with 0.5% β-mercaptoethanol and heated at 60° C. for 15 min then subject to LC-MS measurement. The analysis was performed at 60° C. eluting with a linear gradient of 10-40% MeCN containing 0.1% formic acid within 10 min at a flow rate of 0.25 mL/min.

Electron Spray Ionization Mass Spectrometry (ESI-MS) and Matrix-Assisted Laser Desorption/Ionization Time of Flight Mass Spectrometry (MALDI-TOF MS)

The ESI-MS spectra were measured on a Waters Micromass ZQ-4000 single quadruple mass spectrometer. The MALDI-TOF MS was performed on an Autoflex II MALDI-TOF mass spectrometer (Bruker Daltonics, Billerica, Mass.). The instrument was calibrated by using ProteoMass Peptide MALDI-MS calibration kit (MSCAL2, Sigma/Aldirich). The matrix of 2,5-dihydroxybenzoic acid (DHB) was used for the neutral glycans and 2',4',6'-trihydroxyacetophenone (THAP) was used for the acidic glycans.

Overexpression and Purification of EndoS and Mutants

Wild-type EndoS was overproduced in *E. coli* and purified according to the previously reported procedures,(40, 63) using the plasmid pGEX-EndoS that was kindly provided by Dr. M. Collin (Lund University, Sweden). The two EndoS mutants, D233A and D233Q, were generated using the GENEART site-directed mutagenesis kit (Invitrogen) per the manufacturer's directions. The pGEX-EndoS plasmid was used as the template, and LA Taq polymerase (Takara, Japan) was used for PCR. Mutations were confirmed by DNA sequencing and transformed into BL21(DE3). The transformants were cultured in Luria-Bertani medium containing 100 mg/L carbenicillin and induced with 0.1 mM isopropyl-β-d-thiogalactopyranoside for 16 h at 25° C. The cells were harvested by centrifugation at 1700 g for 15 min at 4° C. The cell pellet was suspended in phosphate-buffered saline (pH 7.4) with lysozyme and PMSF. The lysed mixture was centrifuged at 16 000 g for 20 min at 4° C. After centrifugation, the supernatant from the cell lysis was applied to 3 mL of 50% glutathione-Sepharose 4B resin (GE Healthcare). Samples were incubated at 25° C. for 60 min with gentle rocking. The resin was applied to a 10 mL column (PD-10 GE Healthcare) and washed five times with PBS. 500 μL of glutathione elution buffer (50 mM Tris-HCl, 10 mM glutathione, pH 8.0) was added to the column, incubated at room temperature for 5 min, collected, and then repeated three times. The eluted fractions were pooled and dialyzed against sodium phosphate buffer (50 mM, pH 7.0) overnight at 4° C. Protein samples were then concentrated using Amicon ultra centrifugal filters 10 kDa (Millipore). Concentrated protein samples were analyzed by SDS-PAGE, and protein concentration was quantified using a Nano-Drop 2000c spectrophotometer. The yield of overproduction of the wild-type EndoS was approximately 40 mg/L, and the yield for the mutants was approximately 30 mg/L.

Deglycosylation of Rituximab by Wild-Type EndoS to Give (Fucα1,6)GlcNAc-Rituximab (1)

Commercial rituximab (20 mg) in a Tris-Cl buffer (50 mM, pH 8.0, 2 mL) was incubated with EndoS (30 μg) at 37° C. for 1 h. LC-MS and SDS-PAGE analyses indicated the complete cleavage of the N-glycans on the heavy chain. The reaction mixture was subject to affinity chromatography on a column of protein A-agarose resin (5 mL) that was pre-equilibrated with a Tris-Cl buffer (20 mM, pH 8.0). The column was washed with Tris-Cl (20 mM, pH 8.0, 25 mL) and glycine-HCl (20 mM, pH 5.0, 20 mL) successively. The bound IgG was released with glycine-HCl (100 mM, pH 2.5, 20 mL), and the elution fractions were immediately neutralized with Tris-Cl buffer (1.0 M, pH 8.8). The fractions containing the Fc fragments were combined and concentrated by centrifugal filtration (Amicon Ultra centrifugal filter, Millipore, Billerica, Mass.) to give (Fucα1,6)GlcNAc-rituximab (1) (18 mg). LC-MS: calculated for the heavy chain of (Fucα1,6)GlcNAc-rituximab (1), M=49 420 Da; (47) found (m/z), 49 420 (deconvolution data).

Transglycosylation of (Fucα1,6)GlcNAc-Rituximab (1) with Sialoglycan Oxazoline (2) by EndoS Mutants D233A or D233Q A solution of (Fucα1,6)GlcNAc-rituximab (1) (10 mg) and sialoglycan-oxazoline (2) (10 mg) in a Tris buffer (50 mM, pH 7.4, 2 mL) was incubated with the EndoS mutant D233A or D233Q (200 μg) at 30° C. Aliquots were taken at intervals and were analysis by LC-MS. After 2-3 h, LC-MS monitoring indicated the complete reaction of (Fucα1,6)GlcNAc-rituximab (1) to give the transglycosylation product (3) carrying the fully sialylated N-glycans. The reaction mixture was subject to an affinity chromatography on a protein A-agarose column following the procedure described above. Fractions containing the product were combined and concentrated by ultracentrifugation to give sialylated rituximab (3) (11 mg, quantitative). LC-MS: calculated for the heavy chain of (3) carrying the fully sialylated N-glycan, M=51 421 Da; found (m/z), 51 426 (deconvolution data).

Transglycosylation of (Fucα1,6)GlcNAc-Rituximab (1) with Man3GlcNAc Oxazoline (4) and the Azide-Tagged Man3GlcNAc Oxazoline (6) by EndoS-D233Q The transglycosylation was performed as described for the preparation of (3) to give the corresponding products. LC-MS analysis of glycoengineered rituximab (5 and 7): calculated for the heavy chain of (5) carrying the fucosylated Man3GlcNAc2 N-glycan, M=50 109 Da; found (m/z), 50 112 (deconvolution data); calculated for the heavy chain of (7) carrying the fucosylated azido-Man3GlcNAc2 N-glycan, M=50 134 Da; found (m/z), 50 143 (deconvolution data).

Defucosylation of (Fucα1,6)GlcNAc-Rituximab (1) by Bovine Kidney α-Fucosidase

A solution of (Fucα1,6)GlcNAc-rituximab (1) (2 mg) in a phosphate buffer (50 mM, pH 5.5, 200 μL) containing 0.05 sodium azide was incubated with the fucosidase from bovine kidney (Prozyme, 5 U) at 37° C. Aliquots were taken at intervals and were analyzed by LC-MS. After 20 days, LC-MS monitoring indicated the complete defucosylation of (Fucα1,6)GlcNAc-rituximab (1) to give the product, GlcNAc-rituximab (2). The reaction mixture was subject to affinity chromatography on a column of protein A following the procedure described above. Fractions containing the product were combined and concentrated by ultracentrifugation to give GlcNAc-rituximab (2) (2 mg, quantitative). LC-MS: calculated for the heavy chain of GlcNAc-rituximab (2) carrying a GlcNAc moiety, M=49 274 Da; found (m/z), 49 274 (deconvolution data).

Transglycosylation of GlcNAc-Rituximab (4) with Asialylated Complex-Type Glycan Oxazoline (5) by D233Q Mutant A solution of GlcNAc-rituximab (4) (2 mg) and oxazoline (5) (5 mg) in a Tris buffer (50 mM, pH 7.4, 0.5 mL) was incubated with the EndoS-D233Q (200 μg) at 37° C. Aliquots were taken at intervals and were analyzed by LC-MS. After 2 h, LC-MS monitoring indicated the complete reaction of 4 to give the corresponding transglycosylation product (6). The reaction mixture was subject to affinity chromatography on a column of protein A. Fractions containing the product were combined and concentrated by ultracentrifugation to give the nonfucosylated rituximab glycoform (6) (2 mg, quantitative). LC-MS: calculated for the heavy chain of (6) carrying the nonfucosylated N-glycan, M=50 693 Da; found (m/z), 50 695 (deconvolution data).

Site-Specific Deglycosylation at the Fc Domain of IVIG by EndoS

Commercial IVIG (20 mg) in a Tris-Cl buffer (50 mM, pH 8.0, 2 mL) was incubated with EndoS (SEQ ID NO: 1) (30 μg) at 37° C. for 1 h. The residue was subject to affinity chromatography on a column of protein A to give the (Fucα1,6)GlcNAc-IVIG (20 mg, quantitative), in which the Fc N-glycans were removed leaving the α1,6-fucosylated GlcNAc at the N297 sites.

Transglycosylation of (Fucα1,6)GlcNAc-IVIG with Sialoglycan Oxazoline (2) by D233Q Mutant A solution of (Fucα1,6)GlcNAc-IVIG (3 mg) and sialoglycan-oxazoline (2) (3 mg) in a Tris buffer (50 mM, pH 7.4, 2 mL) was incubated with the D233Q mutant(SEQ ID NO: 2) (60 μg) at 30° C. After 2 h, SDS-PAGE analysis indicated the complete reaction of (Fucα1,6)GlcNAc-IVIG to give the transglycosylation product. The reaction mixture was subject to affinity chromatography on a column of protein A to provide the glyco-remodeled IVIG (3 mg, quantitative), in which the Fc N-glycans were remodeled to the fully sialylated complex type N-glycans.

Surface Plasmon Resonance (SPR) Binding Experiments

The binding between different glycoforms of IgG and Fcγ receptors was measured by surface plasmon resonance (SPR) using a Biacore T100 instrument (GE Healthcare, USA). Protein A of 5000 RU was immobilized on a CM5 biosensor chip (GE Healthcare) using a standard primary amine coupling chemistry at pH 4.5 to capture the different glycoforms of IgG. A reference flow cell was prepared similarly without injecting protein A. Each individual glycoform of IgG in HBS-P buffer (10 mM HEPES pH 7.4, 0.15 M NaCl, 0.05% v/v surfactant P20) was injected at 10 μL/min onto the protein A surface and reached the capture level of 150 RU. A serial dilution of FcγIIIa and FcγIIb receptors was injected at 10 μL/min. After each cycle, the surface was regenerated by injecting 10 mM HCl at 10 μL/min for 30 s. Data were fitted into a 1:1 Langmuir binding model using BIAcore T100 evaluation software to obtain the equilibrium constant (KD) data.

REFERENCES

The contents of all references cited herein are hereby incorporated by reference herein for all purposes.

1. Adams, G. P.; Weiner, L. M., Monoclonal antibody therapy of cancer. Nat. Biotechnol. 2005, 23, 1147-1157.
2. Jefferis, R., Glycosylation as a strategy to improve antibody-based therapeutics. Nat. Rev. Drug Discovery 2009, 8, 226-234.
3. Aggarwal, S., What's fueling the biotech engine-2010 to 2011. Nat. Biotechnol. 2011, 29, 1083-1089.
4. Nimmerjahn, F.; Ravetch, J. V., Fcγ receptors as regulators of immune responses. Nat. Rev. Immunol. 2008, 8, 34-47.
5. Takahashi, N.; Nakagawa, H.; Fujikawa, K.; Kawamura, Y.; Tomiya, N., Three-dimensional elution mapping of pyridylaminated N-linked neutral and sialyl oligosaccharides. Anal. Biochem. 1995, 226, 139-146.
6. Wormald, M. R.; Rudd, P. M.; Harvey, D. J.; Chang, S. C.; Scragg, I. G.; Dwek, R. A., Variations in Oligosaccharide-Protein Interactions in Immunoglobulin G Determine the Site-Specific Glycosylation Profiles and Modulate the Dynamic Motion of the Fc Oligosaccharides. Biochemistry 1997, 36, 1370-1380.
7. Jefferis, R., Glycosylation of Recombinant Antibody Therapeutics. Biotechnol. Prog. 2005, 21, 11-16.
8. Sondermann, P.; Huber, R.; Oosthuizen, V.; Jacob, U., The 3.2-A crystal structure of the human IgG1 Fc fragment-FcγRIII complex. Nature 2000, 406, 267-273.
9. Krapp, S.; Mimura, Y.; Jefferis, R.; Huber, R.; Sondermann, P., Structural Analysis of Human IgG-Fc Glycoforms Reveals a Correlation Between Glycosylation and Structural Integrity. J. Mol. Biol. 2003, 325, 979-989.
10. Crispin, M.; Bowden, T. A.; Coles, C. H.; Harlos, K.; Aricescu, A. R.; Harvey, D. J.; Stuart, D. I.; Jones, E. Y., Carbohydrate and Domain Architecture of an Immature Antibody Glycoform Exhibiting Enhanced Effector Functions. J. Mol. Biol. 2009, 387, 1061-1066.
11. Ferrara, C.; Grau, S.; Jager, C.; Sondermann, P.; Brunker, P.; Waldhauer, I.; Hennig, M.; Ruf, A.; Rufer, A. C.; Stihle, M.; Umana, P.; Benz, J., Unique carbohydrate-carbohydrate interactions are required for high affinity binding between FcγRIII and antibodies lacking core fucose. Proc. Natl. Acad. Sci. U.S.A. 2011, 108, 12669-12674.
12. Yamaguchi, Y.; Nishimura, M.; Nagano, M.; Yagi, H.; Sasakawa, H.; Uchida, K.; shi-ara, K.; Kato, K., Glycoform-dependent conformational alteration of the Fc region of human immunoglobulin G1 as revealed by NMR spectroscopy. *Biochem. Biophys. Acta* 2006, 1760, 693-700.

13. Matsumiya, S.; Yamaguchi, Y.; Saito, J.; Nagano, M.; Sasakawa, H.; Otaki, S.; Satoh, M.; shi-ara, K.; Kato, K., Structural Comparison of Fucosylated and Nonfucosylated Fc Fragments of Human Immunoglobulin G1. *J. Mol. Biol.* 2007, 368, 767-779.

14. Barb, A. W.; Prestegard, NMR analysis demonstrates immunoglobulin G N-glycans are accessible and dynamic. *Nat. Chem. Biol.* 2011, 7, 147-153.

15. Nimmerjahn, F.; Ravetch, J. V., Anti-inflammatory actions of intravenous immunoglobulin. *Annu. Rev. Immunol.* 2008, 26, 513-533.

16. Shields, R. L.; Lai, J.; Keck, R.; O'Connell, L. Y.; Hong, K.; Meng, Y. G.; Weikert, S. H.; Presta, L. G., Lack of fucose on human IgG1 N-linked oligosaccharide improves binding to human FcγRIIIA and antibody-dependent cellular toxicity. *J. Biol. Chem.* 2002, 277, 26733-26740.

17. Shinkawa, T.; Nakamura, K.; Yamane, N.; Shoji-Hosaka, E.; Kanda, Y.; Sakurada, M.; Uchida, K.; Anazawa, H.; Satoh, M.; Yamasaki, M.; Hanai, N.; shi-ara, K., The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity. *J. Biol. Chem.* 2003, 278, 3466-3473.

18. Niwa, R.; Shoji-Hosaka, E.; Sakurada, M.; Shinkawa, T.; Uchida, K.; Nakamura, K.; Matsushima, K.; Ueda, R.; Hanai, N.; shi-ara, K., Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma. *Cancer Res.* 2004, 64, 2127-2133.

19. Strome, S. E.; Sausville, E. A.; Mann, D., A mechanistic perspective of monoclonal antibodies in cancer therapy beyond target-related effects. *Oncologist* 2007, 12, 1084-1095.

20. Jefferis, R., Glycosylation of antibody therapeutics: optimisation for purpose. *Methods Mol. Biol.* 2009, 483, 223-238.

21. Kaneko, Y.; Nimmerjahn, F.; Ravetch, J. V., Anti-Inflammatory Activity of Immunoglobulin G Resulting from Fc Sialylation. *Science* 2006, 313, 670-673.

22. Anthony, R. M.; Nimmerjahn, F.; Ashline, D. J.; Reinhold, V. N.; Paulson, J. C.; Ravetch, J. V., Recapitulation of IVIG Anti-Inflammatory Activity with a Recombinant IgG Fc. *Science* 2008, 320, 373-376.

23. Anthony, R. M.; Wermeling, F.; Karlsson, M. C.; Ravetch, J. V., Identification of a receptor required for the anti-inflammatory activity of IVIG. *Proc. Natl. Acad. Sci. U.S.A.* 2008, 105, 19571-19578.

24. Umana, P.; Jean-Mairet, J.; Moudry, R.; Amstutz, H.; Bailey, J. E., Engineered glycoforms of an antineuroblastoma IgG1 with optimized antibody-dependent cellular cytotoxic activity. *Nat. Biotechnol.* 1999, 17, 176-180.

25. Yamane-Ohnuki, N.; Kinoshita, S.; Inoue-Urakubo, M.; Kusunoki, M.; Iida, S.; Nakano, R.; Wakitani, M.; Niwa, R.; Sakurada, M.; Uchida, K.; shi-ara, K.; Satoh, M., Establishment of FUT8 knockout chinese hamster ovary cells: An ideal host cell line for producing completely defucosylated antibodies with enhanced antibody-dependent cellular cytotoxicity. *Biotechnol. Bioeng.* 2004, 87, 614-622.

26. Stanley, P.; Sundaram, S.; Tang, J.; Shi, S., Molecular analysis of three gain-of-function CHO mutants that add the bisecting GlcNAc to N-glycans. Glycobiology 2005, 15, 43-53.

27. Cox, K. M.; Sterling, J. D.; Regan, J. T.; Gasdaska, J. R.; Frantz, K. K.; Peele, C. G.; Black, A.; Passmore, D.; Moldovan-Loomis, C.; Srinivasan, M.; Cuison, S.; Cardarelli, P. M.; Dickey, L. F., Glycan optimization of a human monoclonal antibody in the aquatic plant *Lemna minor*. *Nat. Biotechnol.* 2006, 24, 1591-1597.

28. Strasser, R.; Castilho, A.; Stadlmann, J.; Kunert, R.; Quendler, H.; Gattinger, P.; Jez, J.; Rademacher, T.; Altmann, F.; Mach, L.; Steinkellner, H. J., Improved Virus Neutralization by Plant-produced Anti-HIV Antibodies with a Homogeneous 131,4-Galactosylated N-Glycan Profile. *Biol. Chem.* 2009, 284, 20479-20485.

29. Li, H.; Sethuraman, N.; Stadheim, T. A.; Zha, D.; Prinz, B.; Ballew, N.; Bobrowicz, P.; Choi, B. K.; Cook, W. J.; Cukan, M.; Houston-Cummings, N. R.; Davidson, R.; Gong, B.; Hamilton, S. R.; Hoopes, J. P.; Jiang, Y.; Kim, N.; Mansfield, R.; Nett, J. H.; Rios, S.; Strawbridge, R.; Wildt, S.; Gerngross, T. U., Optimization of humanized IgGs in glycoengineered *Pichia pastoris*. *Nat. Biotechnol.* 2006, 24, 210-215.

30. Zhou, Q.; Shankara, S.; Roy, A.; Qiu, H.; Estes, S.; McVie-Wylie, A.; Culm-Merdek, K.; Park, A.; Pan, C.; Edmunds, T., Development of a simple and rapid method for producing non-fucosylated oligomannose containing antibodies with increased effector function. *Biotechnol. Bioeng.* 2008, 99, 652-665.

31. Schiestl, M.; Stangler, T.; Torella, C.; Cepeljnik, T.; Toll, H.; Grau, R., Acceptable changes in quality attributes of glycosylated biopharmaceuticals. *Nat. Biotechnol.* 2011, 29, 310-312.

32. Wang, L. X.; Lomino, J. V., Emerging Technologies for Making Glycan-Defined Glycoproteins. *ACS Chem. Biol.* 2012, 7, 110-122.

33. Wang, L. X., The amazing transglycosylation activity of endo-β-N-acetylglucosaminidases. *Trends Glycosci. Glycotechnol.* 2011, 23, 33-52.

34. Wei, Y.; Li, C.; Huang, W.; Li, B.; Strome, S.; Wang, L. X., Glycoengineering of Human IgG1-Fc through Combined Yeast Expression and in Vitro Chemoenzymatic Glycosylation. *Biochemistry* 2008, 47, 10294-10304.

35. Zou, G.; Ochiai, H.; Huang, W.; Yang, Q.; Li, C.; Wang, L. X., Chemoenzymatic Synthesis and Fcγ Receptor Binding of Homogeneous Glycoforms of Antibody Fc Domain. Presence of a Bisecting Sugar Moiety Enhances the Affinity of Fc to FcγIIIa Receptor. *J. Am. Chem. Soc.* 2011, 133, 18975-18991.

36. Fan, S. Q.; Huang, W.; Wang, L. X., Remarkable Transglycosylation Activity of Glycosynthase Mutants of Endo-D, an Endo-β-N-acetylglucosaminidase from *Streptococcus pneumonia*. *J. Biol. Chem.* 2012, 287, 11272-11281.

37. Umekawa, M.; Li, C.; Higashiyama, T.; Huang, W.; Ashida, H.; Yamamoto, K.; Wang, L. X., Efficient glycosynthase mutant derived from *Mucor hiemalis* endo-β-N-acetylglucosaminidase capable of transferring oligosaccharide from both sugar oxazoline and natural N-glycan. *J. Biol. Chem.* 2010, 285, 511-521.

38. Huang, W.; Li, C.; Li, B.; Umekawa, M.; Yamamoto, K.; Zhang, X.; Wang, L. X., Glycosynthases Enable a Highly Efficient Chemoenzymatic Synthesis of N-Glycoproteins Carrying Intact Natural N-Glycans. *J. Am. Chem. Soc.* 2009, 131, 2214-2223.

39. Umekawa, M.; Huang, W.; Li, B.; Fujita, K.; Ashida, H.; Wang, L. X.; Yamamoto, K., Mutants of *Mucor hiemalis* Endo-β-N-acetylglucosaminidase Show Enhanced Transglycosylation and Glycosynthase-like Activities. *J. Biol. Chem.* 2008, 283, 4469-4479.

40. Collin, M.; Olsen, A., EndoS, a novel secreted protein from *Streptococcus pyogenes* with endoglycosidase activity on human IgG. *EMBO J.* 2001, 20, 3046-3055.

41. Allhorn, M.; Olsen, A.; Collin, M., EndoS from *Streptococcus pyogenes* is hydrolyzed by the cysteine proteinase SpeB and requires glutamic acid 235 and tryptophans for IgG glycan-hydrolyzing activity. *BMC Microbiol.* 2008, 8, 3.

42. Goodfellow, J. J.; Baruah, K.; Yamamoto, K.; Bonomelli, C.; Krishna, B.; Harvey, D. J.; Crispin, M.; Scanlan, C. N.; Davis, B. G., An Endoglycosidase with Alternative Glycan Specificity Allows Broadened Glycoprotein Remodelling. *J. Am. Chem. Soc.* 2012, 134, 8030-8033.

43. Umekawa, M.; Higashiyama, T.; Koga, Y.; Tanaka, T.; Noguchi, M.; Kobayashi, A.; Shoda, S.; Huang, W.; Wang, L. X.; Ashida, H.; Yamamoto, K., Efficient transfer of sialo-oligosaccharide onto proteins by combined use of a glycosynthase-like mutant of *Mucor hiemalis* endoglycosidase and synthetic sialo-complex-type sugar oxazoline. *Biochim. Biophys. Acta* 2010, 1800, 1203-1209.

44. Huang, W.; Li, J.; Wang, L. X., Unusual Transglycosylation Activity of *Flavobacterium meningosepticum* Endoglycosidases Enables Convergent Chemoenzymatic Synthesis of Core Fucosylated Complex N-Glycopeptides. *ChemBioChem* 2011, 12, 932-941.

45. Waddling, C. A.; Plummer, T. H., Jr.; Tarentino, A. L.; Van Roey, P., Structural Basis for the Substrate Specificity of Endo-β-N-acetylglucosaminidase F3. *Biochemistry* 2000, 39, 7878-7885.

46. Huang, W.; Yang, Q.; Umekawa, M.; Yamamoto, K.; Wang, L. X., *Arthrobacter* Endo-β-N-Acetylglucosaminidase Shows Transglycosylation Activity on Complex-Type N-Glycan Oxazolines: One-Pot Conversion of Ribonuclease B to Sialylated Ribonuclease C. *ChemBioChem* 2010, 11, 1350-1355.

47. Wan, H. Z.; Kaneshiro, S.; Frenz, J.; Cacia, J., Rapid method for monitoring galactosylation levels during recombinant antibody production by electrospray mass spectrometry with selective-ion monitoring. *J. Chromatogr., A* 2001, 913, 437-446.

48. Li, B.; Zeng, Y.; Hauser, S.; Song, H.; Wang, L. X., Highly Efficient Endoglycosidase-Catalyzed Synthesis of Glycopeptides Using Oligosaccharide Oxazolines as Donor Substrates. *J. Am. Chem. Soc.* 2005, 127, 9692-9693.

49. Ochiai, H.; Huang, W.; Wang, L. X., Expeditious Chemoenzymatic. *J. Am. Chem. Soc.* 2008, 130, 13790-13803.

50. Sletten, E. M.; Bertozzi, C. R., From Mechanism to Mouse: A Tale of Two Bioorthogonal Reactions. *Acc. Chem. Res.* 2011, 44, 666-676.

51. Best, M. D., Click Chemistry and Bioorthogonal Reactions: Unprecedented Selectivity in the Labeling of Biological Molecules. *Biochemistry* 2009, 48, 6571-6584.

52. Cartron, G.; Dacheux, L.; Salles, G.; Solal-Celigny, P.; Bardos, P.; Colombat, P.; Watier, H., Therapeutic activity of a humanized anti-CD20 monoclonal antibody and polymorphism in IgG Fc receptor FcγRIIIa gene. *Blood* 2002, 99, 754-758.

53. Sazinsky, S. L.; Ott, R. G.; Silver, N. W.; Tidor, B.; Ravetch, J. V.; Wittrup, K. D., Aglycosylated immunoglobulin G1 variants productively engage activating Fc receptors. *Proc. Natl. Acad. Sci. U.S.A.* 2008, 105, 20167-20172.

54. Anthony, R. M.; Kobayashi, T.; Wermeling, F.; Ravetch, J. V., Intravenous gammaglobulin suppresses inflammation through a novel TH2 pathway. *Nature* 2011, 475, 110-113.

55. Huhn, C.; Selman, M. H.; Ruhaak, L. R.; Deelder, A. M.; Wuhrer, M., IgG glycosylation analysis. *Proteomics* 2009, 9, 882-913.

56. Barb, A. W.; Brady, E. K.; Prestegard, J. H., Branch-Specific Sialylation of IgG-Fc Glycans by ST6Gal-I. *Biochemistry* 2009, 48, 9705-9707.

57. Guhr, T.; Bloem, J.; Derksen, N. I.; Wuhrer, M.; Koenderman, A. H.; Aalberse, R. C.; Rispens, T., Enrichment of sialylated IgG by lectin fractionation does not enhance the efficacy of immunoglobulin G in a murine model of immune thrombocytopenia. *PLoS One* 2011, 6, e21246.

58. Raju, T. S.; Scallon, B., Glycosylation in the Fc domain of IgG increases resistance to proteolytic cleavage by papain. *J. Biochem. Biophys. Res. Commun.* 2006, 341, 797-803.

59. Guile, G. R.; Rudd, P. M.; Wing, D. R.; Prime, S. B.; Dwek, R. A., A rapid high-resolution high-performance liquid chromatographic method for separating glycan mixtures and analyzing oligosaccharide profiles. *Anal. Biochem.* 1996, 240, 210-226.

60. Johnson, P.; Glennie, M., The mechanisms of action of rituximab in the elimination of tumor cells. *Semin. Oncol.* 2003, 30, 3-8.

61. Koene, H. R.; Kleijer, M.; Algra, J.; Roos, D.; von dem Borne, A. E.; de Haas, M., FcγRIIIa-158V/F polymorphism influences the binding of IgG by natural killer cell FcγRIIIa, independently of the FcγRIIIa-48L/R/H phenotype. *Blood* 1997, 90, 1109-1114.

62. Hessell, A. J.; Hangartner, L.; Hunter, M.; Havenith, C. E.; Beurskens, F. J.; Bakker, J. M.; Lanigan, C. M.; Landucci, G.; Forthal, D. N.; Parren, P. W.; Marx, P. A.; Burton, D. R., Fc receptor but not complement binding is important in antibody protection against HIV. *Nature* 2007, 449, 101-104.

63. Collin, M.; Olsen, A., Effect of SpeB and EndoS from *Streptococcus pyogenes* on human immunoglobulins. *Infect. Immun.* 2001, 69, 7187-7189.

That which is claimed is:

1. An Endoglycosidase-S mutant comprising SEQ ID NO: 2 having a D233Q substitution.

2. A method of producing nonfucosylated IgG glycoforms, comprising:
   a) deglycosylating an Fc domain of IgG glycoforms to produce a GlcNAc-acceptor;
   b) removing α-1,6-fucose moieties by exposing the GlcNAC-acceptor to a concentration of α-fucosidase for an amount of time necessary to defucosylate the GlcNAC-acceptor to yield nonfucosylated GlcNAC-acceptors;
   c) enzymatically reacting the nonfucosylated GlcNAc-acceptors with an activated oligosaccharide donor using a *Streptococcus pyogenes* Endoglycosidase-S Asp233 mutant comprising SEQ ID NO: 2 having a D233Q substitution, wherein the activated oligosaccharide donor carries an oligosaccharide moiety comprising a predetermined number and type of sugar residues.

3. The method of claim 2, wherein the IgG glycoforms are deglycosylated using an endoglycosidase selected from the group consisting of Endo-H, Endo-F3, wild-type Endo S, and Endo-A.

4. The method of claim 2, wherein the activated oligosaccharide donor is a synthetic oligosaccharide oxazoline or sialylated oxazoline.

5. The method of claim 4, wherein the synthetic oligosaccharide oxazoline is a di-, tri-, tetra-, penta-, hexyl-, hepta-, octyl-, nona-, deca- or undeca-saccharide oxazoline.

6. The method of claim 2, wherein the activated oligosaccharide donor further comprises an additional biologically active agent or a tag.

7. The method of claim 2, wherein the nonfucosylated IgG glycoform is a monoclonal antibody selected from the group consisting of 17b, 48d, A32, C11, 2G12, F240, IgG1b12, 19e, X5, TNX-355, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101, volociximab, Anti-CD80 mAb, Anti-CD23 mAb, CAT-3888, CDP-791, eraptuzumab, MDX-010, MDX-060, MDX-070, matuzumab, CP-675,206, CAL, SGN-30, zanolimumab, adecatumumab, oregovomab, nimotuzumab, ABT-874, denosumab, AM 108, AMG 714, fontolizumab, daclizumab, golimumab, CNTO 1275, ocrelizumab, HuMax-CD20, belimumab, epratuzumab, MLN1202, visilizumab, tocilizumab, ocrerlizumab, certolizumab pegol, eculizumab, pexelizumab, abciximab, ranibizimumab, mepolizumab and MYO-029.

8. The method of claim 2, wherein the nonfucosylated IgG glycoforms are substantially homogeneous.

* * * * *

SEQUENCE LISTING

<160> NUMBER OF SEQ ID NOS: 5

<210> SEQ ID NO 1
<211> LENGTH: 995
<212> TYPE: PRT
<213> ORGANISM: Streptococcus pyogenes

<400> SEQUENCE: 1

-continued

```
Met Asp Lys His Leu Leu Val Lys Arg Thr Leu Gly Cys Val Cys Ala
1               5                   10                  15
Ala Thr Leu Met Gly Ala Ala Leu Ala Thr His His Asp Ser Leu Asn
                20                  25                  30
Thr Val Lys Ala Glu Glu Lys Thr Val Gln Val Gln Lys Gly Leu Pro
            35                  40                  45
Ser Ile Asp Ser Leu His Tyr Leu Ser Glu Asn Ser Lys Lys Glu Phe
50                  55                  60
Lys Glu Glu Leu Ser Lys Ala Gly Gln Glu Ser Gln Lys Val Lys Glu
65                  70                  75                  80
Ile Leu Ala Lys Ala Gln Gln Ala Asp Lys Gln Ala Gln Glu Leu Ala
                85                  90                  95
Lys Met Lys Ile Pro Glu Lys Ile Pro Met Lys Pro Leu His Gly Pro
            100                 105                 110
Leu Tyr Gly Gly Tyr Phe Arg Thr Trp His Asp Lys Thr Ser Asp Pro
            115                 120                 125
Thr Glu Lys Asp Lys Val Asn Ser Met Gly Glu Leu Pro Lys Glu Val
130                 135                 140
Asp Leu Ala Phe Ile Phe His Asp Trp Thr Lys Asp Tyr Ser Leu Phe
145                 150                 155                 160
Trp Lys Glu Leu Ala Thr Lys His Val Pro Lys Leu Asn Lys Gln Gly
                165                 170                 175
Thr Arg Val Ile Arg Thr Ile Pro Trp Arg Phe Leu Ala Gly Gly Asp
            180                 185                 190
Asn Ser Gly Ile Ala Glu Asp Thr Ser Lys Tyr Pro Asn Thr Pro Glu
            195                 200                 205
Gly Asn Lys Ala Leu Ala Lys Ala Ile Val Asp Glu Tyr Val Tyr Lys
            210                 215                 220
Tyr Asn Leu Asp Gly Leu Asp Val Asp Val Glu His Asp Ser Ile Pro
225                 230                 235                 240
Lys Val Asp Lys Lys Glu Asp Thr Ala Gly Val Glu Arg Ser Ile Gln
                245                 250                 255
Val Phe Glu Glu Ile Gly Lys Leu Ile Gly Pro Lys Gly Val Asp Lys
            260                 265                 270
Ser Arg Leu Phe Ile Met Asp Ser Thr Tyr Met Ala Asp Lys Asn Pro
            275                 280                 285
Leu Ile Glu Arg Gly Ala Pro Tyr Ile Asn Leu Leu Leu Val Gln Val
            290                 295                 300
Tyr Gly Ser Gln Gly Glu Lys Gly Gly Trp Glu Pro Val Ser Asn Arg
305                 310                 315                 320
Pro Glu Lys Thr Met Glu Glu Arg Trp Gln Gly Tyr Ser Lys Tyr Ile
                325                 330                 335
Arg Pro Glu Gln Tyr Met Ile Gly Phe Ser Phe Tyr Glu Glu Asn Ala
            340                 345                 350
Gln Glu Gly Asn Leu Trp Tyr Asp Ile Asn Ser Arg Lys Asp Glu Asp
            355                 360                 365
Lys Ala Asn Gly Ile Asn Thr Asp Ile Thr Gly Thr Arg Ala Glu Arg
            370                 375                 380
Tyr Ala Arg Trp Gln Pro Lys Thr Gly Gly Val Lys Gly Gly Ile Phe
385                 390                 395                 400
Ser Tyr Ala Ile Asp Arg Asp Gly Val Ala His Gln Pro Lys Lys Tyr
                405                 410                 415
```

-continued

Ala Lys Gln Lys Glu Phe Lys Asp Ala Thr Asp Asn Ile Phe His Ser
                420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
        675                 680                 685

Lys Ile Ala Gly Arg Ser Phe Val Asp Ser Asn Tyr His Tyr Asn Asn
    690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
        755                 760                 765

Ala Glu Gly Ala Thr Val Ile Gly Gly Ser Ala Asp Pro Val Asn Ala
    770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn

```
            835                 840                 845
Ile Lys Asp Tyr Asn Leu Asp Asn Leu Leu Glu Asn Pro Asn Lys Phe
850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                    885                 890                 895

Tyr Trp Arg Val Val Phe Asp Thr Lys Gly Asp Arg Tyr Ser Ser Pro
                900                 905                 910

Val Val Pro Glu Leu Gln Ile Leu Gly Tyr Pro Leu Pro Asn Ala Asp
                915                 920                 925

Thr Ile Met Lys Thr Val Thr Thr Ala Lys Glu Leu Ser Gln Gln Lys
930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
                980                 985                 990

Leu Lys Lys
        995

<210> SEQ ID NO 2
<211> LENGTH: 995
<212> TYPE: PRT
<213> ORGANISM: Artificial Sequence
<220> FEATURE:
<223> OTHER INFORMATION: Synthetic construct

<400> SEQUENCE: 2

Met Asp Lys His Leu Leu Val Lys Arg Thr Leu Gly Cys Val Cys Ala
1               5                   10                  15

Ala Thr Leu Met Gly Ala Ala Leu Ala Thr His His Asp Ser Leu Asn
                20                  25                  30

Thr Val Lys Ala Glu Glu Lys Thr Val Gln Val Gln Lys Gly Leu Pro
                35                  40                  45

Ser Ile Asp Ser Leu His Tyr Leu Ser Glu Asn Ser Lys Lys Glu Phe
            50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
                100                 105                 110

Leu Tyr Gly Gly Tyr Phe Arg Thr Trp His Asp Lys Thr Ser Asp Pro
            115                 120                 125

Thr Glu Lys Asp Lys Val Asn Ser Met Gly Glu Leu Pro Lys Glu Val
        130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
                180                 185                 190

Asn Ser Gly Ile Ala Glu Asp Thr Ser Lys Tyr Pro Asn Thr Pro Glu
```

```
            195                 200                 205
Gly Asn Lys Ala Leu Ala Lys Ala Ile Val Asp Glu Tyr Val Tyr Lys
210                 215                 220

Tyr Asn Leu Asp Gly Leu Asp Val Gln Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
290                 295                 300

Tyr Gly Ser Gln Gly Glu Lys Gly Gly Trp Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
                340                 345                 350

Gln Glu Gly Asn Leu Trp Tyr Asp Ile Asn Ser Arg Lys Asp Glu Asp
            355                 360                 365

Lys Ala Asn Gly Ile Asn Thr Asp Ile Thr Gly Thr Arg Ala Glu Arg
370                 375                 380

Tyr Ala Arg Trp Gln Pro Lys Thr Gly Val Lys Gly Gly Ile Phe
385                 390                 395                 400

Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
                420                 425                 430

Asp Tyr Ser Val Ser Lys Ala Leu Lys Thr Val Met Leu Lys Asp Lys
            435                 440                 445

Ser Tyr Asp Leu Ile Asp Glu Lys Asp Phe Pro Asp Lys Ala Leu Arg
        450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Glu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
    610                 615                 620
```

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
            645                 650                 655

Lys Val Asp Leu Gln Ser Gln Leu Leu Phe Gly Thr Val Thr Asn Gln
        660                 665                 670

Gly Thr Leu Ile Asn Ser Glu Ala Asp Tyr Lys Ala Tyr Gln Asn His
    675                 680                 685

Lys Ile Ala Gly Arg Ser Phe Val Asp Ser Asn Tyr His Tyr Asn Asn
690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
        755                 760                 765

Ala Glu Gly Ala Thr Val Ile Gly Gly Ser Ala Asp Pro Val Asn Ala
    770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
            820                 825                 830

Glu Thr Thr Asn Lys Pro Ile Gln Glu Ala Ser Leu Gln Ile Phe Asn
        835                 840                 845

Ile Lys Asp Tyr Asn Leu Asp Asn Leu Leu Glu Asn Pro Asn Lys Phe
    850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
    930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 3
<211> LENGTH: 995
<212> TYPE: PRT
<213> ORGANISM: Artificial Sequence
<220> FEATURE:

<223> OTHER INFORMATION: Synthetic Construct

<400> SEQUENCE: 3

```
Met Asp Lys His Leu Val Lys Arg Thr Leu Gly Cys Val Cys Ala
1               5                   10                  15

Ala Thr Leu Met Gly Ala Ala Leu Ala Thr His His Asp Ser Leu Asn
            20                  25                  30

Thr Val Lys Ala Glu Glu Lys Thr Val Gln Val Gln Lys Gly Leu Pro
        35                  40                  45

Ser Ile Asp Ser Leu His Tyr Leu Ser Glu Asn Ser Lys Lys Glu Phe
    50                  55                  60

Lys Glu Glu Leu Ser Lys Ala Gly Gln Glu Ser Gln Lys Val Lys Glu
65                  70                  75                  80

Ile Leu Ala Lys Ala Gln Gln Ala Asp Lys Gln Ala Gln Glu Leu Ala
                85                  90                  95

Lys Met Lys Ile Pro Glu Lys Ile Pro Met Lys Pro Leu His Gly Pro
            100                 105                 110

Leu Tyr Gly Gly Tyr Phe Arg Thr Trp His Asp Lys Thr Ser Asp Pro
        115                 120                 125

Thr Glu Lys Asp Lys Val Asn Ser Met Gly Glu Leu Pro Lys Glu Val
    130                 135                 140

Asp Leu Ala Phe Ile Phe His Asp Trp Thr Lys Asp Tyr Ser Leu Phe
145                 150                 155                 160

Trp Lys Glu Leu Ala Thr Lys His Val Pro Lys Leu Asn Lys Gln Gly
                165                 170                 175

Thr Arg Val Ile Arg Thr Ile Pro Trp Arg Phe Leu Ala Gly Gly Asp
            180                 185                 190

Asn Ser Gly Ile Ala Glu Asp Thr Ser Lys Tyr Pro Asn Thr Pro Glu
        195                 200                 205

Gly Asn Lys Ala Leu Ala Lys Ala Ile Val Asp Glu Tyr Val Tyr Lys
    210                 215                 220

Tyr Asn Leu Asp Gly Leu Asp Val Ala Val Glu His Asp Ser Ile Pro
225                 230                 235                 240

Lys Val Asp Lys Lys Glu Asp Thr Ala Gly Val Glu Arg Ser Ile Gln
                245                 250                 255

Val Phe Glu Glu Ile Gly Lys Leu Ile Gly Pro Lys Gly Val Asp Lys
            260                 265                 270

Ser Arg Leu Phe Ile Met Asp Ser Thr Tyr Met Ala Asp Lys Asn Pro
        275                 280                 285

Leu Ile Glu Arg Gly Ala Pro Tyr Ile Asn Leu Leu Leu Val Gln Val
    290                 295                 300

Tyr Gly Ser Gln Gly Glu Lys Gly Gly Trp Glu Pro Val Ser Asn Arg
305                 310                 315                 320

Pro Glu Lys Thr Met Glu Glu Arg Trp Gln Gly Tyr Ser Lys Tyr Ile
                325                 330                 335

Arg Pro Glu Gln Tyr Met Ile Gly Phe Ser Phe Tyr Glu Glu Asn Ala
            340                 345                 350

Gln Glu Gly Asn Leu Trp Tyr Asp Ile Asn Ser Arg Lys Asp Glu Asp
        355                 360                 365

Lys Ala Asn Gly Ile Asn Thr Asp Ile Thr Gly Thr Arg Ala Glu Arg
    370                 375                 380

Tyr Ala Arg Trp Gln Pro Lys Thr Gly Gly Val Lys Gly Gly Ile Phe
385                 390                 395                 400
```

-continued

```
Ser Tyr Ala Ile Asp Arg Asp Gly Val Ala His Gln Pro Lys Lys Tyr
                405                 410                 415

Ala Lys Gln Lys Glu Phe Lys Asp Ala Thr Asp Asn Ile Phe His Ser
            420                 425                 430

Asp Tyr Ser Val Ser Lys Ala Leu Lys Thr Val Met Leu Lys Asp Lys
        435                 440                 445

Ser Tyr Asp Leu Ile Asp Glu Lys Asp Phe Pro Asp Lys Ala Leu Arg
    450                 455                 460

Glu Ala Val Met Ala Gln Val Gly Thr Arg Lys Gly Asp Leu Glu Arg
465                 470                 475                 480

Phe Asn Gly Thr Leu Arg Leu Asp Asn Pro Ala Ile Gln Ser Leu Glu
                485                 490                 495

Gly Leu Asn Lys Phe Lys Lys Leu Ala Gln Leu Asp Leu Ile Gly Leu
            500                 505                 510

Ser Arg Ile Thr Lys Leu Asp Arg Ser Val Leu Pro Ala Asn Met Lys
        515                 520                 525

Pro Gly Lys Asp Thr Leu Glu Thr Val Leu Thr Tyr Lys Lys Asp
    530                 535                 540

Asn Lys Glu Glu Pro Ala Thr Ile Pro Pro Val Ser Leu Lys Val Ser
545                 550                 555                 560

Gly Leu Thr Gly Leu Lys Glu Leu Asp Leu Ser Gly Phe Asp Arg Glu
                565                 570                 575

Thr Leu Ala Gly Leu Asp Ala Ala Thr Leu Thr Ser Leu Glu Lys Val
            580                 585                 590

Asp Ile Ser Gly Asn Lys Leu Asp Leu Ala Pro Gly Thr Glu Asn Arg
        595                 600                 605

Gln Ile Phe Asp Thr Met Leu Ser Thr Ile Ser Asn His Val Gly Ser
    610                 615                 620

Asn Glu Gln Thr Val Lys Phe Asp Lys Gln Lys Pro Thr Gly His Tyr
625                 630                 635                 640

Pro Asp Thr Tyr Gly Lys Thr Ser Leu Arg Leu Pro Val Ala Asn Glu
                645                 650                 655

Lys Val Asp Leu Gln Ser Gln Leu Leu Phe Gly Thr Val Thr Asn Gln
            660                 665                 670

Gly Thr Leu Ile Asn Ser Glu Ala Asp Tyr Lys Ala Tyr Gln Asn His
        675                 680                 685

Lys Ile Ala Gly Arg Ser Phe Val Asp Ser Asn Tyr His Tyr Asn Asn
    690                 695                 700

Phe Lys Val Ser Tyr Glu Asn Tyr Thr Val Lys Val Thr Asp Ser Thr
705                 710                 715                 720

Leu Gly Thr Thr Thr Asp Lys Thr Leu Ala Thr Asp Lys Glu Glu Thr
                725                 730                 735

Tyr Lys Val Asp Phe Phe Ser Pro Ala Asp Lys Thr Lys Ala Val His
            740                 745                 750

Thr Ala Lys Val Ile Val Gly Asp Glu Lys Thr Met Met Val Asn Leu
        755                 760                 765

Ala Glu Gly Ala Thr Val Ile Gly Gly Ser Ala Asp Pro Val Asn Ala
    770                 775                 780

Arg Lys Val Phe Asp Gly Gln Leu Gly Ser Glu Thr Asp Asn Ile Ser
785                 790                 795                 800

Leu Gly Trp Asp Ser Lys Gln Ser Ile Ile Phe Lys Leu Lys Glu Asp
                805                 810                 815

Gly Leu Ile Lys His Trp Arg Phe Phe Asn Asp Ser Ala Arg Asn Pro
```

```
                820                 825                 830

Glu Thr Thr Asn Lys Pro Ile Gln Glu Ala Ser Leu Gln Ile Phe Asn
            835                 840                 845

Ile Lys Asp Tyr Asn Leu Asp Asn Leu Leu Glu Asn Pro Asn Lys Phe
        850                 855                 860

Asp Asp Glu Lys Tyr Trp Ile Thr Val Asp Thr Tyr Ser Ala Gln Gly
865                 870                 875                 880

Glu Arg Ala Thr Ala Phe Ser Asn Thr Leu Asn Asn Ile Thr Ser Lys
                885                 890                 895

Tyr Trp Arg Val Val Phe Asp Thr Lys Gly Asp Arg Tyr Ser Ser Pro
            900                 905                 910

Val Val Pro Glu Leu Gln Ile Leu Gly Tyr Pro Leu Pro Asn Ala Asp
        915                 920                 925

Thr Ile Met Lys Thr Val Thr Thr Ala Lys Glu Leu Ser Gln Gln Lys
            930                 935                 940

Asp Lys Phe Ser Gln Lys Met Leu Asp Glu Leu Lys Ile Lys Glu Met
945                 950                 955                 960

Ala Leu Glu Thr Ser Leu Asn Ser Lys Ile Phe Asp Val Thr Ala Ile
                965                 970                 975

Asn Ala Asn Ala Gly Val Leu Lys Asp Cys Ile Glu Lys Arg Gln Leu
            980                 985                 990

Leu Lys Lys
        995

<210> SEQ ID NO 4
<211> LENGTH: 60
<212> TYPE: PRT
<213> ORGANISM: Artificial Sequence
<220> FEATURE:
<223> OTHER INFORMATION: Sysnthetic Construct

<400> SEQUENCE: 4

Arg Thr Ile Pro Trp Arg Phe Leu Ala Gly Gly Asp Asn Ser Gly Ile
1               5                   10                  15

Ala Glu Asp Thr Ser Lys Tyr Pro Asn Thr Pro Glu Gly Asn Lys Ala
            20                  25                  30

Leu Ala Lys Ala Ile Val Asp Glu Tyr Val Tyr Lys Tyr Asn Leu Asp
        35                  40                  45

Gly Leu Asp Val Asp Val Glu His Asp Ser Ile Pro
    50                  55                  60

<210> SEQ ID NO 5
<211> LENGTH: 47
<212> TYPE: PRT
<213> ORGANISM: Artificial Sequence
<220> FEATURE:
<223> OTHER INFORMATION: Synthetic construct

<400> SEQUENCE: 5

Gln Asn Ile Asp Asp Asp Val Ser Trp Gln Ser Ser Lys Pro Gly Gly
1               5                   10                  15

Phe Ala Ser Ala Ala Ala Tyr Gly Asp Ala Ile Lys Ser Ile Val Ile
            20                  25                  30

Asp Lys Trp Lys Leu Asp Gly Ile Ser Leu Asp Ile Glu His Ser
        35                  40                  45
```